United States Patent
Concha et al.

(10) Patent No.: US 7,361,734 B2
(45) Date of Patent: Apr. 22, 2008

(54) **S8 RRNA-BINDING PROTEIN FROM THE SMALL RIBOSOMAL SUBUNIT OF *STAPHYLOCOCCUS AUREUS***

(75) Inventors: Nestor O. Concha, King of Prussia, PA (US); Richard R. Gontarek, King of Prussia, PA (US); Cheryl A. Janson, Hinsdale, IL (US)

(73) Assignee: SmithKline Beecham Corporation, Philadelphia, PA (US)

( * ) Notice: Subject to any disclaimer, the term of this patent is extended or adjusted under 35 U.S.C. 154(b) by 470 days.

(21) Appl. No.: 10/492,581

(22) PCT Filed: Oct. 15, 2002

(86) PCT No.: PCT/US02/32859

§ 371 (c)(1),
(2), (4) Date: Aug. 4, 2004

(87) PCT Pub. No.: WO03/033531

PCT Pub. Date: Apr. 24, 2003

(65) Prior Publication Data

US 2005/0038611 A1 Feb. 17, 2005

Related U.S. Application Data

(60) Provisional application No. 60/329,439, filed on Oct. 15, 2001.

(51) Int. Cl.
*C07K 14/00* (2006.01)
(52) U.S. Cl. .................. 530/350; 530/412; 530/418
(58) Field of Classification Search ............. None
See application file for complete search history.

(56) References Cited

U.S. PATENT DOCUMENTS 6,356,845 B1   3/2002   Benson et al.
6,833,253 B2 *  12/2004  Choi ..................... 435/69.1

FOREIGN PATENT DOCUMENTS

WO      WO 02/08266 A2 *   1/2002

OTHER PUBLICATIONS

Wiencek et al. New strategies for protein crystal growth. Ann. Rev. Biomed. Eng. 1999, 1, 505-534.*
Gilliland et al. Crystallization of biological molecules for X-ray diffraction studies. Current Opinion in Structure Biology 1996, 6, 595-603.*
Ke et al. Crystallization of RNA and RNA-protein complexes. Methods 34, 2004, 408-414.*

* cited by examiner

*Primary Examiner*—Nashaat T. Nashed
(74) *Attorney, Agent, or Firm*—Jason C. Fedon; Edward R. Gimmi

(57) ABSTRACT

A *Staphylococcus aureus* S8 native crystalline structure and a *Staphylococcus aureus* S8 mode of binding with rRNA were identified.

4 Claims, 14 Drawing Sheets

Secondary structure elements of native S8 from *S. aureus*.

(a)

(b)

Figure 1. Secondary structure elements of native S8 from *S. aureus*.
(a)
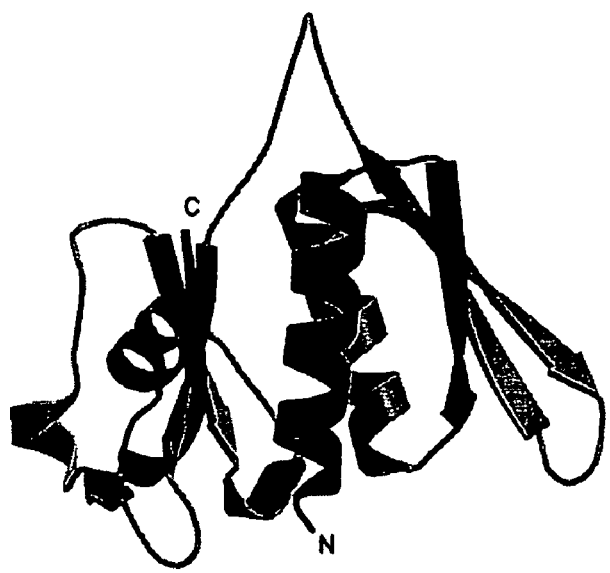
(b)

Figure 2. Purification of S. aureus ribosomal protein S8
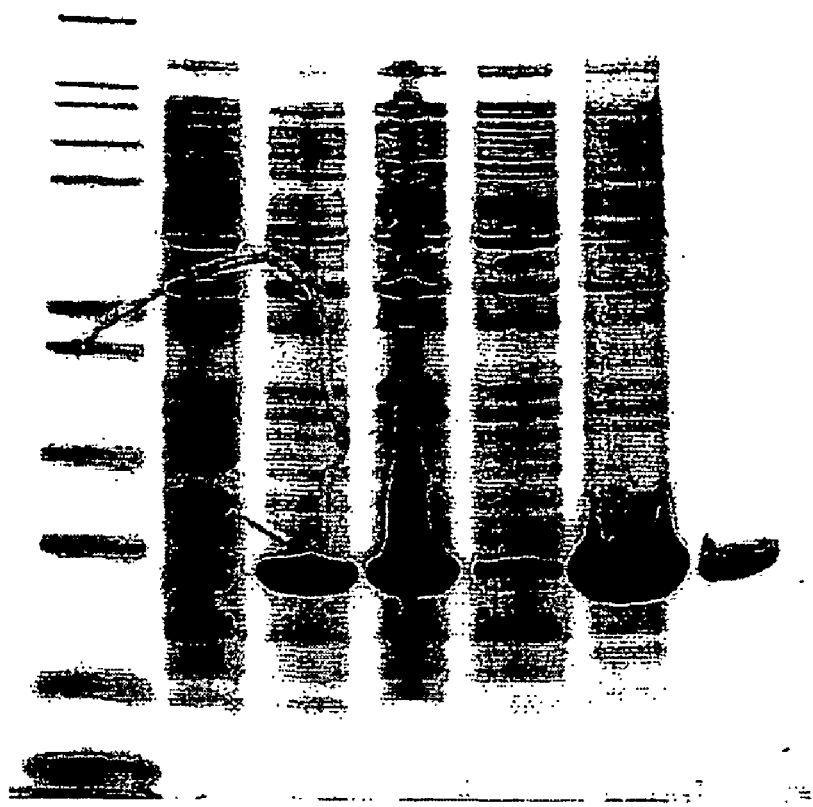

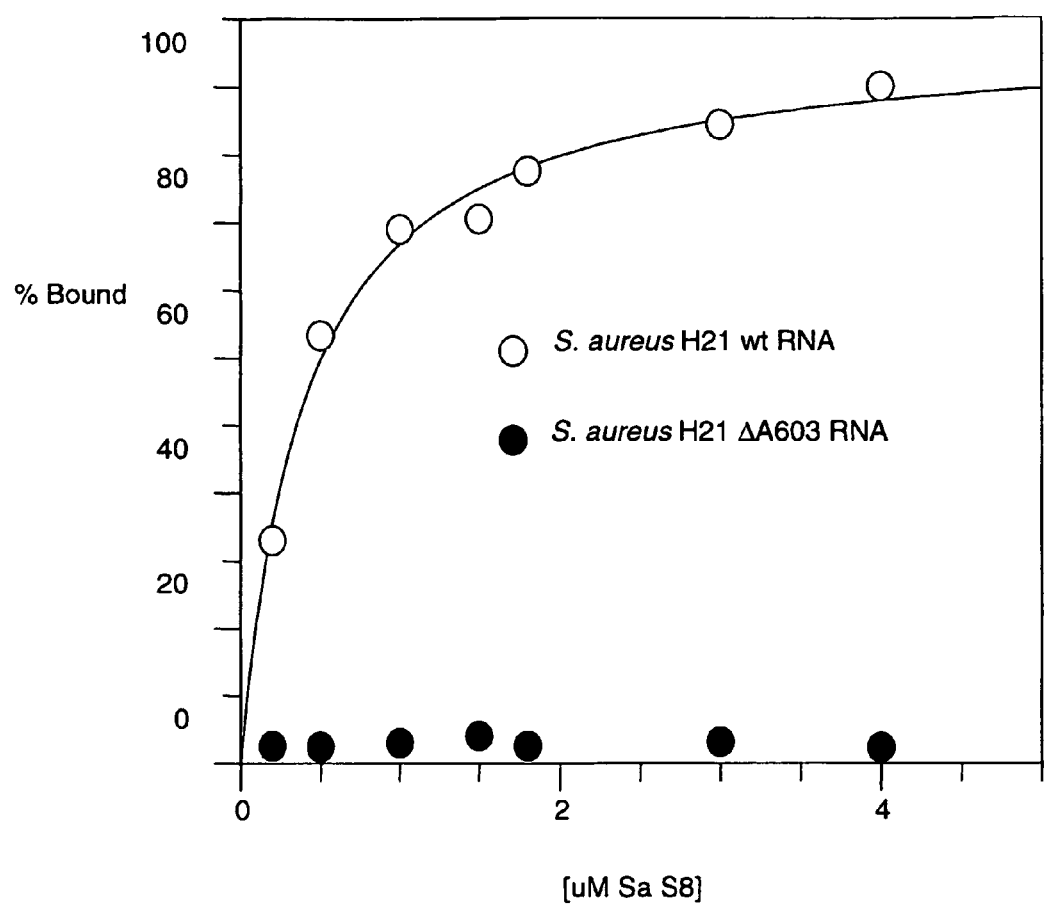
Figure 3. Filter-binding of *S. aureus* ribosomal protein S8 to wt and ΔA603 H21 RNA.

Figure 4. Sequence and predicted secondary strucutre of S. aureus helix 21 rRNA (nts 596-659) SEQ ID NO: 2.
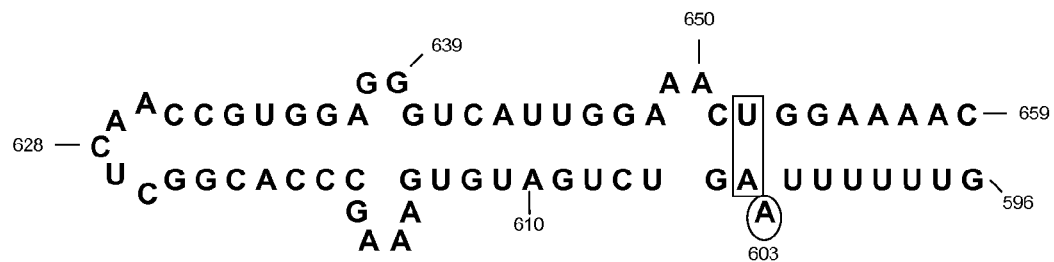

Figure 5. Diagrammatic representation of the S8-rRNA scintillation proximity assay.
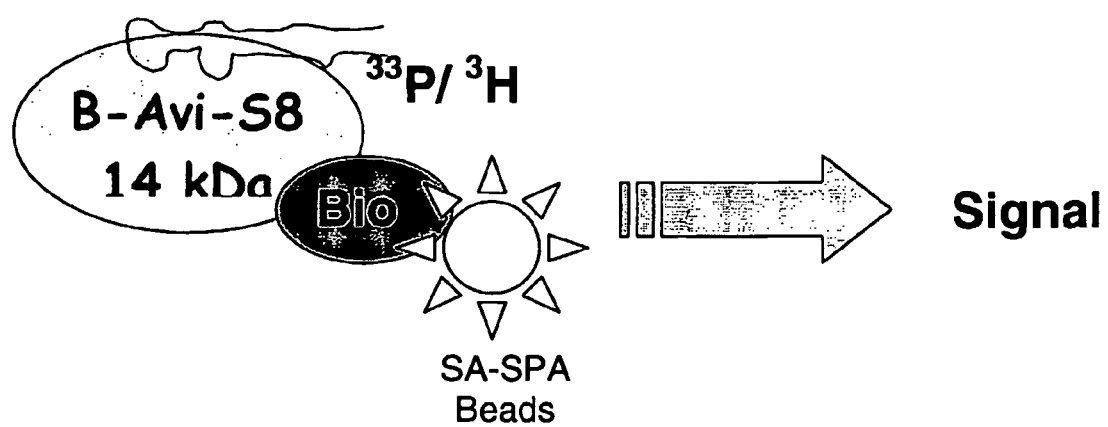

Figure 6. Scintillation proximity assay development
(a)
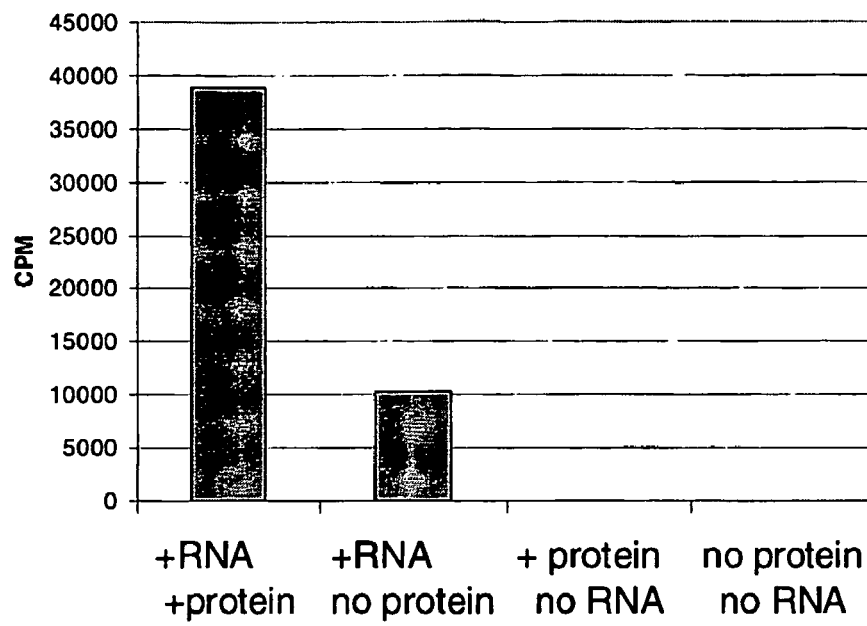
(b)
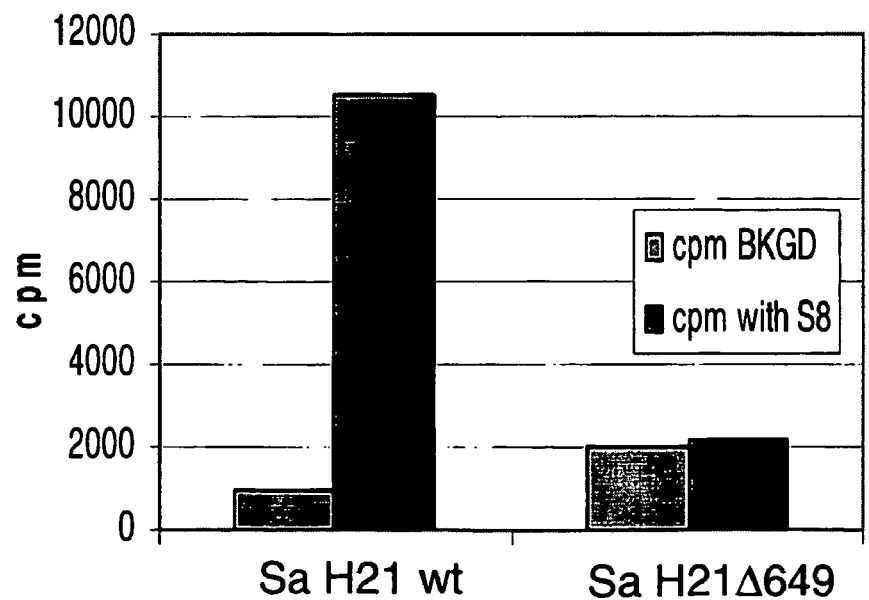

Figure 7. Residues critical for rRNA binding
(a)
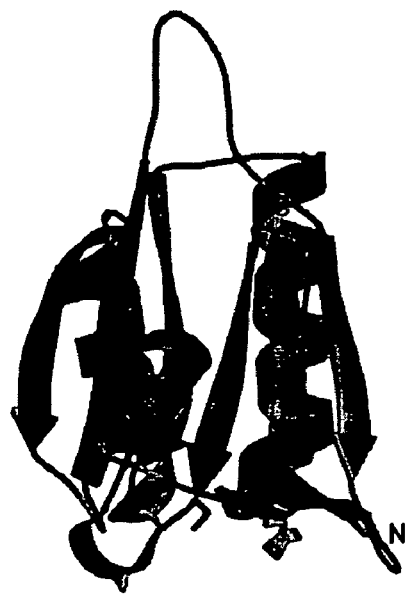
(b)

Figure 8. Binding of S8 to 16S rRNA via "lower" surface
(a)
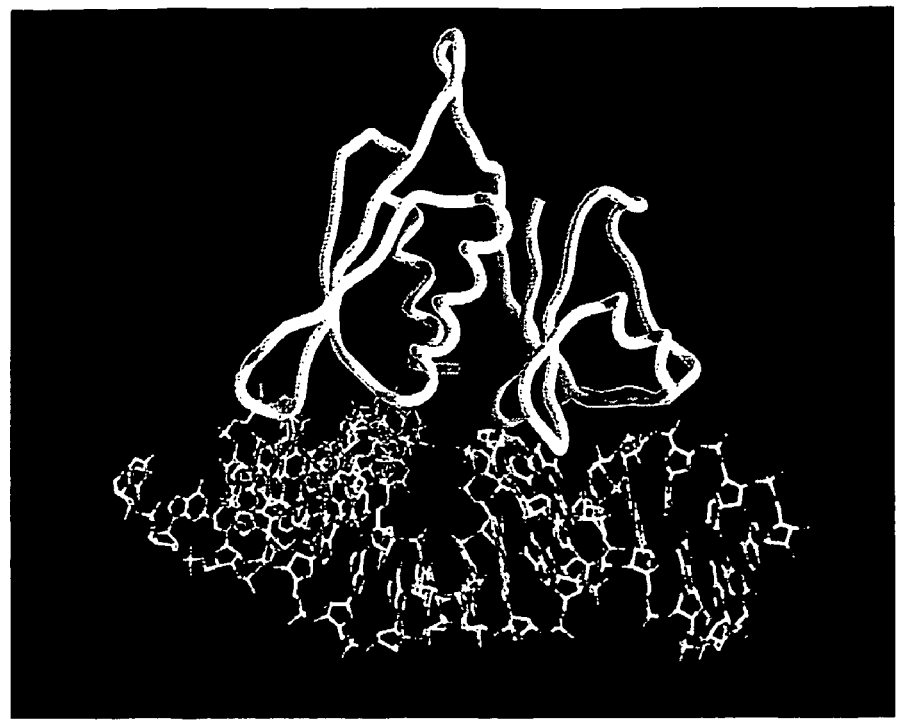
(b)
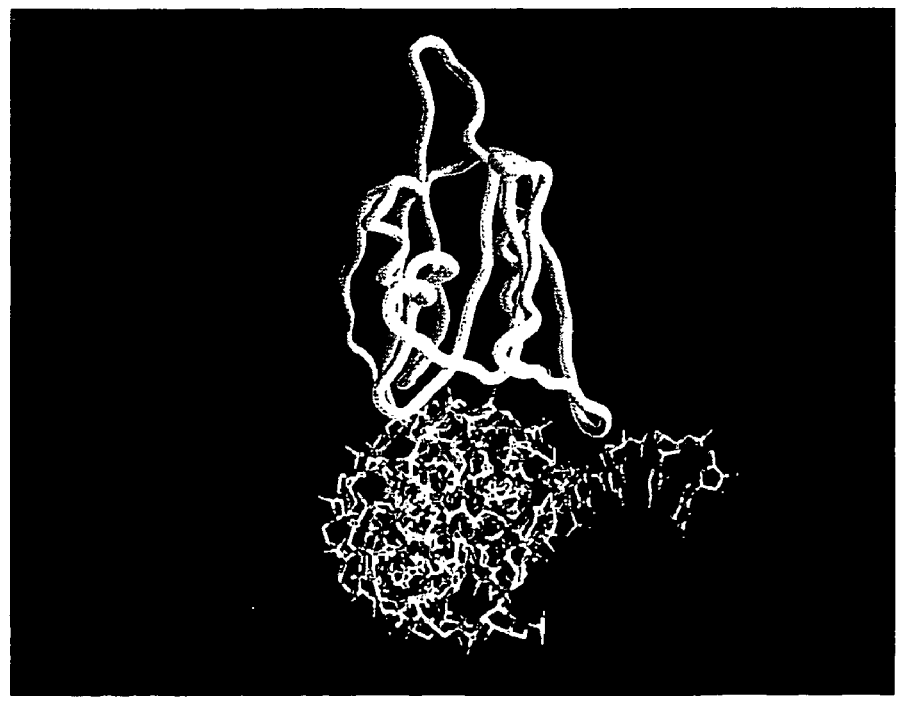

Figure 9. Binding of S8 to 16S rRNA via helix
(a)
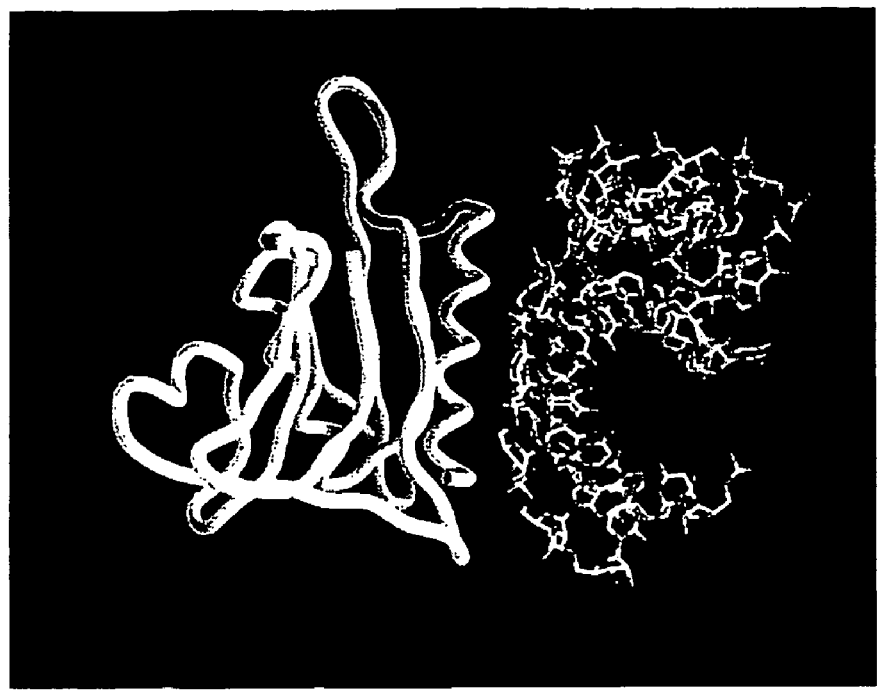
(b)
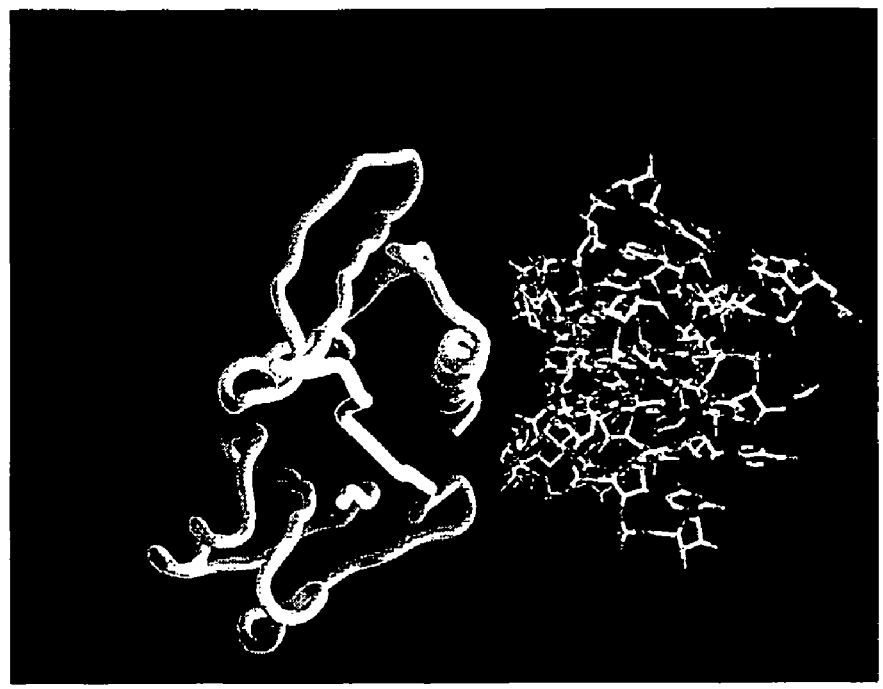

Figure 10. Binding of S8 to 16S rRNA
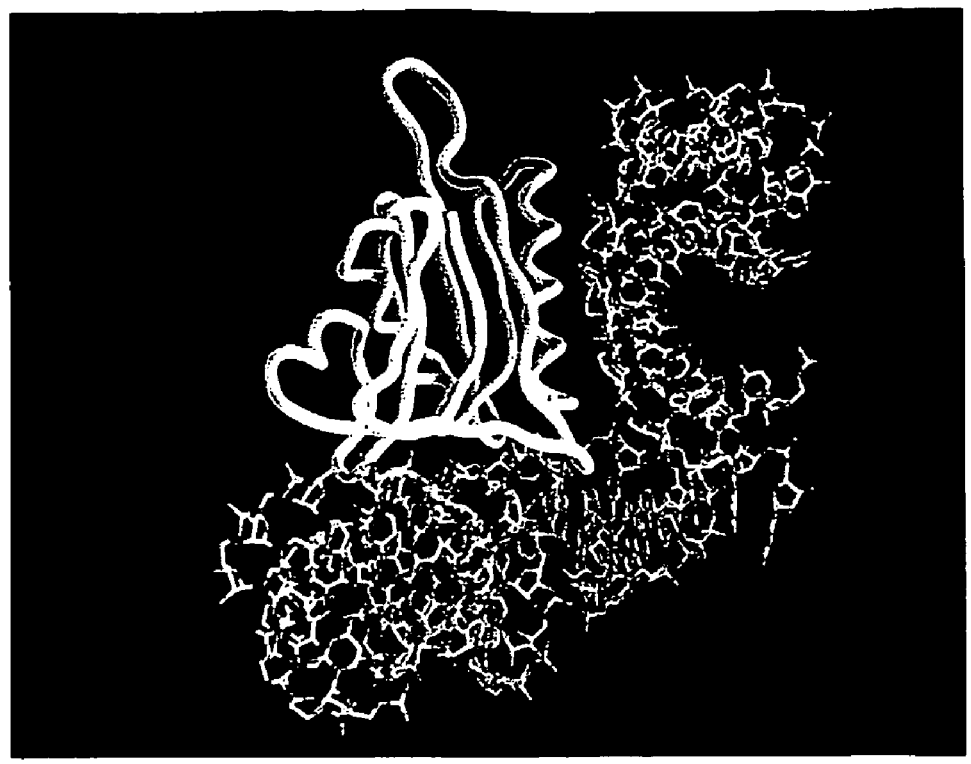

Figure 12. A representation of S8 from *S. aureus* (arrow) bound to the intact ribosome (rRNA, dark grey; protein, light grey/white). The S8-rRNA binding surface is exposed to small molecules dissolved in the bulk solvent.
(a)
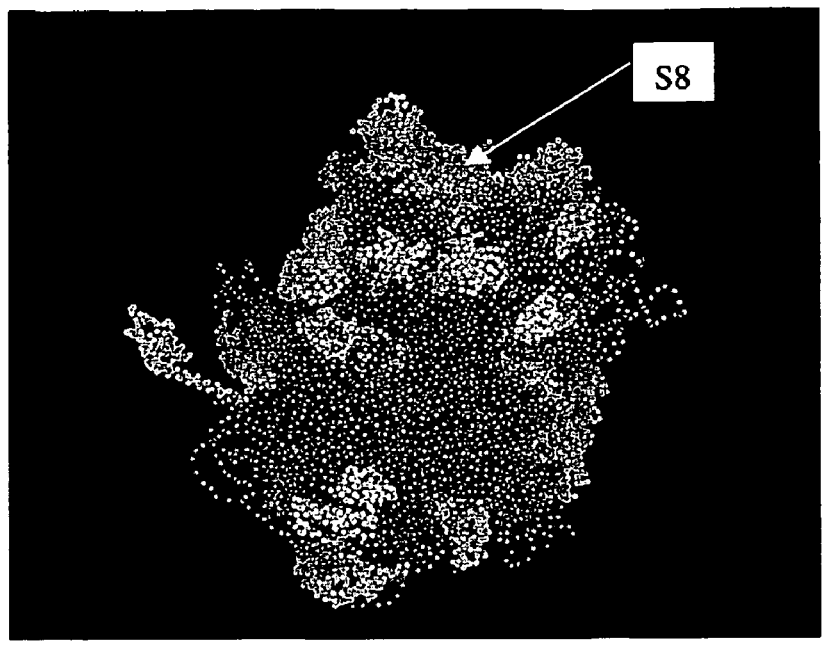
(b)
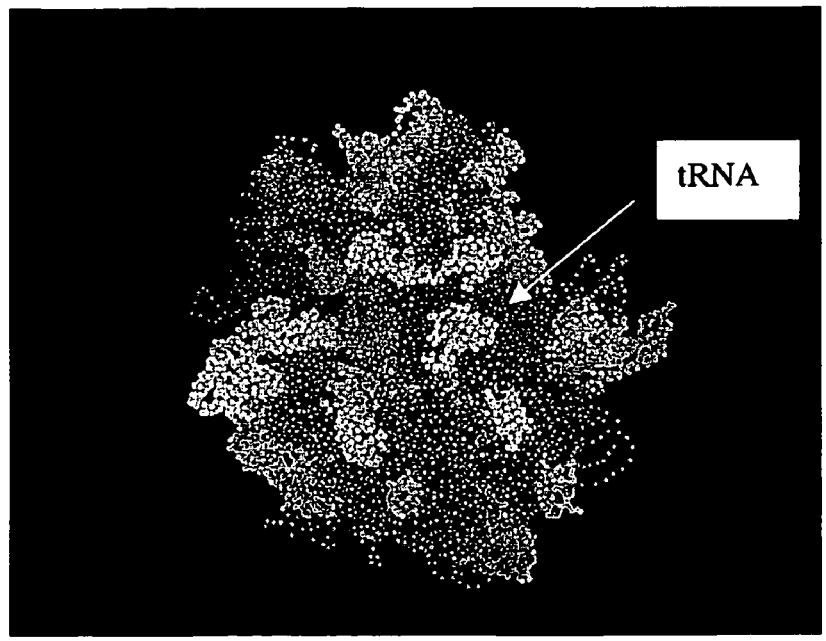

Figure 13. Model of *T. thermophilus* helix 21 rRNA binding to "underside" of *S. aureus* S8.
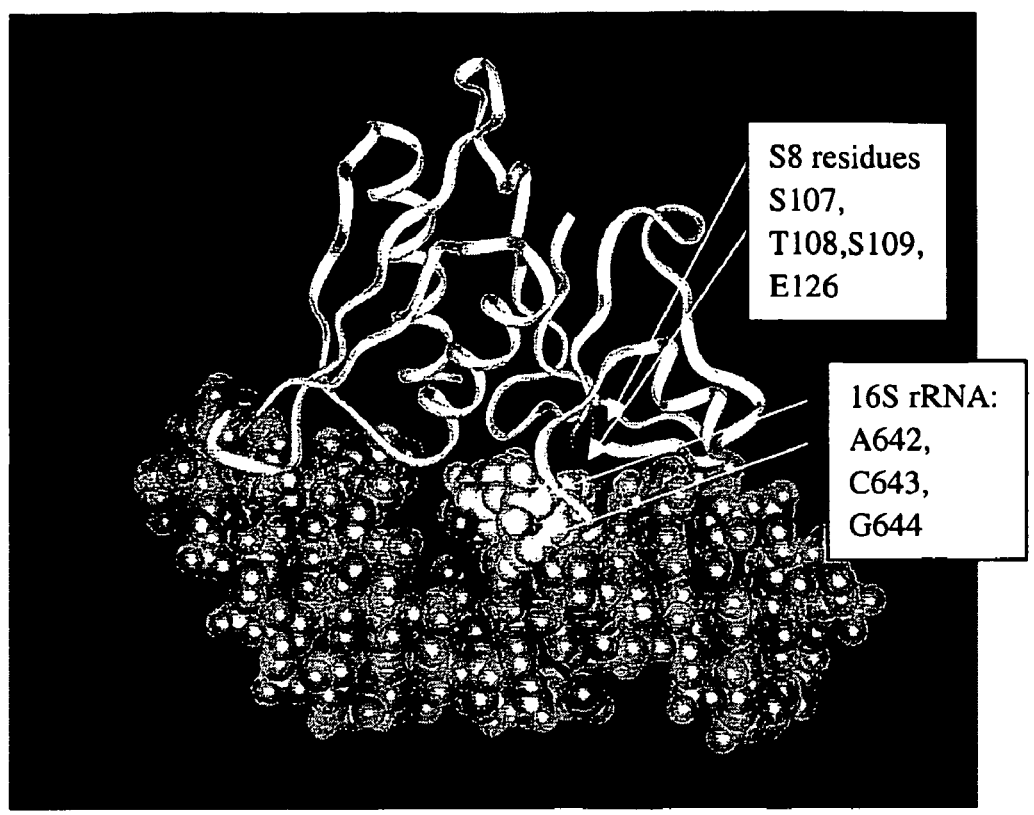

S8 RRNA-BINDING PROTEIN FROM THE SMALL RIBOSOMAL SUBUNIT OF STAPHYLOCOCCUS AUREUS

This application is a National Stage Application filed under 35 U.S.C. §371 of PCT/US02/32859, filed on 15 Oct. 2002 which claims the benefit of U.S. Provisional Application No. 60/329,439, filed 15 Oct. 2001.

TECHNICAL FIELD OF THE INVENTION

The invention relates to the identification of an RNA-binding domain, its mode of binding with a cognate RNA, and methods enabling design and selection of inhibitors of its binding site.

BACKGROUND OF THE INVENTION

With over 36 classes of known anti-ribosomal agents, the bacterial ribosome has been exploited for decades as a target for antibiotic drugs. The essentiality, selectivity, and conserved nature of bacterial translation continue to make the ribosome one of the most attractive targets for the discovery of antibacterial agents. The recent elucidation of the crystal structures of the 30S and 50S ribosomal subunits from *Thermus thermophilus* (Wimberly et al., (2000) *Nature* 407, 327-339) and *Haloarcula matsumorii* (Ban et al., (2000) *Science* 289, 905-920), respectively have provided an enormous amount of detailed structural information regarding RNA and protein structure, RNA-protein interactions, and ribosome assembly. In addition, these revolutionary discoveries have provided a structural basis for understanding the mechanistic processes of translation and the action of antibiotics, and may also allow for the de novo design of new antibacterial drugs that target the translation machinery.

Ribosomal protein S8 is an excellent target for the discovery of new antibacterials. In addition to being absolutely required for the proper assembly of the 30S ribosomal subunit in *E. coli*, the invention provide that S8 in *S. pneumoniae* is essential for bacterial growth. Moreover, alterations in S8-rRNA affinity can be correlated with growth defects that result from the expression of the same mutations in *E. coli* (Gregory and Zimmermann, (1986), *Nucleic Acids Research* 14, 5761-76). Ribosomal protein S8 is also a broad-spectrum target, as it is predicted to be very well conserved among bacterial species, see Table 1. Although there is a human ribosomal protein S8, it is significantly divergent and not thought to be a functional homolog of the bacterial S8. In addition, there does not appear to be any helix 21 homology in eukaryotic 18S rRNA.

Ribosomal protein S8 is a primary rRNA-binding protein that binds directly to a central region of bacterial 16S rRNA called Helix 21. Since S8 is required for the co-operative binding of all 30S proteins, it is essential for the proper assembly of the small ribosomal subunit (Held et al., (1974) *J. Biol. Chem* 249, 3101-3111). Indeed, mutations within the protein have been shown to result in ribosome assembly in defects in *E. coli* (Geyl et al. (1977) *Mol Gen Genet*. 29, 331-6). The binding site of S8 within Helix 21 rRNA has been extensively characterised in *E. coli*, and consists of two helical segments interrupted by a very highly conserved core element of irregular structure that spans nucleotides 595-598 and 640-644 of 16S rRNA. An unusual feature of this core element, which has been elucidated by NMR studies (Kalurachchi et al., (1 997) *Proc. Natl Acad. Sci USA* 94, 2139-2144), is the existence of a base triple element between nucleotides A595 and the A596/U644 base pair in the *E. coli* rRNA. The deletion of A595 severely impairs the binding of *E. coli* S8 (Mougel et al., (1993) *Eur J. Biochem*. 215, 787-792), indicating that this nucleotide is critical for RNA-protein recognition. Interestingly, this base triple is predicted by comparative phylogenetic evidence to be nearly universally-conserved in prokaryotes (Gutell (1993), *Nucleic Acids Res*. 21, 3051-3054).

While the S8-RNA interactions have been extensively characterized in *E. coli*, and the crystal structures of both *B. stearothermophilus* and *T. Thermophilus* S8 have been solved, prior to this invention very little was known regarding the structure and RNA-binding activities of ribosomal proteins from a pathogenic bacterial species. This problem is solved by the instant invention that provides cloned, expressed, and purified *Staphylococcus aureus* ribosomal protein S8, and RNA-binding studies showing a specific interaction between S8 and *S. aureus* or *E. coli* helix 21 RNAs. Mutagenesis studies also provided herein have defined nucleotides in the core RNA element from *S. aureus* that are essential for recognition by S8 and suggest a conservation of the structure of helix 21 in this organism. Also provided herein is a crystal structure of the native S8 protein from *S. aureus* to 1.56 Å resolution, and superimposition of this structure into the 30S ribosomal subunit structure of *T. thermophilus* has provided regions of contact with a cognate rRNA. Characterisation of *S. aureus* S8, taken together with a recent published crystal structure of the 30S ribosomal subunit (Wimberly et al., (2000) *Nature* 407, 327-339) advances understanding of bacterial ribosome architecture and allows for rational design of broad-spectrum antibiotics that target the translational apparatus.

The instant invention further provides a crystal structure of the protein S8 from the small ribosomal subunit of *Staphylococcus aureus* in its native state. A preferred structure shows that S8 presents two surfaces that are suited to bind a cognate rRNA. On of them is a α-helix that binds into the major groove of the double stranded rRNA. A second surface is one in which conserved residues are located and are critical for binding to a cognate rRNA. S8 interacts with rRNA through this second surface by an interaction that can be described as "riding" over the double helix. Given the significant role of S8 in organising and binding rRNA for proper ribosomal function and therefore proper protein synthesis, targeting either interaction between S8 and rRNA for disruption with small molecules could result in an effective antimicrobial.

SUMMARY OF THE INVENTION

In one aspect, the present invention relates to an S8 protein that is derived from *Staphylococcus aureus* and comprising a protein having the amino acid sequence shown in SEQ ID No. 1, and coordinates of Table 2 in an essentially pure native form or a homolog thereof.

In another aspect, the present invention provides a crystalline form of the *S. aureus* S8 rRNA-binding site as derived from models of S8 docked onto rRNA comprising coordinates of Table 2.

In yet another aspect, the invention provides structural coordinates of residues in a binding site responsible for binding of a rRNA.

In yet another aspect, the invention provides structural coordinates of a rRNA-binding-amino acid residues responsible for a function of S8 or involved in binding S8. The invention further provides a method for identifying inhibitors of an S8-rRNA interaction, which method comprises the steps of: providing coordinates of an S8 structure of the invention to a computerized modeling system; identifying compounds that will bind to the binding site; and screening the compounds identified for S8-rRNA binding inhibitory bio-activity.

Another aspect of this invention includes machine-readable media encoded with data representing the coordinates of the three-dimensional structure of the S8 crystal structure alone or in complex with RNA and/or DNA.

In another aspect of the invention provides a composition comprising a S8 rRNA-binding protein from a small ribosomal subunit of *Staphylococcus aureus* in crystalline form.

In a further aspect of the invention provides S8 protein derived from *Staphylococcus aureus* and comprising a protein having the coordinates of Table 2 in an essentially pure native form or a homolog thereof. Still further, an aspect of the invention provides a rRNA-binding mode of the protein S8 that is derived from *Staphylococcus aureus* and comprising a protein having the coordinates of Table 2. In yet another aspect, the invention provides a rRNA-binding function wherein said S8 protein has an rRNA-binding site formed by the amino acids 5-19 forming the N-terminal α-helix with nucleotides A820-A885, and the surface of S8 lined by residues 4-6, 30-32, 56-57, 82-92, 107-111, and 122-125 that interact with nucleotides A587-A758. Another aspect of the invention provides for a heavy atom derivative of a *Staphylococcus aureus* S8 protein crystal wherein a rRNA-binding function comprises a protein having the coordinates represented in FIGS. 1 and 7 to 14 and listed in Table 2.

In yet another aspect, the invention provides a process of identifying an inhibitor compound capable of inhibiting the rRNA-binding activity of a *Staphylococcus aureus* S8, said process comprising:

introducing into a suitable computer program information defining an rRNA-binding site conformation of a S8 inhibitor complex molecule comprising a conformation defined by the coordinates of the structures shown in FIGS. 1 and 7 to 14 and listed in Table 2 wherein said program displays the three-dimensional structure thereof;

creating a three dimensional structure of a test compound in said computer program;

displaying and superimposing the model of said test compound on the model of said rRNA-binding site;

assessing whether said test compound model fits spatially into the rRNA-binding site;

incorporating said test compound in a biological rRNA-binding assay for a activity characterized by said rRNA-binding site; and determining whether said test compound inhibits binding activity in said assay.

In yet another aspect, the invention provides a process of identifying an inhibitor compound capable of inhibiting rRNA-binding activity of a *Staphylococcus aureus* S8 according to claim 2, said process comprising:

carrying out an in vitro assay by introducing said compound in a biological rRNA-binding assay according to claim 2 and determining whether said test compound inhibits the ribosomal enzymatic activity or the rRNA-binding function in said assay.

In yet another aspect, the invention provides a product of the process of that is a peptide, peptidomimetic or synthetic molecule and is useful for inhibiting S8-rRNA binding in treatment of bacterial infections in a mammal. In another aspect, the invention provides a product that is a competitive or non-competitive inhibitor of a *Staphylococcus aureus* S8-rRNA binding activity.

In yet another aspect, the invention provides a process for determining a crystal structure form using structural coordinates of a *Staphylococcus aureus* S8 crystal or portions thereof, to determine a crystal form of a mutant, homologue or co-complex of said rRNA-binding function by molecular replacement.

In another aspect, the invention provides a process designing drugs useful for inhibiting *Staphylococcus aureus* S8 activity using atomic coordinates of a *Staphylococcus aureus* S8 to computationally evaluate a chemical entity for associating with a rRNA-binding site of a *Staphylococcus aureus* S8.

In yet another aspect, the invention provides a composition comprising a S8 rRNA-binding protein from the small ribosomal subunit of *Staphylococcus aureus* in orthorhombic crystalline form having a space group of $P2_12_12_1$.

A preferred aspect of the invention provides a composition wherein the crystalline form has lattice constants of a=42.1 Å, b=55.9 Å, c=61.3 Å, α=90.0°, β=90.0°, γ=90.0°.

Another preferred aspect of the invention provides a composition wherein a crystalline form contains one *Staphylococcus aureus* S8 molecule in a asymmetric unit.

In yet another aspect, of the invention provides a S8 protein composition wherein a S8 protein has an active site cavity formed by the amino acids S107, T108, S109, and E126. S8 protein composition is characterised by the coordinates selected from the group consisting of the coordinates of FIGS. 1 and 7 to 14 and Table 2.

Other aspects and advantages of the present invention are described further in the following detailed description of the preferred embodiments thereof.

DESCRIPTION OF THE FIGURES

FIG. 1 provides a representation of a secondary structural element crystal structure of a native S8 form *S. aureus*. The figures (a) and (b) depict views of S8 related by a rotation of 90° around a vertical axis. The ribbons represent α-helices and the arrows represent β-sheets.

FIG. 2 provides the purification of *S. aureus* ribosomal protein S8. Lane 1, markers (3.5, 6, 14.4, 21.5, 31, 36.5, 55, 66, 97, 116, 200 kDa, bottom to top, respectively); lane 2, uninduced cell pellet; lane 3, induced cell pellet; lane 4, total cell lysate; lane 5, soluble cell lysate; lane 6, solubilized cellpellet; lane 7, purified S8 protein.

FIG. 3 provides a filter-binding of *S. aureus* ribosomal protein S8 to wt and ΔA603 H21 RNA, 32P-RNAs were incubated with increasing amounts of *S. aureus* S8 on ice for 15 minutes, and then filtered and washed. Maximal binding was normalized to 100% in this experiment.

FIG. 4 provides sequence and predicted secondary strucuture of *S. aureus* helix 21 rRNA (nts 596-659)

FIG. 5 provides a diagrammatic representation of a S8-rRNA scintillation proximity assay.

FIG. 6. Scintillation proximity assay development. (a) SPA signal due to the biotinylated S8 interaction is detected when RNA and protein are incubated together. (b) The SPA signal is specific and represents biologically-relevant interactions between S8 and rRNA.

FIG. 7 provides a representation of critical residues involved in rRNA binding and their position relative to secondary structural elements in a crystal structure of native S8 form *S. aureus*. The two Figures (a) and (b) depict orthogonal view of the S8 protein.

FIG. 8 provides a representation of the model of S8 from *S. aureus* bound to rRNA via its "lower" or N-terminal surface. In the model, the rRNA is from a small ribosomal particle of *T. thermophilus*, *S. aureus* S8 was superimposed on a corresponding S8 from *T thermophilus*.

FIG. 9 provides a representation of a model of S8 from *S. aureus* bound to rRNA via the N-terminal α-helix. In the model, the helix binds to a major groove of a double stranded rRNA. The rRNA used in the model is from a small ribosomal particle of *T. thermophilus*, The figures (a) and (b) depict views related by a rotation of 90° around a vertical axis.

FIG. 10 provides a representation of a model of S8 from *S. aureus* bound to rRNA in an intact ribosomal particle. The model was created by superimposing a *S. aureus* S8 onto a homologous S8 in a *T. thermophilus* 30S ribosomal particle structure.

FIG. 12 provides a representation of a relative position of S8 (arrow) in a ribosomal particle (rRNA also indicated by arrows) as it is shown in the structure of a 30S ribosomal particle of *T. thermophilus*, where three tRNA molecules are bound. *S. aureus* S8 is expected to bind at the same relative position in the *S. aureus* ribosome. The Figures (a) and (b) are related by a 180° rotation about the vertical axis.

FIG. 13 provides a Model of *T. thermophilus* helix 21 rRNA binding to "underside" of *S. aureus* S8. S8 residues S107, T108, S109, and E126 make contacts with helix 21 nts A642, C643, and G644 (the highly-conserved base triple).

DETAILED DESCRIPTION OF THE INVENTION

Figure 11:
FIG. 11 provides a representation of a molecular surface of S8 from *S. aureus*. In the model, two surfaces come in contact with the rRNA, they are distinctly marked: the dense stippling (40%) surface corresponds to the N-terminal helix, and the less dense stippling (20%) surface corresponds to the surface located at the N-terminal side of the molecule.

The present invention provides a S8 from *Staphylococcus aureus* crystalline structure of the native enzyme.

S8 Protein From *Staphylococcus aureus* Crystalline Three-dimensional Structure.

Overall Structure

The crystal structures of S8 from *Staphylococcus aureus* in its native form has been determined and refined to 1.50 Å resolution. The final model includes residues 4-132 and a total of 281 water molecules as in FIG. 1. The polypeptide chain has an α+β fold divided in a somewhat defined two halves of the molecule: two α-helices and three β-strands form the N-terminal half of the molecule, and the C-terminal half is formed by a small helix and three short, anti-parallel strands. The N- and the C-terminus of molecule are located on opposite sides of the S8 molecule and the loop that connects the N- and C-terminal halves of the molecule protrudes into the solvent on the same side of the molecule as the C-terminus and opposite to the largest surface used by S8 to bind the rRNA.

rRNA Binding

Superposition of a *S. aureus* S8 onto a S8 of the S30 ribosomal subunit of *T thermophylus* (1FJG) indicates that there are two regions of interaction with the rRNA: the N-terminal helix formed by residues 5-19 inserts into a major groove of a double helix formed by nucleotides A820-A885. The second interacting surface is formed by residues 4-6, 30-32, 56-57, 82-92, 107-111, and 122-125 on the N-terminus side of a molecule that rides on a double helix formed by nucleotides A587-A758. Either of these two contact surfaces could be targets for small molecules that disrupt the interaction; which by affecting S8-rRNA interactions, ribosomal function would be impaired to the extent of being lethal for a bacterum.

Table 2 provides atomic coordinates of native crystal structures of S8 from *S. aureus*. The amino acid sequence of S8 from *S. aureus* is provided in SEQ ID No. 1. Small variations in the atomic coordinates shown in Table 2 will occur such as upon refinement of a crystal structure from a different crystal form that will result in a new set of coordinates. The deviation on Cα atoms from the present coordinate set is not expected to substantially exceed a rms of 2.5 Å. Similarly, bond angles and bond lengths will usually vary within a small range.(Engh, R. A., and Huber, R. (1991) *Acta Crystallogr*. A47, 392-400.), however, the inter-atomic interactions in Table 2 will remain constant, within the experimental error, as will the relative conformation and orientation or positioning of residues in the rRNA-binding site.

Mutants and Derivatives

The invention further provides homologues, co-complexes, mutants and derivatives of the S8 crystal structure of the invention.

The term "homologue" means a protein having at least 30% amino acid sequence identity with a functional domain of S8. Preferably the percentage identity will be 40, or 50%, more preferably 60 or 70% and most preferably 80 or 90%. A 95% identity is most particularly preferred.

The term "co-complex" means the S8 or a mutant or homologue of the S8 in covalent or non-covalent association with a chemical entity or compound.

The term "mutant" refers to the S8 polypeptide, i.e., a polypeptide displaying the biological activity of wild-type S8 activity, characterized by the replacement of at least one active-site amino acid from the wild-type sequence. Such a mutant may be prepared, for example, by expression of the S8 rRNA-binding protein cDNA previously altered in its coding sequence by oligonucleotide-directed mutagenesis.

S8 mutants may also be generated by site-specific incorporation of unnatural amino acids into the S8 protein using the general biosynthetic method of C. J. Noren et al, *Science*, 244: 182-188 (1989). In this method, the codon encoding the amino acid of interest in wild-type S8 is replaced by a "blank" nonsense codon, TAG, using oligonucleotide-directed mutagenesis. A suppressor directed against this codon is then chemically aminoacylated in vitro with the desired unnatural amino acid. The aminoacylated residue is then added to an in vitro translation system to yield a mutant S8 protein with the site-specific incorporated unnatural amino acid.

Selenocysteine or selenomethionine may be incorporated into wild-type or mutant S8 protein by expression of S8-encoding cDNAs in auxotrophic *E. coli* strains (W. A. Hendrickson et al, EMBO J., 9 (5): 1665-1672 (1990)) or a normal strain grown in a medium supplemented with appropriate nutrients that will prevent endogenous synthesis of methionine. In either of these methods, the wild-type or mutated undecaprenyl pyrophosphate synthase cDNA may be expressed in a host organism on a growth medium depleted of either natural cysteine or methionine (or both) but enriched in selenocysteine or selenomethionine (or both).

The term "heavy atom derivative" refers to derivatives of S8 produced by chemically modifying a crystal of S8. In practice, a native crystal is treated by immersing it in a solution containing the desired metal salt, or organometallic compound, e.g., lead chloride, gold thiomalate, thimerosal or uranyl acetate, which upon diffusion into the protein crystal can bind to the protein. The location of the bound heavy metal atom site(s) can be determined by X-ray diffraction analysis of the treated crystal. This information, in turn, is used to generate the phase angle information needed to construct a three-dimensional electron density map from that a model of the atomic structure of the enzyme is derived (T. L. Blundel and N. L. Johnson, *Protein Crystallography*, Academic Press (1976)).

The term "space group" refers to the arrangement of entities (i.e. molecules) throughout the crystal lattice. There are only 132 possible arrangements, each one unique and identified by a symbol. The space group symbol is formed by a letter (P, F, I, C) and numbers with or without subscripts, for example: $P2_1$, $I222$, $C2_12_12_1$, etc.

Methods of Identifying Inhibitors of the S8 From *Staphylococcus aureus* Crystalline Structure Another aspect of this invention involves a method for identifying inhibitors of S8 protein characterized by the crystal structure described herein, and the inhibitors themselves. The S8 crystal structure of the invention permits the identification of inhibitors of the rRNA-binding activity of a *Staphylococcus aureus* S8. Such inhibitors may bind to all or a portion of the active site of the S8; or even be competitive, non-competitive, or uncompetitive inhibitors. Once identified and screened for biological activity, these inhibitors may be used therapeutically or prophylactically to block the rRNA-binding activity of a *Staphylococcus aureus* S8, and thus, inhibit proper assembly of the small ribosomal subunit.

One design approach is to probe the S8 crystal of the invention with molecules composed of a variety of different chemical entities to determine optimal sites for interaction between candidate inhibitors and the rRNA-binding activity of S8. For example, high resolution X-ray diffraction data collected from crystals soaked in or co-crystallized with other molecules allows the determination of where each type of solvent molecule sticks. (J. Travis (1993) *Science*, 262: 1374). Molecules that bind tightly to those sites can then be further modified and synthesized and tested for the ability to inhibit rRNA-binding activity of S8.

The time-dependent analysis of structural changes in S8 protein during its interaction with other molecules is permitted. The reaction intermediates of S8 protein can also be deduced from the reaction product in co-complex with S8 protein. Such information is useful to design improved analogues of S8 protein inhibitors or to design classes of inhibitors based on the reaction intermediates of the S8 protein and binding activity of S8 inhibitor co-complex. This provides a novel route for designing S8 inhibitors with both high specificity and stability.

Another approach made possible by this invention, is to screen computationally small molecule data bases for chemical entities or compounds that can bind in whole, or in part, to the S8 protein. In this screening, the quality of fit of such entities or compounds to the binding site may be judged either by shape complementarity or by estimated interaction energy (E. C. Meng et al, *J. Comp. Chem.*, 13:505-524 (1992)).

Because S8 may crystallize in more than one crystal form, the structure coordinates of S8, or portions thereof, as provided by this invention are particularly useful to solve the structure of those other crystal forms of S8. They may also be used to solve the structure of S8 mutants, S8 co-complexes, or of the crystalline form of any other protein with significant amino acid sequence homology to any functional domain of S8.

One method that may be employed for this purpose is molecular replacement. In this method, the unknown crystal structure, whether it is another crystal form of S8, an S8 mutant, or an S8 co-complex, or the crystal of some other protein with significant amino acid sequence homology to any functional domain of S8, may be determined using the S8 structure coordinates of this invention as provided in Table 2. This method will provide an accurate structural form for the unknown crystal more quickly and efficiently than attempting to determine such information ab initio.

Thus, the S8 structure provided herein permits the screening of molecules and/or the designing of new molecules that bind to the S8 protein structure, particularly at the active site, via the use of computerized evaluation systems. For example, computer modelling systems are available in that the sequence of the S8, and the S8 structure (i.e., atomic coordinates of S8 and/or the atomic coordinate of the active site cavity, bond angles, dihedral angles, distances between atoms in the active site region, etc. as provided by Table 2 herein) may be input. Thus, a machine readable medium may be encoded with data representing the coordinates of Table 2. The computer then generates structural details of the site into that a test compound should bind, thereby enabling the determination of the complementary structural details of said test compound.

More particularly, the design of compounds that bind to or inhibit S8 according to this invention generally involves consideration of two factors. First, the compound must be capable of physically and structurally associating with the S8 protein. Non-covalent molecular interactions important in the association of S8 protein with its ligands include hydrogen bonding, van der Waals and hydrophobic interactions.

Second, the compound must be able to assume a conformation that allows it to associate with S8 protein. Although certain portions of the compound will not directly participate in this association of an S8 protein, those portions may still influence the overall conformation of the molecule. This, in turn, may have a significant impact on potency. Such conformational requirements include the overall three-dimensional structure and orientation of the chemical entity or compound in relation to all or a portion of the binding site, e.g., active site or accessory binding site of S8 protein, or the spacing between functional groups of a compound comprising several chemical entities that directly interact with S8, such as rRNA.

The potential inhibitory or binding effect of a chemical compound on S8 may be analyzed prior to its actual synthesis and testing by the use of computer modelling techniques. If the theoretical structure of the given compound suggests insufficient interaction and association between it and S8, synthesis and testing of the compound is obviated. However, if computer modelling indicates a strong interaction, the molecule may then be synthesized and tested for its ability to bind to S8 and inhibit using a suitable assay. In this manner, synthesis of inoperative compounds may be avoided.

An inhibitory or other binding compound of S8 may be computationally evaluated and designed by means of a series of steps in that chemical entities or fragments are screened and selected for their ability to associate with the individual binding pockets or other areas of S8 protein.

One skilled in the art may use one of several methods to screen chemical entities or fragments for their ability to associate with S8 and more particularly with the individual binding pockets of the S8 active site or accessory binding site. This process may begin by visual inspection of, for example, the active site on the computer screen based on the S8 coordinates in Table 2. Selected fragments or chemical entities may then be positioned in a variety of orientations, or docked, within a binding pocket of S8. Docking may be accomplished using software such as Quanta and Sybyl, followed by energy minimization and molecular dynamics with standard molecular mechanics forcefields, such as CHARMM and AMBER.

Specialized computer programs may also assist in the process of selecting fragments or chemical entities. These include:

1. GRID (P. J. Goodford, "A Computational Procedure for Determining Energetically Favorable Binding Sites on Biologically Important Macromolecules", *J. Med. Chem.*, 28:849-857 (1985)). GRID is available from Oxford University, Oxford, UK.

2. MCSS (A. Miranker and M. Karplus, "Functionality Maps of Binding Sites: A Multiple Copy Simultaneous Search Method", *Proteins: Structure, Function and Genetics*, 11:29-34 (1991)). MCSS is available from Molecular Simulations, Burlington, Mass.

3. AUTODOCK (D. S. Goodsell and A. J. Olsen, "Automated Docking of Substrates to Proteins by Simulated Annealing", *Proteins: Structure, Function, and Genetics*, 8:195-202 (1990)). AUTODOCK is available from Scripps Research Institute, La Jolla, Calif.

4. DOCK (I. D. Kuntz et al., "A Geometric Approach to Macromolecule-Ligand Interactions", J. Mol. Biol., 161: 269-288 (1982)). DOCK is available from University of California, San Francisco, Calif.

Additional commercially available computer databases for small molecular compounds includes Cambridge Structural Database, Fine Chemical Database, and CONCORD, for a review see Rusinko, A., Chem. Des. Auto. News 8, 44-47 (1993).

Once suitable chemical entities or fragments have been selected, they can be assembled into a single compound or inhibitor. Assembly may be proceed by visual inspection of the relationship of the fragments to each other on the three-dimensional image displayed on a computer screen in relation to the structure coordinates of S8 protein. This would be followed by manual model building using software such as Quanta or Sybyl.

Useful programs to aid one of skill in the art in connecting the individual chemical entities or fragments include:

1. CAVEAT (P. A. Bartlett et al, "CAVEAT: A Program to Facilitate the Structure-Derived Design of Biologically Active Molecules", in Molecular Recognition in Chemical and Biological Problems", Speical Pub., Royal Chem. Soc. 78, pp. 182-196 (1989)]. CAVEAT is available from the University of California, Berkeley, Calif.

2. 3D Database systems such as MACCS-3D (MDL Information Systems, San Leandro, Calif.). This area is reviewed in Y. C. Martin, "3D Database Searching in Drug Design," J. Med. Chem., 35:2145-2154 (1992).

3. HOOK (available from Molecular Simulations, Burlington, Mass.).

Instead of proceeding to build an S8 protein inhibitor in a step-wise fashion one fragment or chemical entity at a time as described above, inhibitory or other S8 binding compounds may be designed as a whole or "de novo" using either an empty active site or optionally including some portion(s) of a known ligand(s). These methods include:

1. LUDI (H. J. Bohm, "The Computer Program LUDI: A New Method for the De Novo Design of Enzyme Inhibitors", *J. Comp. Aid. Molec. Design*, 6:61-78 (1992)). LUDI is available from Biosym Technologies, San Diego, Calif.

2. LEGEND (Y. Nishibata and A. Itai, *Tetrahedron*, 47:8985 (1991)). LEGEND is available from Molecular Simulations, Burlington, Mass.

3. LEAPFROG (available from Tripos Associates, St. Louis, Mo.).

Other molecular modelling techniques may also be employed in accordance with this invention. See, e.g., N. C. Cohen et al, "Molecular Modeling Software and Methods for Medicinal Chemistry", *J. Med. Chem.*, 33:883-894 (1990). See also, M. A. Navia and M. A. Murcko, "The Use of Structural Information in Drug Design", *Current Opinions in Structural Biology*, 2:202-210 (1992). For example, where the structures of test compounds are known, a model of the test compound may be superimposed over the model of the structure of the invention. Numerous methods and techniques are known in the art for performing this step, any of which may be used. See, e.g., P. S. Farmer, Drug Design, Ariens, E. J., ed., Vol. 10, pp 119-143 (Academic Press, New York, 1980); U.S. Pat. No. 5,331,573; U.S. Pat. No. 5,500, 807; C. Verlinde, *Structure*, 2:577-587 (1994); and I. D. Kuntz, *Science*, 257:1078-1082 (1992). The model building techniques and computer evaluation systems described herein are not a limitation on the present invention.

Thus, using these computer evaluation systems, a large number of compounds may be quickly and easily examined and expensive and lengthy biochemical testing avoided. Moreover, the need for actual synthesis of many compounds is effectively eliminated.

In another aspect, the S8 structure of the invention permit the design and identification of synthetic compounds and/or other molecules that have a shape complimentary to the conformation of the S8 active site of the invention. Using known computer systems, the coordinates of the S8 structure of the invention may be provided in machine readable form, the test compounds designed and/or screened and their conformations superimposed on the structure of the invention. Subsequently, suitable candidates identified as above may be screened for the desired S8 inhibitory bioactivity, stability, and the like.

Once identified and screened for biological activity, these inhibitors may be used therapeutically or prophylactically to block rRNA-binding activity of S8, and thus, inhibit proper assembly of the small ribosomal subunit.

As used herein the term "natural product molecule" includes all non-synthetic products of nature and includes, but is not limited to, derivatives, extracts or homologs thereof, having, or containing, a bioactive component.

Another aspect of this invention involves a method for identifying inhibitors of a S8 characterized by the crystal structure and rRNA-binding site described herein. The S8 from *S. aureus* crystalline structure of the invention permits the identification of inhibitors of ribosomal function. Such inhibitors may be competitive, binding to all or a portion of the rRNA-binding site of the S8; or non-competitive and bind to and inhibit ribosomal assembly or function whether or not it is bound to another chemical entity.

One design approach is to probe the S8 crystal of the invention with molecules composed of a variety of different chemical entities to determine optimal sites for interaction between candidate S8 inhibitors and the protein. For example, high resolution X-ray diffraction data collected from crystals saturated with solvent allows the determination of where each type of solvent molecule binds. Small molecules that bind tightly to those sites can then be designed and synthesized and tested for their S8 inhibitor activity.

This invention also enables the development of compounds that can isomerize to short-lived reaction intermediates in the chemical reaction of a substrate or other compound that binds to or with the S8. Thus, the time-dependent analysis of structural changes in the S8 during its interaction with other molecules is permitted. The reaction intermediates of the S8 can also be deduced from the reaction product in co-complex with the S8. Such information is useful to design improved analogues of known S8 inhibitors or to design classes of inhibitors based on the reaction intermediates of the S8-rRNA and S8 inhibitor co-complex. This provides a route for designing S8 inhibitors with both high specificity and stability.

Another approach made possible by this invention is to screen computationally small molecule databases for chemical entities or compounds that can bind in whole, or in part, to the S8 protein. Details on this process and the results it can provide are now documented in the art. For a description of this type of technology please refer to PCT application WO 97/16177 published 09 May 1997; the techniques described there for computer modeling are incorporated herein by reference.

Once identified by the modeling techniques, the inhibitor of ribosomal function may be tested for bio-activity using standard techniques. For example, the structure of the invention may be used in activity assays to determine the inhibitory activity of the compounds or binding assays using conventional formats to screen inhibitors. One particularly suitable assay format includes the enzyme-linked immunosorbent assay (ELISA). Other assay formats may be used; these assay formats are not a limitation on the present invention.

In another aspect, the S8 structure of the invention permit the design and identification of synthetic compounds and/or other molecules that are characterized by the conformation of the S8 of the invention. Using known computer systems, the coordinates of the S8 structure of the invention may be provided in machine readable form, the test compounds designed and/or screened and their conformations superimposed on the structure of the S8 of the invention. Subsequently, suitable candidates identified as above may be screened for the desired inhibitory bio-activity, stability, and the like.

Once identified and screened for biological activity, these inhibitors may be used therapeutically or prophylactically to block S8 function, and thus, overcome bacterial resistance to antibiotics, for example, of the beta-lactam class, eg. imipenem, penicillins, cephalosporins, etc. by using an entirely different mechanism of attacking bacteria in diseases produced by bacterial infection.

The following examples illustrate various aspects of this invention. These examples do not limit the scope of this invention that is defined by the appended claims.

EXAMPLE 1

The Expression and Purification of the S8 From *Staphylococcus aureus* in *Escherichia coli*

The gene for *S. aureus* S8 was PCR amplified from strain WCUH29 genomic DNA, and the resulting fragment was cloned into pET28a(+) for expression in *E. coli*. The *S. aureus* S8-expression construct (S8sa-pET28) was transformed into BL21(DE3) cells for expression and purified by cation exchange chromatography. The soluble polypeptide includes 132 amino acid residues with a molecular weight of 14,830 Da. This product was greater than 95% pure by SDS PAGE, has the desired RNA-binding activity, and N-terminal amino acid analysis confirmed its identity. A one liter culture of *E. coli* haboring the S8 expression construct was induced with IPTG for three hours at 37° C. FIG. 2 shows that very little of the overexpressed protein was present in the soluble fraction (lane 5). After solubilization of the protein in 6M urea and purification by anion exchange chromatography, the resulting protein appeared to be greater than 95% pure. N-terminal sequencing, MALDI-MS and AA analysis all confirmed the identity of the purified protein.

1.A. Measurement of S8 Activity.

It is also possible to define ligand interactions with S8 in experiments that are not dependent upon enzyme catalyzed turnover of substrates. This type of experiment can be done in a number of ways:

1.B.1. Effects of Ligand Binding Upon Intrinsic Fluorescence (e.g. of Tryptophan).

Binding of either natural ligands or inhibitors may result in the protein's conformational changes that alter its fluorescence. Using stopped-flow fluorescence equipment, this can be used to define the microscopic rate constants that describe binding. Alternatively, steady-state fluorescence titration methods can yield the overall dissociation constant for binding in the same way that these are accessed through enzyme inhibition experiments.

EXAMPLE 2

Crystallization, Structure Determination and Refinement of the Crystal Structure of the S8 from *S. aureus*

2.A. Crystallization

Single crystals of native S8 grew from sitting drops prepared by mixing 2 μL protein with 2 μL of reservoir solution containing 30% PEG4000, 0.2M $Li_2SO_4$, 0.1M Tis-HCl, pH 8.5. The drops were left to equilibrate at room temperature against 500 μL of the reservoir solution. By registering the position and intensity of many tens of thousands of diffraction spots using the computer program HKL2000 (Otwinowski, Z. and Minor, W. (1996) *Methods in Enzymology* 276, 307-326) and, program MOSFLM (A. G. W. Leslie, MRC Laboratory of Molecular Biology, Hills Road, Cambridge, UK and Collaborative Computational Project, Number 4, (1994) *Acta Cryst*. D50, 760-763.) the crystal has been determined to be the orthorhombic space group $P2_12_12_1$ and have unit cell parameters (lattice constants): a=42.1 Å, b=55.9 Å, c=61.3 Å, alpha=beta=gamma=90.0° and one molecule in the asymmetric unit.

2.B. X-ray Diffraction Data Collection

The crystal was picked up with a loop and frozen by quickly submerging it into liquid nitrogen before mounting it under the cold stream. Diffraction data was collected at CHESS F2 beamline using 1.000 Å wavelength x-rays and the ADSC QuantumIV detector. The data was integrated, reduced and scaled with DPS/MOSFLM/SCALA (CCP4). The data collection statistics are shown in Table 3.

2.C. Structure Determination

The structure was determined by molecular replacement using the program AmoRe (Navaza). and the atomic coordinates of the S8 structure from *B. stearothermophylus* (1SEI). The solution had a correlation coefficient of 0.50 and R=0.49. The correct amino acid sequence was traced before refinement. The suite of programs CNX was used for the refinement and the interactive graphics program O was used for manipulating the model. The final model includes residue 4 to 132 and 281 water molecules. Residues 1 to 3 are not visible in the electron density map.

2.D. Model Building and Refinement

The electron density map was of high quality and afforded the placement of the complete molecule using the interactive computer graphics program O (Jones, T. A. et al. (1991) *Acta Crystallogr*. A47: 110-119). The model was refined against diffraction data by successive rounds of simulated annealing with torsion angle dynamics, positional refinement and restrained B-factor refinement using CNX (A. Brunger et al., *Science*, 235: 458-460 (1987)) followed by manual intervention. The refinement and manual rebuilding was monitored by the quality of the 2Fo-Fc and Fo-Fc electron density maps and the value of the crystallographic R and $R_{free}$. The final R is 0.19 and the $R_{free}$ is 0.23 for 23,473 reflections to 1.50 Å resolution. The rms deviation from the reference bond lengths and bond angles (Engh & Huber (1991) *Acta Crystallogr*. A47: 392-400) are 0.017 Å and 1.8°, respectively. The refined model includes residues 4-132 according to the amino acid sequence SEQ ID NO:1. The N-terminal residues 1 to 3 were disordered in the four molecules. In the refined model, all the main chain conformations fall in the "allowed" regions of the Ramachandran plot. The refinement statistics are shown in Table 4.

EXAMPLE 3

Identifying Inhibitors of Activity of the *S. aureus* S8 Protein

Avi-tagged S8 was expressed in *E. coli* along with with BirA (biotin ligase), and LC/MS indicated that approximately 50% of the S8 contained the biotin group at the N-terminus (data not shown). RNA filter-binding studies established that the biotinylated Avi-tagged S8 protein recognized Helix 21 rRNA with an affinity comparable to the untagged protein, Table 5, indicating that the peptide tag and subsequent labeling have no adverse effect on RNA-protein recognition. This biotinylated protein was then used to develop a high throughput-screening assay, which will be used to detect inhibitors of the S8-rRNA interaction. The basis of the scintillation proximity assay is shown in FIG. 5. Essentially, the Helix 21 rRNA fragment is labeled with $^{33}$P or $^{3}$H (either internally or at the -3' or 5'-ends), and a complex is allowed to form with the biotinylated S8 protein. After formation of the RNA-protein complex, streptavidin SPA beads (Amersham Pharmacia) are added and incubated with the RNA-protein complex, and the samples are read in a microplate scintillation counter (eg, TopCount by Packard). Using biotinylated (Avi-tagged) *S. aureus* ribosomal protein S8, $^{33}$P-labeled helix 21 RNA, and streptavidin SPA beads, a specific signal due to protein-RNA binding was detected, FIG. 6(*a*). When Helix 21 ΔA649 substrate was used in the SPA assay, no signal above background could be detected, indicating the validity of the SPA format as a viable assay to examine S8-rRNA interactions, FIG. 6(*b*). The specificity of S8-rRNA recognition was further validated in the SPA format by titrating the binding reactions with unlabeled cognate and non-cognate RNAs. Results show that the addition of excess, unlabeled, wild-type Helix 21 RNA competes the SPA signal to near background levels, while the addition of like amounts of Helix 21 ΔA649 RNA does not (data not shown). This further indicates that the SPA format reflects true recognition of 16S rRNA by S8 protein. This assay can be transferred to a multi-well format (example, 96- or 384-well microplates) for high throughput screening of diverse compound collections. Such compounds that inhibit the S8-rRNA interaction may be useful anti-bacterials.

3.A. Cloning of *S. aureus* S8

The gene for *S. aureus* S8 was PCR amplified from strain WCUH29 genomic DNA using a forward primer containing a BspHI site (5'-ACTTC CTCATGACAATGACAGATC-CAATCG-3') (SEQ ID NO: 3) and a reverse primer containing a HindIII site (5'-CTTCTCAAGCTTTTAC-CAAACGTATGCGATAA-3') (SEQ ID NO: 4). The 419bp fragment was digested with BspHI and HindIII, purified, and ligated into pET28a(+) cut with NcoI and HindIII. Positive transformants were confirmed by sequencing.

3.B. pET24-AviTag Vector Construction

A linker was made encoding the AviTag (Avidity, see below) with an NdeI 5' overhang, 3' BamHI overhang and containing a unique ScaI site after the tag. This was ligated into pET24b(+) from Novagen cut with NdeI and BamHI.

```
5'T ATG GCT GGT GGC CTG AAC GAT ATT TTC GAA GCT CAG      (SEQ ID NO: 5)
3'   AC CGA CCA CCG GAC TTG CTA TAA AAG CTT CGA GTC      (SEQ ID NO: 6)
     M   A   G   G   L   N   D   I   F   E   A   Q      (SEQ ID NO: 7)

AAA ATC GAA TGG CAT GAA AGT ACT G   3'
TTT TAG CTT ACC GTA CTT TCA TGA C CTA G 5'
 K   I   E   W   H   E   S
                                 60
```

3.C. Cloning of AviTag-S8 Construct

The intact *S. aureus* S8 gene was PCR amplified from WCUH29 genomic DNA using Pwo polymerase (Roche) and the following primers: forward (5'-ATGACAATGACA-GATCCAATCGC-3') (SEQ ID NO: 8) and reverse (5'-TTTACCAAACGTATGCGATAATTTC-3') (SEQ ID NO:

9). The 400 bp fragment was kinased and ligated into pET24-AviTag digested with ScaI and dephosphorylated. The construct was confirmed by sequencing and transformed into BL21 (DE3) cells containing pACYCbirA (Avidity) for expression of the biotinylated-AviTag-S8.

3.D. Protein Expression and Purification

The *S. aureus* S8-expression construct (S8sa-pET28) was transformed into BL21(DE3) cells for expression and a 10 ml overnight culture in LB, 50 ug/ml Kanamycin, 1% glucose was diluted 1:100 and grown to an $OD_{600}$ of 0.55. IPTG was added to 0.5 mM and induction carried out for 3 h at 37° C. Cells were lysed in 30ml (5 ml/g wet weight) of 50 mM Na-phosphate pH 7.5 and lysed via sonication and freeze/thaw. After centrifugation, the pellet was solubilized in 30 ml of 6M Urea/20 mM Tris pH 7.0 (Buffer A) and the filtered supernatant applied to a 5 ml HiTrap SP column. S8 was eluted with a 40 column volume gradient of 0-1M NaCl in Buffer A. Fractions containing S8 were pooled and refolded by dialysis against several changes of 80 mM Hepes pH 7.6 and 1M KCl. Aliquots were frozen in a dry ice/ethanol bath and stored at −80° C. Integrity of the protein was confirmed by N-terminal sequencing, MALDI-MS and AA analysis. Yield from the 1 liter culture was 36 mg of purified protein.

3.E. Expression and Purification of B-Avi-S8

5 ml of an overnight LB/Kanamycin (50 ug/ml)/Chloramphenicol (34 ug/ml)/1% glucose culture was diluted 100-fold into media containing 50 uM biotin. The culture was grown at 37° C./250 rpm to an $OD_{600}$ of 0.5, IPTG was added to 0.5 mM and growth continued at 37° C. for an additional 3 h. Pelleted cells were homogenized in 6M Urea/20 mM Tris pH7.0 (BufferA) in a volume of 5 ml/g cells. Clarified lysate was applied to a 5 ml HiTrapSP column (Amersham Pharmacia) and eluted with a 40 column volume gradient of 0-1M NaCl in BufferA. Fractions containing B-Avi-S8 were pooled and dialized at 4° C. against 80 mM Hepes pH 7.6/1M KCl. Aliquots were quick-frozen and stored at −80° C. N-terminal sequencing, LC/MS and AA analysis confirm the integrity of the protein. Yield was 14 mg of greater than 90% purity from a 500 ml culture with ~50% biotinylation.

3.F. Cloning and Transcription of Helix 21 rRNAs

A DNA fragment corresponding to Helix 21 (nts 584-655) of *E. coli* 16S rRNA was amplified by PCR of *E. coli* genomic DNA. A T7-promoter sequence was incorporated into the fragment by the 5'-primer, and the fragment was cloned into the EcoRI-KpnI sites of pUC19 to generate pUC-EcH21. Helix 21 from *Staphylococcus aureus* (corresponding to nts 596-659 of 16S rRNA) was cloned downstream of a T7 promoter in a similar manner to generate the plasmid pUC-SaH21. The generation of mutant derivatives of *S. aureus* Helix 21 was done by incorporation of site directed mutagenesis of PCR primers. Unlabeled RNAs were trancribed from BamHI-linearized DNA templates using MEGAshortscript kit (Ambion Inc., Austin, Tex.). RNA substrates for filter-binding studies were made by end-labeling with $\gamma$-$^{32}$P or $^{33}$P-ATP.

3.G. Filter-binding

For filter-binding experiments, labeled RNAs were renatured by preincubation in binding buffer (80 mM HEPES-KOH pH 7.6, 350 mM KOAc, 20 mM MgOAc) for fifteen minutes at 40° C. Renatured RNA was then mixed with the appropriate amount of protein and then incubated for fifteen minutes on ice and then filtered immediately on 0.45 μM nitrocellulose filters (Whatman), washed with 1.0 ml of binding buffer, and then counted in a scintillation counter. $K_d$'s were determined from several independent binding experiments for each substrate RNA.

3.H. Characterisation of the RNA-binding Activity of *S. aureus* S8

In order to characterise the RNA-binding activity of *S. aureus* S8, an RNA-filter-binding assay was developed. The results of these experiments, shown in FIG. 3, demonstrate that the interaction of S8 with wild-type Helix 21 RNA has a measured affinity of approximately 400 nM. This interaction is highly specific, in that an RNA containing a deletion of A603 fails to demonstrate any appreciable binding by S8. This result also highlights the importance of the base triple within helix 21, as A603 is predicted to interact with the A604-U652 basepair.

Several mutations were introduced into Helix 21 rRNA, shown in FIG. 4, and the apparent dissociation constants for the interaction of S8 and these variant RNA substrates was examined. These results are shown in Table 5. Substitution of the A-U base pair (nts 604-652) with G-C result in a tenfold decrease in binding affinity. This nucleotide substitution is predicted to maintain the stem structure in this region but it changes the primary sequence of the RNA. Since S8 still binds to this RNA, albeit at a tenfold decreased affinity, this underscores the fact that while maintenance of the secondary structure in this region is required, the exact sequence of the RNA is necessary for optimal recognition by S8. Deletion of A649, and substitutions of C651-U and A650C651-U all result in the complete abrogation of binding by S8, suggesting the critical importance of nucleotides in this region. The conserved nature of this RNA-protein recognition is further demonstrated by the fact that *S. aureus* S8 can recognize *E. coli* Helix 21 rRNA with a similar affinity as with *S. aureus* Helix 21 rRNA.

EXAMPLE 4

Modeling Studies of *S. aureus* S8-rRNA Binding

Superposition of the *S. aureus* S8 onto the S8 in the S30 ribosomal subunit of *T. thermophilus* (1FJG), shown in FIG. 12(*a*), indicates that there are two regions of interaction with the rRNA: residues 5-19 (N-terminal α-helix) with nucleotides A820-A885 and residues 4-6, 30-32, 56-57, 82-92, 107-111, and 122-125 with nucleotides A587-A758. This second RNA-interacting face is in direct contact with bases and more likely the surface to target with inhibitors that disrupt the S8-rRNA interaction(s).

Figure 14A:
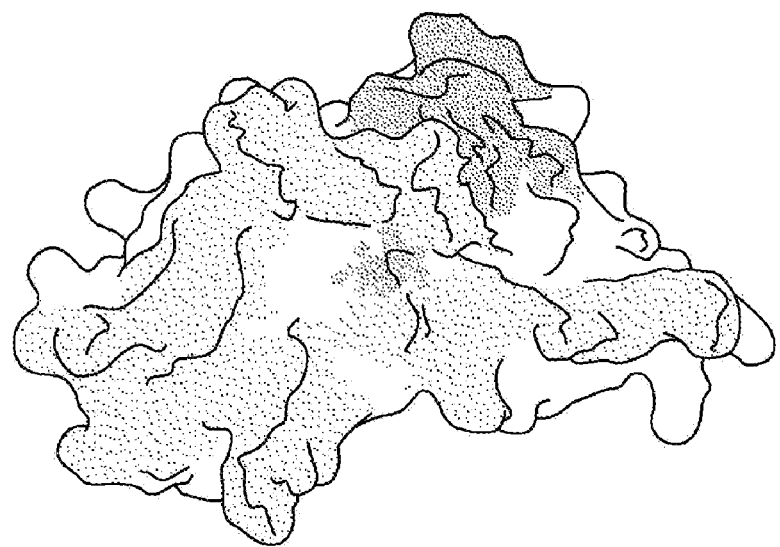
FIG. 14 provides a surface representation of N-terminal region of *S. aureus* S8. (a) N-terminus (marked with less dense stippling (20%)) is predicted to bind to rRNA in *T. thermophilus* 30S ribosomal subunit. (b) The surface electrostatic potential is depicted.
Figure 14B:
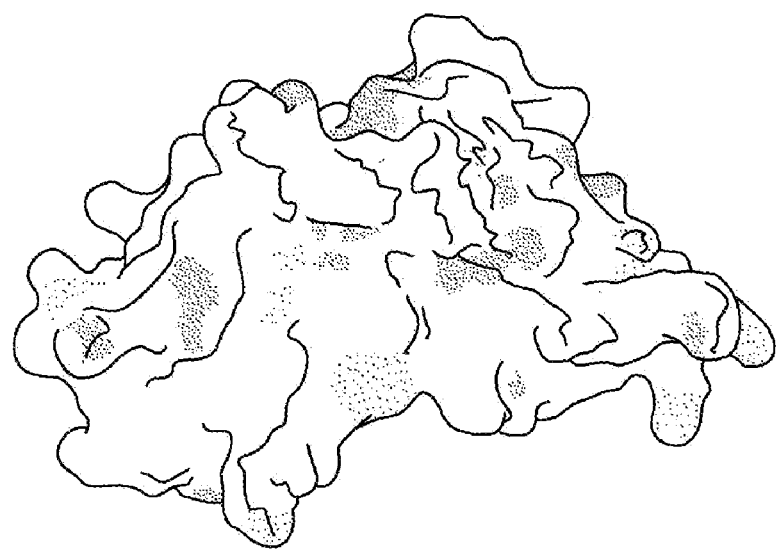

The surface representation of *S. aureus* S8 protein is shown in FIG. 14(*a*). The N-terminus, marked with less dense stippling (20%), is the region predicted to bind to rRNA in *T. thermophylus* S30 ribosomal particle and presumably also in *S. aureus* where it rides on the rRNA formed by a double stranded stem structure formed by nucleotides A587 to A758 in 1FJG. In FIG. 14(*b*), the calculated surface electrostatic potential shows that the S8-rRNA interactions are not predominantly electrostatic. In this interacting surfaces there appears to be cavities between protein and the rRNA that may accommodate drug(s) that could interfere with the normal S8-rRNA interaction.

FIG. 13 shows a model of *T. thermophilus* helix 21 rRNA binding to the "underside" of *S. aureus* S8. S8 residues S107, T108, S109, and E126 make contacts with helix 21 nts A642, C643, and G644 (the highly-conserved base triple). This modeling data is consistent with the biochemical data showing that nucleotides in this base triple are critical for accurate recognition by *S. aureus* S8 as shown in Table 5.

TABLE 1

| E. coli | H. influenzae | P. aeruginosa | M. catarrhalis | S. aureus | B. subtilis | S. pneumoniae | S. pyogenes | E. faecalis | Human | |
|---|---|---|---|---|---|---|---|---|---|---|
| 100 | 84 | 62 | 58 | 48 | 47 | 47 | 45 | 47 | 23 | E. coli |
|  | 100 | 62 | 63 | 45 | 45 | 45 | 45 | 45 | 22 | H. influenzae |
|  |  | 100 | 56 | 43 | 46 | 45 | 42 | 45 | 24 | P. aeruginosa |
|  |  |  | 100 | 46 | 46 | 45 | 46 | 47 | 23 | M. catarrhalis |
|  |  |  |  | 100 | 77 | 74 | 78 | 77 | 22 | S. aureus |
|  |  |  |  |  | 100 | 77 | 72 | 77 | 81 | 27 | B. subtilis |
|  |  |  |  |  |  | 100 | 91 | 80 | 29 | S. pneumoniae |
|  |  |  |  |  |  |  | 100 | 84 | 26 | S. pyogenes |
|  |  |  |  |  |  |  |  | 100 | 27 | E. faecalis |
|  |  |  |  |  |  |  |  |  | 100 | Human |

TABLE 3

Data collection statistics

| Resolution, Å | Complete, % | Multiplicity | I/σ<I> | $R_{sym}$ |
|---|---|---|---|---|
| 4.74 | 95.8 | 2.7 | 14.6 | 0.040 |
| 3.35 | 99.3 | 3.0 | 17.2 | 0.035 |
| 2.74 | 99.8 | 3.1 | 14.6 | 0.037 |
| 2.37 | 99.9 | 3.2 | 11.9 | 0.051 |
| 2.12 | 99.9 | 3.2 | 9.1 | 0.068 |
| 1.94 | 100.0 | 3.2 | 8.3 | 0.077 |
| 1.79 | 100.0 | 3.2 | 5.8 | 0.115 |
| 1.68 | 100.0 | 3.2 | 4.3 | 0.155 |
| 1.58 | 99.7 | 3.1 | 3.1 | 0.213 |
| 1.50 | 97.5 | 2.7 | 2.5 | 0.274 |
|  | 99.4 | 3.1 | 8.4 | 0.053 |

TABLE 4

Refinement statistics

| | |
|---|---|
| Resolution | 20-1.5Å |
| No. Reflections | 23,473 |
| Completeness | 99.2% |
| R | 0.19 |
| $R_{free}$ | 0.23 |
| No. protein atoms | 1049 |
| No. solvent atoms | 281 |
| rms deviation from ideal: | |
| bond length | 0.017Å |
| bond angle | 1.8° |

Table 2. Atomic Coordinates of the Native S8 Structure (SEQ ID NO:1)

Legend:

1. Under the heading ATOM appears a "atom number" (e.g. 1,2,3,4 . . . etc) and the "atom name" (e.g. CA, CB, N, . . . etc) such that to each "atom name" in the coordinate list corresponds an "atom number".

2. Under the heading RESIDUE appears a three-letter "residue name" (e.g THR, ASP, etc), a "chain identifier" represented by a capital letter (e.g. A, B, C D, etc) and a "residue number", such that to each residue (or amino acid) in the amino acid sequence of the particular protein in the structure corresponds a name that identifies it, a number according to its position along the amino acid sequence, and a chain name. The chain name identifies a particular molecule in the crystal structure. For instance, if there are more than one molecule that form the unit that is repeated throughout the crystal lattice, then each unit is identified as molecule A, or molecule B, or molecule C, etc 3. Under the headings X, Y, or Z appear the Cartesian coordinates of the atoms in the structure 4. Under the heading OCC appears the "occupancy factor" for each atom. If the entity is present and observed in the structure then an occupancy of 1.00 is assigned to it. If the atom is present but not observed, an occupancy of 0.00 is assigned to it. Also, factors between 0.00 and 1.00 are also acceptable and represent the degree of confidence in observing that atom a that particular position.

5. Under the heading B appears the "B-factor" or "temperature factor" that can adopt, in principle, any value. It is meant to represent the atomic displacement around that position. Atomic coordinates of the native S8 structure (SEQ ID NO:1)

Atomic coordinates of the native S8 structure
CRYST1 42.100 55.500 61.400 90.00 90.00 90.00

| ATOM | | RESIDUE | | | X | Y | Z | Occ | B |
|---|---|---|---|---|---|---|---|---|---|
| 1 | CB | THR | A | 4 | −6.461 | 24.691 | −0.181 | 1.00 | 42.83 |
| 2 | OG1 | THR | A | 4 | −5.711 | 24.797 | −1.400 | 1.00 | 45.08 |
| 3 | CG2 | THR | A | 4 | −7.614 | 23.708 | −0.339 | 1.00 | 45.36 |
| 4 | C | THR | A | 4 | −5.729 | 26.957 | 0.416 | 1.00 | 33.79 |
| 5 | O | THR | A | 4 | −5.382 | 27.840 | −0.383 | 1.00 | 33.22 |
| 6 | N | THR | A | 4 | −7.982 | 26.637 | −0.747 | 1.00 | 37.31 |
| 7 | CA | THR | A | 4 | −6.977 | 26.097 | 0.220 | 1.00 | 39.29 |
| 8 | N | ASP | A | 5 | −5.025 | 26.661 | 1.495 | 1.00 | 23.47 |
| 9 | CA | ASP | A | 5 | −3.817 | 27.419 | 1.821 | 1.00 | 17.33 |
| 10 | CB | ASP | A | 5 | −4.144 | 28.279 | 3.011 | 1.00 | 15.38 |
| 11 | CG | ASP | A | 5 | −2.929 | 29.006 | 3.517 | 1.00 | 14.79 |

-continued

Atomic coordinates of the native S8 structure
CRYST1 42.100 55.500 61.400 90.00 90.00 90.00

| ATOM | | RESIDUE | | | X | Y | Z | Occ | B |
|---|---|---|---|---|---|---|---|---|---|
| 12 | OD1 | ASP | A | 5 | −1.887 | 28.833 | 2.888 | 1.00 | 15.80 |
| 13 | OD2 | ASP | A | 5 | −3.079 | 29.711 | 4.494 | 1.00 | 14.90 |
| 14 | C | ASP | A | 5 | −2.759 | 26.362 | 2.147 | 1.00 | 16.58 |
| 15 | O | ASP | A | 5 | −2.704 | 25.870 | 3.281 | 1.00 | 18.05 |
| 16 | N | PRO | A | 6 | −1.903 | 26.000 | 1.177 | 1.00 | 16.44 |
| 17 | CD | PRO | A | 6 | −1.858 | 26.464 | −0.226 | 1.00 | 20.90 |
| 18 | CA | PRO | A | 6 | −0.887 | 24.971 | 1.423 | 1.00 | 17.38 |
| 19 | CB | PRO | A | 6 | −0.116 | 24.882 | 0.115 | 1.00 | 19.60 |
| 20 | CG | PRO | A | 6 | −1.151 | 25.310 | −0.906 | 1.00 | 24.25 |
| 21 | C | PRO | A | 6 | 0.037 | 25.237 | 2.573 | 1.00 | 16.97 |
| 22 | O | PRO | A | 6 | 0.526 | 24.286 | 3.214 | 1.00 | 14.81 |
| 23 | N | ILE | A | 7 | 0.313 | 26.514 | 2.830 | 1.00 | 13.93 |
| 24 | CA | ILE | A | 7 | 1.212 | 26.837 | 3.939 | 1.00 | 12.98 |
| 25 | CB | ILE | A | 7 | 1.682 | 28.282 | 3.865 | 1.00 | 13.39 |
| 26 | CG2 | ILE | A | 7 | 2.495 | 28.601 | 5.156 | 1.00 | 13.95 |
| 27 | CG1 | ILE | A | 7 | 2.574 | 28.470 | 2.624 | 1.00 | 16.70 |
| 28 | CD1 | ILE | A | 7 | 2.955 | 29.946 | 2.375 | 1.00 | 17.46 |
| 29 | C | ILE | A | 7 | 0.489 | 26.529 | 5.247 | 1.00 | 14.00 |
| 30 | O | ILE | A | 7 | 1.106 | 25.894 | 6.120 | 1.00 | 14.04 |
| 31 | N | ALA | A | 8 | −0.761 | 26.953 | 5.427 | 1.00 | 14.80 |
| 32 | CA | ALA | A | 8 | −1.482 | 26.605 | 6.644 | 1.00 | 13.39 |
| 33 | CB | ALA | A | 8 | −2.869 | 27.199 | 6.629 | 1.00 | 13.83 |
| 34 | C | ALA | A | 8 | −1.565 | 25.053 | 6.751 | 1.00 | 13.55 |
| 35 | O | ALA | A | 8 | −1.446 | 24.453 | 7.843 | 1.00 | 15.03 |
| 36 | N | ASP | A | 9 | −1.791 | 24.363 | 5.635 | 1.00 | 15.10 |
| 37 | CA | ASP | A | 9 | −1.858 | 22.908 | 5.763 | 1.00 | 17.82 |
| 38 | CB | ASP | A | 9 | −2.198 | 22.262 | 4.410 | 1.00 | 18.75 |
| 39 | CG | ASP | A | 9 | −3.558 | 22.657 | 3.887 | 1.00 | 21.83 |
| 40 | OD1 | ASP | A | 9 | −4.455 | 23.107 | 4.646 | 1.00 | 25.74 |
| 41 | OD2 | ASP | A | 9 | −3.736 | 22.501 | 2.654 | 1.00 | 28.91 |
| 42 | C | ASP | A | 9 | −0.533 | 22.332 | 6.276 | 1.00 | 14.90 |
| 43 | O | ASP | A | 9 | −0.542 | 21.378 | 7.067 | 1.00 | 16.11 |
| 44 | N | MET | A | 10 | 0.597 | 22.861 | 5.827 | 1.00 | 13.05 |
| 45 | CA | MET | A | 10 | 1.906 | 22.383 | 6.285 | 1.00 | 14.46 |
| 46 | CB | MET | A | 10 | 3.071 | 23.090 | 5.575 | 1.00 | 13.13 |
| 47 | CG | MET | A | 10 | 4.441 | 22.738 | 6.164 | 1.00 | 12.70 |
| 48 | SD | MET | A | 10 | 5.626 | 23.707 | 5.172 | 1.00 | 15.11 |
| 49 | CE | MET | A | 10 | 7.153 | 23.070 | 5.887 | 1.00 | 13.64 |
| 50 | C | MET | A | 10 | 2.043 | 22.644 | 7.773 | 1.00 | 12.35 |
| 51 | O | MET | A | 10 | 2.446 | 21.742 | 8.503 | 1.00 | 13.00 |
| 52 | N | LEU | A | 11 | 1.741 | 23.853 | 8.222 | 1.00 | 13.28 |
| 53 | CA | LEU | A | 11 | 1.883 | 24.174 | 9.640 | 1.00 | 11.41 |
| 54 | CB | LEU | A | 11 | 1.444 | 25.617 | 9.913 | 1.00 | 10.89 |
| 55 | CG | LEU | A | 11 | 2.303 | 26.671 | 9.158 | 1.00 | 11.59 |
| 56 | CD1 | LEU | A | 11 | 1.757 | 28.056 | 9.614 | 1.00 | 12.36 |
| 57 | CD2 | LEU | A | 11 | 3.809 | 26.562 | 9.385 | 1.00 | 14.75 |
| 58 | C | LEU | A | 11 | 1.029 | 23.226 | 10.476 | 1.00 | 13.64 |
| 59 | O | LEU | A | 11 | 1.471 | 22.766 | 11.515 | 1.00 | 13.28 |
| 60 | N | THR | A | 12 | −0.192 | 22.948 | 10.024 | 1.00 | 11.82 |
| 61 | CA | THR | A | 12 | −1.082 | 22.038 | 10.735 | 1.00 | 12.04 |
| 62 | CB | THR | A | 12 | −2.473 | 22.064 | 10.085 | 1.00 | 13.84 |
| 63 | OG1 | THR | A | 12 | −3.033 | 23.348 | 10.333 | 1.00 | 15.75 |
| 64 | CG2 | THR | A | 12 | −3.388 | 21.020 | 10.697 | 1.00 | 19.14 |
| 65 | C | THR | A | 12 | −0.548 | 20.628 | 10.749 | 1.00 | 13.77 |
| 66 | O | THR | A | 12 | −0.651 | 19.923 | 11.768 | 1.00 | 14.02 |
| 67 | N | ARG | A | 13 | −0.018 | 20.151 | 9.633 | 1.00 | 14.34 |
| 68 | CA | ARG | A | 13 | 0.569 | 18.795 | 9.623 | 1.00 | 15.56 |
| 69 | CB | ARG | A | 13 | 1.106 | 18.446 | 8.216 | 1.00 | 17.77 |
| 70 | CG | ARG | A | 13 | 0.003 | 18.123 | 7.182 | 1.00 | 20.88 |
| 71 | CD | ARG | A | 13 | −0.743 | 16.827 | 7.511 | 1.00 | 25.58 |
| 72 | NE | ARG | A | 13 | 0.198 | 15.737 | 7.751 | 0.75 | 27.19 |
| 73 | CZ | ARG | A | 13 | 1.008 | 15.198 | 6.833 | 1.00 | 29.03 |
| 74 | NH1 | ARG | A | 13 | 1.006 | 15.633 | 5.580 | 1.00 | 33.07 |
| 75 | NH2 | ARG | A | 13 | 1.846 | 14.232 | 7.186 | 1.00 | 31.78 |
| 76 | C | ARG | A | 13 | 1.708 | 18.724 | 10.658 | 1.00 | 13.44 |
| 77 | O | ARG | A | 13 | 1.784 | 17.737 | 11.426 | 1.00 | 14.13 |
| 78 | N | VAL | A | 14 | 2.564 | 19.762 | 10.721 | 1.00 | 12.16 |
| 79 | CA | VAL | A | 14 | 3.683 | 19.767 | 11.669 | 1.00 | 14.68 |
| 80 | CB | VAL | A | 14 | 4.629 | 20.954 | 11.397 | 1.00 | 11.85 |
| 81 | CG1 | VAL | A | 14 | 5.649 | 21.137 | 12.586 | 1.00 | 12.44 |
| 82 | CG2 | VAL | A | 14 | 5.380 | 20.736 | 10.084 | 1.00 | 12.20 |
| 83 | C | VAL | A | 14 | 3.120 | 19.855 | 13.087 | 1.00 | 11.52 |
| 84 | O | VAL | A | 14 | 3.578 | 19.108 | 13.967 | 1.00 | 12.95 |
| 85 | N | ARG | A | 15 | 2.098 | 20.672 | 13.301 | 1.00 | 11.56 |

-continued

Atomic coordinates of the native S8 structure
CRYST1 42.100 55.500 61.400 90.00 90.00 90.00

| ATOM | | RESIDUE | | | X | Y | Z | Occ | B |
|---|---|---|---|---|---|---|---|---|---|
| 86 | CA | ARG | A | 15 | 1.503 | 20.856 | 14.621 | 1.00 | 10.79 |
| 87 | CB | ARG | A | 15 | 0.346 | 21.843 | 14.578 | 1.00 | 11.82 |
| 88 | CG | ARG | A | 15 | −0.211 | 22.232 | 15.946 | 1.00 | 11.89 |
| 89 | CD | ARG | A | 15 | −1.464 | 23.174 | 15.884 | 1.00 | 13.82 |
| 90 | NE | ARG | A | 15 | −1.098 | 24.376 | 15.121 | 1.00 | 14.40 |
| 91 | CZ | ARG | A | 15 | −1.509 | 24.660 | 13.888 | 1.00 | 16.35 |
| 92 | NH1 | ARG | A | 15 | −2.346 | 23.837 | 13.259 | 1.00 | 15.77 |
| 93 | NH2 | ARG | A | 15 | −1.028 | 25.719 | 13.210 | 1.00 | 14.51 |
| 94 | C | ARG | A | 15 | 0.958 | 19.529 | 15.132 | 1.00 | 10.68 |
| 95 | O | ARG | A | 15 | 1.215 | 19.125 | 16.273 | 1.00 | 13.61 |
| 96 | N | ASN | A | 16 | 0.240 | 18.827 | 14.253 | 1.00 | 12.18 |
| 97 | CA | ASN | A | 16 | −0.346 | 17.556 | 14.661 | 1.00 | 15.25 |
| 98 | CB | ASN | A | 16 | −1.341 | 17.080 | 13.590 | 1.00 | 16.21 |
| 99 | CG A | ASN | A | 16 | −2.549 | 18.008 | 13.398 | 0.50 | 18.74 |
| 100 | CG B | ASN | A | 16 | −1.824 | 15.676 | 13.859 | 0.50 | 20.66 |
| 101 | OD1A | ASN | A | 16 | −3.286 | 17.894 | 12.397 | 0.50 | 20.74 |
| 102 | OD1B | ASN | A | 16 | −1.176 | 14.706 | 13.455 | 0.50 | 21.76 |
| 103 | ND2A | ASN | A | 16 | −2.772 | 18.898 | 14.336 | 0.50 | 18.12 |
| 104 | ND2B | ASN | A | 16 | −2.953 | 15.556 | 14.570 | 0.50 | 18.81 |
| 105 | C | ASN | A | 16 | 0.711 | 16.475 | 14.903 | 1.00 | 13.65 |
| 106 | O | ASN | A | 16 | 0.619 | 15.702 | 15.912 | 1.00 | 15.21 |
| 107 | N | ALA | A | 17 | 1.728 | 16.355 | 14.032 | 1.00 | 13.10 |
| 108 | CA | ALA | A | 17 | 2.773 | 15.354 | 14.192 | 1.00 | 14.08 |
| 109 | CB | ALA | A | 17 | 3.758 | 15.372 | 12.963 | 1.00 | 13.25 |
| 110 | C | ALA | A | 17 | 3.571 | 15.588 | 15.463 | 1.00 | 12.71 |
| 111 | O | ALA | A | 17 | 3.954 | 14.630 | 16.129 | 1.00 | 12.71 |
| 112 | N | ASN | A | 18 | 3.809 | 16.866 | 15.795 | 1.00 | 11.25 |
| 113 | CA | ASN | A | 18 | 4.544 | 17.266 | 16.992 | 1.00 | 12.37 |
| 114 | CB | ASN | A | 18 | 4.745 | 18.804 | 16.933 | 1.00 | 12.25 |
| 115 | CG | ASN | A | 18 | 5.595 | 19.334 | 18.082 | 1.00 | 11.43 |
| 116 | OD1 | ASN | A | 18 | 6.644 | 18.759 | 18.401 | 1.00 | 13.81 |
| 117 | ND2 | ASN | A | 18 | 5.148 | 20.396 | 18.705 | 1.00 | 13.40 |
| 118 | C | ASN | A | 18 | 3.726 | 16.858 | 18.230 | 1.00 | 10.83 |
| 119 | O | ASN | A | 18 | 4.291 | 16.311 | 19.197 | 1.00 | 11.44 |
| 120 | N | MET | A | 19 | 2.421 | 17.120 | 18.179 | 1.00 | 12.24 |
| 121 | CA | MET | A | 19 | 1.553 | 16.767 | 19.300 | 1.00 | 12.44 |
| 122 | CB | MET | A | 19 | 0.111 | 17.135 | 18.992 | 1.00 | 12.44 |
| 123 | CG | MET | A | 19 | −0.835 | 16.721 | 20.145 | 1.00 | 13.33 |
| 124 | SD | MET | A | 19 | −2.536 | 17.145 | 19.741 | 1.00 | 18.49 |
| 125 | CE | MET | A | 19 | −2.867 | 15.921 | 18.627 | 1.00 | 20.10 |
| 126 | C | MET | A | 19 | 1.632 | 15.281 | 19.608 | 1.00 | 13.50 |
| 127 | O | MET | A | 19 | 1.740 | 14.873 | 20.782 | 1.00 | 13.60 |
| 128 | N | VAL | A | 20 | 1.538 | 14.452 | 18.562 | 1.00 | 12.37 |
| 129 | CA | VAL | A | 20 | 1.579 | 12.989 | 18.807 | 1.00 | 13.21 |
| 130 | CB | VAL | A | 20 | 0.656 | 12.247 | 17.810 | 1.00 | 15.22 |
| 131 | CG1 | VAL | A | 20 | −0.730 | 12.812 | 17.910 | 1.00 | 14.43 |
| 132 | CG2 | VAL | A | 20 | 1.255 | 12.328 | 16.378 | 1.00 | 16.73 |
| 133 | C | VAL | A | 20 | 2.977 | 12.382 | 18.868 | 1.00 | 16.11 |
| 134 | O | VAL | A | 20 | 3.177 | 11.144 | 18.847 | 1.00 | 19.83 |
| 135 | N | ARG | A | 21 | 3.989 | 13.256 | 18.917 | 1.00 | 13.57 |
| 136 | CA | ARG | A | 21 | 5.382 | 12.881 | 19.060 | 1.00 | 14.55 |
| 137 | CB | ARG | A | 21 | 5.621 | 12.188 | 20.422 | 1.00 | 14.10 |
| 138 | CG | ARG | A | 21 | 5.330 | 13.146 | 21.572 | 1.00 | 10.31 |
| 139 | CD A | ARG | A | 21 | 5.546 | 12.449 | 22.926 | 0.50 | 9.37 |
| 140 | CD B | ARG | A | 21 | 5.543 | 12.473 | 22.941 | 0.50 | 13.63 |
| 141 | NE A | ARG | A | 21 | 5.322 | 13.318 | 24.071 | 0.50 | 5.45 |
| 142 | NE B | ARG | A | 21 | 5.749 | 13.534 | 23.896 | 0.50 | 20.38 |
| 143 | CZ A | ARG | A | 21 | 6.249 | 14.148 | 24.541 | 0.50 | 7.97 |
| 144 | CZ B | ARG | A | 21 | 6.905 | 14.178 | 24.000 | 0.50 | 17.62 |
| 145 | NH1A | ARG | A | 21 | 7.438 | 14.232 | 23.955 | 0.50 | 11.73 |
| 146 | NH1B | ARG | A | 21 | 7.938 | 13.839 | 23.243 | 0.50 | 16.00 |
| 147 | NH2A | ARG | A | 21 | 6.001 | 14.869 | 25.591 | 0.50 | 13.99 |
| 148 | NH2B | ARG | A | 21 | 6.999 | 15.205 | 24.787 | 0.50 | 9.14 |
| 149 | C | ARG | A | 21 | 5.929 | 11.985 | 17.950 | 1.00 | 19.18 |
| 150 | O | ARG | A | 21 | 6.742 | 11.110 | 18.212 | 1.00 | 19.79 |
| 151 | N | HIS | A | 22 | 5.490 | 12.236 | 16.714 | 1.00 | 17.02 |
| 152 | CA | HIS | A | 22 | 6.034 | 11.468 | 15.596 | 1.00 | 18.66 |
| 153 | CB | HIS | A | 22 | 5.294 | 11.744 | 14.280 | 1.00 | 19.15 |
| 154 | CG | HIS | A | 22 | 3.964 | 11.071 | 14.152 | 1.00 | 20.64 |
| 155 | CD2 | HIS | A | 22 | 2.849 | 11.436 | 13.473 | 1.00 | 24.91 |
| 156 | ND1 | HIS | A | 22 | 3.648 | 9.905 | 14.816 | 1.00 | 30.45 |
| 157 | CE1 | HIS | A | 22 | 2.394 | 9.585 | 14.559 | 1.00 | 29.06 |
| 158 | NE2 | HIS | A | 22 | 1.884 | 10.498 | 13.749 | 1.00 | 33.58 |
| 159 | C | HIS | A | 22 | 7.508 | 11.849 | 15.369 | 1.00 | 19.73 |

-continued

Atomic coordinates of the native S8 structure
CRYST1 42.100 55.500 61.400 90.00 90.00 90.00

| | ATOM | RESIDUE | | | X | Y | Z | Occ | B |
|---|---|---|---|---|---|---|---|---|---|
| 160 | O | HIS | A | 22 | 7.941 | 13.005 | 15.558 | 1.00 | 17.77 |
| 161 | N | GLU | A | 23 | 8.270 | 10.888 | 14.855 | 1.00 | 19.88 |
| 162 | CA | GLU | A | 23 | 9.664 | 11.113 | 14.541 | 1.00 | 20.11 |
| 163 | CB | GLU | A | 23 | 10.358 | 9.768 | 14.260 | 1.00 | 27.37 |
| 164 | CG | GLU | A | 23 | 11.815 | 9.905 | 13.819 | 1.00 | 30.59 |
| 165 | CD | GLU | A | 23 | 12.429 | 8.591 | 13.293 | 1.00 | 40.76 |
| 166 | OE1 | GLU | A | 23 | 11.709 | 7.766 | 12.678 | 1.00 | 43.53 |
| 167 | OE2 | GLU | A | 23 | 13.651 | 8.408 | 13.481 | 1.00 | 47.87 |
| 168 | C | GLU | A | 23 | 9.729 | 11.975 | 13.274 | 1.00 | 16.44 |
| 169 | O | GLU | A | 23 | 10.616 | 12.791 | 13.138 | 1.00 | 16.55 |
| 170 | N | LYS | A | 24 | 8.774 | 11.760 | 12.380 | 1.00 | 16.86 |
| 171 | CA | LYS | A | 24 | 8.785 | 12.509 | 11.109 | 1.00 | 19.29 |
| 172 | CB | LYS | A | 24 | 9.759 | 11.818 | 10.132 | 1.00 | 21.65 |
| 173 | CG | LYS | A | 24 | 9.201 | 10.533 | 9.541 | 1.00 | 28.20 |
| 174 | CD | LYS | A | 24 | 10.257 | 9.774 | 8.783 | 1.00 | 31.38 |
| 175 | CE | LYS | A | 24 | 11.155 | 9.031 | 9.726 | 0.50 | 33.74 |
| 176 | NZ | LYS | A | 24 | 11.650 | 9.926 | 10.809 | 0.50 | 33.81 |
| 177 | C | LYS | A | 24 | 7.408 | 12.562 | 10.493 | 1.00 | 17.40 |
| 178 | O | LYS | A | 24 | 6.445 | 11.905 | 10.940 | 1.00 | 18.36 |
| 179 | N | LEU | A | 25 | 7.305 | 13.356 | 9.425 | 1.00 | 16.29 |
| 180 | CA | LEU | A | 25 | 6.086 | 13.453 | 8.672 | 1.00 | 17.35 |
| 181 | CB | LEU | A | 25 | 5.117 | 14.499 | 9.247 | 1.00 | 17.32 |
| 182 | CG | LEU | A | 25 | 5.595 | 15.954 | 9.132 | 1.00 | 16.73 |
| 183 | CD1 | LEU | A | 25 | 4.366 | 16.848 | 9.061 | 1.00 | 21.28 |
| 184 | CD2 | LEU | A | 25 | 6.520 | 16.367 | 10.286 | 1.00 | 19.12 |
| 185 | C | LEU | A | 25 | 6.467 | 13.805 | 7.228 | 1.00 | 16.64 |
| 186 | O | LEU | A | 25 | 7.582 | 14.278 | 6.964 | 1.00 | 16.92 |
| 187 | N | GLU | A | 26 | 5.557 | 13.491 | 6.322 | 1.00 | 18.27 |
| 188 | CA | GLU | A | 26 | 5.785 | 13.801 | 4.903 | 1.00 | 18.14 |
| 189 | CB | GLU | A | 26 | 5.813 | 12.499 | 4.063 | 1.00 | 17.91 |
| 190 | CG | GLU | A | 26 | 7.116 | 11.762 | 4.199 | 1.00 | 24.85 |
| 191 | CD | GLU | A | 26 | 7.103 | 10.438 | 3.491 | 1.00 | 29.39 |
| 192 | OE1 | GLU | A | 26 | 6.263 | 10.245 | 2.563 | 1.00 | 30.78 |
| 193 | OE2 | GLU | A | 26 | 7.946 | 9.602 | 3.879 | 1.00 | 35.10 |
| 194 | C | GLU | A | 26 | 4.660 | 14.652 | 4.429 | 1.00 | 16.57 |
| 195 | O | GLU | A | 26 | 3.523 | 14.477 | 4.840 | 1.00 | 22.49 |
| 196 | N | LEU | A | 27 | 4.956 | 15.625 | 3.564 | 1.00 | 16.18 |
| 197 | CA | LEU | A | 27 | 3.917 | 16.450 | 3.000 | 1.00 | 19.66 |
| 198 | CB | LEU | A | 27 | 3.661 | 17.706 | 3.869 | 1.00 | 22.81 |
| 199 | CG | LEU | A | 27 | 4.884 | 18.573 | 4.237 | 1.00 | 25.00 |
| 200 | CD1 | LEU | A | 27 | 4.664 | 19.914 | 3.610 | 1.00 | 22.75 |
| 201 | CD2 | LEU | A | 27 | 5.029 | 18.750 | 5.734 | 1.00 | 28.32 |
| 202 | C | LEU | A | 27 | 4.323 | 16.842 | 1.571 | 1.00 | 17.53 |
| 203 | O | LEU | A | 27 | 5.495 | 16.802 | 1.239 | 1.00 | 19.86 |
| 204 | N | PRO | A | 28 | 3.349 | 17.237 | 0.736 | 1.00 | 20.65 |
| 205 | CD | PRO | A | 28 | 1.927 | 17.491 | 1.004 | 1.00 | 20.94 |
| 206 | CA | PRO | A | 28 | 3.704 | 17.621 | −0.645 | 1.00 | 20.41 |
| 207 | CB | PRO | A | 28 | 2.361 | 18.010 | −1.258 | 1.00 | 23.88 |
| 208 | CG | PRO | A | 28 | 1.321 | 17.286 | −0.347 | 1.00 | 27.18 |
| 209 | C | PRO | A | 28 | 4.673 | 18.799 | −0.653 | 1.00 | 20.38 |
| 210 | O | PRO | A | 28 | 4.556 | 19.748 | 0.129 | 1.00 | 19.44 |
| 211 | N | ALA | A | 29 | 5.603 | 18.790 | −1.593 | 1.00 | 18.16 |
| 212 | CA | ALA | A | 29 | 6.564 | 19.853 | −1.704 | 1.00 | 21.72 |
| 213 | CB | ALA | A | 29 | 7.848 | 19.311 | −2.300 | 1.00 | 19.37 |
| 214 | C | ALA | A | 29 | 6.108 | 21.022 | −2.553 | 1.00 | 18.53 |
| 215 | O | ALA | A | 29 | 5.245 | 20.890 | −3.436 | 1.00 | 18.27 |
| 216 | N | SER | A | 30 | 6.626 | 22.190 | −2.201 | 1.00 | 18.34 |
| 217 | CA | SER | A | 30 | 6.449 | 23.411 | −3.047 | 1.00 | 16.19 |
| 218 | CB | SER | A | 30 | 5.183 | 24.209 | −2.727 | 1.00 | 20.14 |
| 219 | OG | SER | A | 30 | 5.339 | 24.974 | −1.529 | 1.00 | 21.32 |
| 220 | C | SER | A | 30 | 7.708 | 24.222 | −2.777 | 1.00 | 15.57 |
| 221 | O | SER | A | 30 | 8.472 | 23.997 | −1.798 | 1.00 | 18.05 |
| 222 | N | ASN | A | 31 | 7.994 | 25.191 | −3.642 | 1.00 | 17.71 |
| 223 | CA | ASN | A | 31 | 9.196 | 25.960 | −3.419 | 1.00 | 15.27 |
| 224 | CB | ASN | A | 31 | 9.347 | 27.009 | −4.532 | 1.00 | 15.19 |
| 225 | CG | ASN | A | 31 | 9.730 | 26.380 | −5.894 | 1.00 | 19.59 |
| 226 | OD1 | ASN | A | 31 | 10.574 | 25.451 | −5.969 | 1.00 | 21.13 |
| 227 | ND2 | ASN | A | 31 | 9.134 | 26.918 | −6.969 | 1.00 | 18.82 |
| 228 | C | ASN | A | 31 | 9.208 | 26.685 | −2.050 | 1.00 | 14.86 |
| 229 | O | ASN | A | 31 | 10.204 | 26.632 | −1.334 | 1.00 | 17.77 |
| 230 | N | ILE | A | 32 | 8.101 | 27.357 | −1.743 | 1.00 | 19.65 |
| 231 | CA | ILE | A | 32 | 8.001 | 28.096 | −0.485 | 1.00 | 15.20 |
| 232 | CB A | ILE | A | 32 | 6.812 | 29.111 | −0.495 | 0.50 | 17.15 |
| 233 | CB B | ILE | A | 32 | 6.701 | 28.953 | −0.500 | 0.50 | 14.78 |

-continued

Atomic coordinates of the native S8 structure
CRYST1 42.100 55.500 61.400 90.00 90.00 90.00

| ATOM | | RESIDUE | | | X | Y | Z | Occ | B |
|---|---|---|---|---|---|---|---|---|---|
| 234 | CG2A | ILE | A | 32 | 5.490 | 28.426 | −0.375 | 0.50 | 19.36 |
| 235 | CG2B | ILE | A | 32 | 5.468 | 28.112 | −0.368 | 0.50 | 23.40 |
| 236 | CG1A | ILE | A | 32 | 7.040 | 30.127 | 0.644 | 0.50 | 18.07 |
| 237 | CG1B | ILE | A | 32 | 6.797 | 29.987 | 0.609 | 0.50 | 21.16 |
| 238 | CD1A | ILE | A | 32 | 6.228 | 31.417 | 0.520 | 0.50 | 15.99 |
| 239 | CD1B | ILE | A | 32 | 7.978 | 30.835 | 0.383 | 0.50 | 19.15 |
| 240 | C | ILE | A | 32 | 7.989 | 27.143 | 0.727 | 1.00 | 16.46 |
| 241 | O | ILE | A | 32 | 8.619 | 27.437 | 1.757 | 1.00 | 15.29 |
| 242 | N | LYS | A | 33 | 7.332 | 25.998 | 0.591 | 1.00 | 17.77 |
| 243 | CA | LYS | A | 33 | 7.309 | 25.048 | 1.743 | 1.00 | 16.20 |
| 244 | CB | LYS | A | 33 | 6.261 | 23.944 | 1.526 | 1.00 | 13.11 |
| 245 | CG | LYS | A | 33 | 4.798 | 24.446 | 1.720 | 1.00 | 14.90 |
| 246 | CD | LYS | A | 33 | 3.750 | 23.335 | 1.630 | 1.00 | 15.37 |
| 247 | CE | LYS | A | 33 | 3.503 | 22.844 | 0.200 | 1.00 | 18.69 |
| 248 | NZ | LYS | A | 33 | 2.494 | 21.745 | 0.216 | 1.00 | 22.36 |
| 249 | C | LYS | A | 33 | 8.715 | 24.549 | 2.031 | 1.00 | 18.54 |
| 250 | O | LYS | A | 33 | 9.101 | 24.325 | 3.200 | 1.00 | 16.33 |
| 251 | N | LYS | A | 34 | 9.521 | 24.317 | 0.983 | 1.00 | 17.44 |
| 252 | CA | LYS | A | 34 | 10.901 | 23.930 | 1.190 | 1.00 | 15.42 |
| 253 | CB | LYS | A | 34 | 11.526 | 23.571 | −0.171 | 1.00 | 19.61 |
| 254 | CG | LYS | A | 34 | 12.900 | 23.000 | −0.095 | 1.00 | 26.10 |
| 255 | CD | LYS | A | 34 | 13.498 | 22.704 | −1.485 | 1.00 | 29.86 |
| 256 | CE | LYS | A | 34 | 12.682 | 21.719 | −2.274 | 1.00 | 27.95 |
| 257 | NZ | LYS | A | 34 | 13.503 | 21.212 | −3.424 | 1.00 | 38.16 |
| 258 | C | LYS | A | 34 | 11.690 | 25.047 | 1.883 | 1.00 | 17.26 |
| 259 | O | LYS | A | 34 | 12.504 | 24.778 | 2.749 | 1.00 | 16.84 |
| 260 | N | GLU | A | 35 | 11.505 | 26.317 | 1.492 | 1.00 | 14.62 |
| 261 | CA | GLU | A | 35 | 12.208 | 27.398 | 2.161 | 1.00 | 16.43 |
| 262 | CB | GLU | A | 35 | 11.855 | 28.761 | 1.577 | 1.00 | 15.39 |
| 263 | CG | GLU | A | 35 | 12.379 | 29.019 | 0.228 | 1.00 | 17.59 |
| 264 | CD | GLU | A | 35 | 12.187 | 30.512 | −0.087 | 1.00 | 14.10 |
| 265 | OE1 | GLU | A | 35 | 13.022 | 31.331 | 0.398 | 1.00 | 15.22 |
| 266 | OE2 | GLU | A | 35 | 11.194 | 30.810 | −0.784 | 1.00 | 20.61 |
| 267 | C | GLU | A | 35 | 11.809 | 27.425 | 3.643 | 1.00 | 14.00 |
| 268 | O | GLU | A | 35 | 12.651 | 27.666 | 4.506 | 1.00 | 15.78 |
| 269 | N | ILE | A | 36 | 10.530 | 27.183 | 3.892 | 1.00 | 16.23 |
| 270 | CA | ILE | A | 36 | 10.039 | 27.185 | 5.292 | 1.00 | 14.47 |
| 271 | CB | ILE | A | 36 | 8.510 | 27.040 | 5.308 | 1.00 | 13.60 |
| 272 | CG2 | ILE | A | 36 | 8.015 | 26.724 | 6.711 | 1.00 | 17.28 |
| 273 | CG1 | ILE | A | 36 | 7.914 | 28.343 | 4.763 | 1.00 | 14.47 |
| 274 | CD1 | ILE | A | 36 | 6.428 | 28.274 | 4.541 | 1.00 | 16.94 |
| 275 | C | ILE | A | 36 | 10.697 | 26.062 | 6.097 | 1.00 | 14.19 |
| 276 | O | ILE | A | 36 | 11.255 | 26.303 | 7.205 | 1.00 | 14.89 |
| 277 | N | ALA | A | 37 | 10.720 | 24.884 | 5.482 | 1.00 | 15.18 |
| 278 | CA | ALA | A | 37 | 11.319 | 23.723 | 6.148 | 1.00 | 15.59 |
| 279 | CB | ALA | A | 37 | 11.141 | 22.502 | 5.257 | 1.00 | 17.71 |
| 280 | C | ALA | A | 37 | 12.784 | 23.958 | 6.483 | 1.00 | 16.91 |
| 281 | O | ALA | A | 37 | 13.254 | 23.610 | 7.593 | 1.00 | 17.94 |
| 282 | N | GLU | A | 38 | 13.554 | 24.566 | 5.561 | 1.00 | 15.64 |
| 283 | CA | GLU | A | 38 | 14.947 | 24.850 | 5.847 | 1.00 | 17.27 |
| 284 | CB | GLU | A | 38 | 15.703 | 25.267 | 4.559 | 1.00 | 18.26 |
| 285 | CG | GLU | A | 38 | 15.871 | 24.166 | 3.536 | 1.00 | 26.66 |
| 286 | CD | GLU | A | 38 | 16.713 | 22.998 | 4.047 | 1.00 | 25.35 |
| 287 | OE1 | GLU | A | 38 | 17.656 | 23.241 | 4.833 | 1.00 | 27.87 |
| 288 | OE2 | GLU | A | 38 | 16.423 | 21.861 | 3.643 | 1.00 | 30.64 |
| 289 | C | GLU | A | 38 | 15.189 | 25.874 | 6.927 | 1.00 | 18.13 |
| 290 | O | GLU | A | 38 | 16.162 | 25.771 | 7.657 | 1.00 | 17.88 |
| 291 | N | ILE | A | 39 | 14.322 | 26.893 | 7.055 | 1.00 | 16.32 |
| 292 | CA | ILE | A | 39 | 14.469 | 27.862 | 8.132 | 1.00 | 16.76 |
| 293 | CB A | ILE | A | 39 | 13.596 | 29.114 | 7.940 | 0.50 | 17.98 |
| 294 | CB B | ILE | A | 39 | 13.552 | 29.099 | 7.926 | 0.50 | 20.20 |
| 295 | CG2A | ILE | A | 39 | 13.419 | 29.872 | 9.275 | 0.50 | 15.47 |
| 296 | CG2B | ILE | A | 39 | 13.701 | 30.070 | 9.112 | 0.50 | 20.19 |
| 297 | CG1A | ILE | A | 39 | 14.290 | 30.034 | 6.960 | 0.50 | 16.30 |
| 298 | CG1B | ILE | A | 39 | 13.891 | 29.783 | 6.599 | 0.50 | 21.26 |
| 299 | CD1A | ILE | A | 39 | 13.373 | 31.005 | 6.323 | 0.50 | 12.77 |
| 300 | CD1B | ILE | A | 39 | 15.255 | 30.429 | 6.550 | 0.50 | 23.48 |
| 301 | C | ILE | A | 39 | 14.101 | 27.176 | 9.485 | 1.00 | 14.27 |
| 302 | O | ILE | A | 39 | 14.752 | 27.410 | 10.487 | 1.00 | 17.34 |
| 303 | N | LEU | A | 40 | 13.111 | 26.294 | 9.466 | 1.00 | 15.11 |
| 304 | CA | LEU | A | 40 | 12.778 | 25.591 | 10.700 | 1.00 | 12.68 |
| 305 | CB | LEU | A | 40 | 11.566 | 24.659 | 10.517 | 1.00 | 12.13 |
| 306 | CG | LEU | A | 40 | 10.254 | 25.407 | 10.228 | 1.00 | 12.48 |
| 307 | CD1 | LEU | A | 40 | 9.122 | 24.392 | 10.022 | 1.00 | 16.06 |

-continued

Atomic coordinates of the native S8 structure
CRYST1 42.100 55.500 61.400 90.00 90.00 90.00

| ATOM | | RESIDUE | | | X | Y | Z | Occ | B |
|---|---|---|---|---|---|---|---|---|---|
| 308 | CD2 | LEU | A | 40 | 9.898 | 26.311 | 11.408 | 1.00 | 17.03 |
| 309 | C | LEU | A | 40 | 13.992 | 24.819 | 11.146 | 1.00 | 15.02 |
| 310 | O | LEU | A | 40 | 14.265 | 24.730 | 12.317 | 1.00 | 14.50 |
| 311 | N | LYS | A | 41 | 14.716 | 24.243 | 10.183 | 1.00 | 13.32 |
| 312 | CA | LYS | A | 41 | 15.908 | 23.470 | 10.524 | 1.00 | 14.52 |
| 313 | CB | LYS | A | 41 | 16.373 | 22.651 | 9.311 | 1.00 | 15.64 |
| 314 | CG | LYS | A | 41 | 17.618 | 21.819 | 9.539 | 1.00 | 18.37 |
| 315 | CD | LYS | A | 41 | 18.012 | 21.109 | 8.268 | 1.00 | 25.04 |
| 316 | CE | LYS | A | 41 | 19.355 | 20.435 | 8.470 | 1.00 | 28.16 |
| 317 | NZ | LYS | A | 41 | 19.776 | 19.797 | 7.183 | 1.00 | 24.42 |
| 318 | C | LYS | A | 41 | 17.038 | 24.386 | 10.993 | 1.00 | 17.40 |
| 319 | O | LYS | A | 41 | 17.623 | 24.180 | 12.049 | 1.00 | 21.49 |
| 320 | N | SER | A | 42 | 17.337 | 25.429 | 10.213 | 1.00 | 17.40 |
| 321 | CA | SER | A | 42 | 18.457 | 26.259 | 10.617 | 1.00 | 19.84 |
| 322 | CB | SER | A | 42 | 18.821 | 27.258 | 9.504 | 1.00 | 22.89 |
| 323 | OG | SER | A | 42 | 17.798 | 28.213 | 9.318 | 1.00 | 26.40 |
| 324 | C | SER | A | 42 | 18.209 | 26.949 | 11.933 | 1.00 | 21.31 |
| 325 | O | SER | A | 42 | 19.154 | 27.210 | 12.680 | 1.00 | 22.43 |
| 326 | N | GLU | A | 43 | 16.936 | 27.199 | 12.261 | 1.00 | 19.93 |
| 327 | CA | GLU | A | 43 | 16.581 | 27.857 | 13.509 | 1.00 | 17.11 |
| 328 | CB | GLU | A | 43 | 15.289 | 28.678 | 13.335 | 1.00 | 20.03 |
| 329 | CG | GLU | A | 43 | 15.506 | 29.879 | 12.424 | 1.00 | 20.26 |
| 330 | CD | GLU | A | 43 | 16.464 | 30.905 | 13.044 | 1.00 | 21.79 |
| 331 | OE1 | GLU | A | 43 | 16.183 | 31.346 | 14.183 | 1.00 | 24.68 |
| 332 | OE2 | GLU | A | 43 | 17.460 | 31.260 | 12.356 | 1.00 | 24.12 |
| 333 | C | GLU | A | 43 | 16.454 | 26.907 | 14.685 | 1.00 | 19.29 |
| 334 | O | GLU | A | 43 | 16.111 | 27.309 | 15.804 | 1.00 | 21.07 |
| 335 | N | GLY | A | 44 | 16.708 | 25.625 | 14.410 | 1.00 | 18.95 |
| 336 | CA | GLY | A | 44 | 16.684 | 24.647 | 15.485 | 1.00 | 18.08 |
| 337 | C | GLY | A | 44 | 15.331 | 24.095 | 15.866 | 1.00 | 20.18 |
| 338 | O | GLY | A | 44 | 15.224 | 23.368 | 16.853 | 1.00 | 22.41 |
| 339 | N | PHE | A | 45 | 14.292 | 24.392 | 15.090 | 1.00 | 16.56 |
| 340 | CA | PHE | A | 45 | 12.976 | 23.887 | 15.466 | 1.00 | 16.87 |
| 341 | CB | PHE | A | 45 | 11.905 | 24.822 | 14.943 | 1.00 | 12.09 |
| 342 | CG | PHE | A | 45 | 11.759 | 26.075 | 15.751 | 1.00 | 13.00 |
| 343 | CD1 | PHE | A | 45 | 11.169 | 26.036 | 17.004 | 1.00 | 12.05 |
| 344 | CD2 | PHE | A | 45 | 12.218 | 27.292 | 15.266 | 1.00 | 14.04 |
| 345 | CE1 | PHE | A | 45 | 11.036 | 27.199 | 17.769 | 1.00 | 14.85 |
| 346 | CE2 | PHE | A | 45 | 12.090 | 28.457 | 16.027 | 1.00 | 15.80 |
| 347 | CZ | PHE | A | 45 | 11.495 | 28.398 | 17.271 | 1.00 | 13.65 |
| 348 | C | PHE | A | 45 | 12.704 | 22.468 | 15.003 | 1.00 | 18.86 |
| 349 | O | PHE | A | 45 | 11.857 | 21.797 | 15.567 | 1.00 | 17.57 |
| 350 | N | ILE | A | 46 | 13.335 | 22.059 | 13.899 | 1.00 | 16.30 |
| 351 | CA | ILE | A | 46 | 13.224 | 20.683 | 13.456 | 1.00 | 17.57 |
| 352 | CB | ILE | A | 46 | 12.405 | 20.489 | 12.157 | 1.00 | 13.61 |
| 353 | CG2 | ILE | A | 46 | 10.982 | 20.969 | 12.347 | 1.00 | 14.82 |
| 354 | CG1 | ILE | A | 46 | 13.105 | 21.175 | 10.985 | 1.00 | 16.03 |
| 355 | CD1 | ILE | A | 46 | 12.437 | 20.868 | 9.686 | 1.00 | 17.25 |
| 356 | C | ILE | A | 46 | 14.633 | 20.155 | 13.262 | 1.00 | 16.90 |
| 357 | O | ILE | A | 46 | 15.608 | 20.926 | 13.169 | 1.00 | 17.77 |
| 358 | N | LYS | A | 47 | 14.754 | 18.840 | 13.175 | 1.00 | 17.55 |
| 359 | CA | LYS | A | 47 | 16.050 | 18.200 | 13.042 | 1.00 | 20.67 |
| 360 | CB | LYS | A | 47 | 15.916 | 16.801 | 13.653 | 1.00 | 22.04 |
| 361 | CG | LYS | A | 47 | 17.167 | 15.986 | 13.857 | 1.00 | 34.96 |
| 362 | CD | LYS | A | 47 | 16.813 | 14.776 | 14.737 | 1.00 | 40.91 |
| 363 | CE | LYS | A | 47 | 18.049 | 14.001 | 15.192 | 1.00 | 45.35 |
| 364 | NZ | LYS | A | 47 | 17.689 | 12.841 | 16.081 | 1.00 | 47.44 |
| 365 | C | LYS | A | 47 | 16.587 | 18.137 | 11.627 | 1.00 | 23.96 |
| 366 | O | LYS | A | 47 | 17.791 | 18.352 | 11.410 | 1.00 | 27.25 |
| 367 | N | ASN | A | 48 | 15.724 | 17.862 | 10.660 | 1.00 | 23.14 |
| 368 | CA | ASN | A | 48 | 16.204 | 17.780 | 9.277 | 1.00 | 23.76 |
| 369 | CB | ASN | A | 48 | 17.093 | 16.533 | 9.136 | 1.00 | 28.30 |
| 370 | CG | ASN | A | 48 | 17.725 | 16.427 | 7.773 | 1.00 | 33.93 |
| 371 | OD1 | ASN | A | 48 | 18.184 | 17.433 | 7.219 | 1.00 | 35.73 |
| 372 | ND2 | ASN | A | 48 | 17.758 | 15.209 | 7.223 | 1.00 | 36.71 |
| 373 | C | ASN | A | 48 | 15.055 | 17.742 | 8.283 | 1.00 | 25.78 |
| 374 | O | ASN | A | 48 | 13.897 | 17.606 | 8.684 | 1.00 | 18.82 |
| 375 | N | VAL | A | 49 | 15.387 | 17.875 | 6.990 | 1.00 | 20.75 |
| 376 | CA | VAL | A | 49 | 14.418 | 17.827 | 5.891 | 1.00 | 20.69 |
| 377 | CB | VAL | A | 49 | 14.117 | 19.222 | 5.268 | 1.00 | 22.40 |
| 378 | CG1 | VAL | A | 49 | 12.892 | 19.144 | 4.264 | 1.00 | 21.21 |
| 379 | CG2 | VAL | A | 49 | 13.924 | 20.230 | 6.368 | 1.00 | 24.41 |
| 380 | C | VAL | A | 49 | 15.049 | 17.019 | 4.783 | 1.00 | 21.17 |
| 381 | O | VAL | A | 49 | 16.189 | 17.291 | 4.415 | 1.00 | 28.56 |

-continued

Atomic coordinates of the native S8 structure
CRYST1 42.100 55.500 61.400 90.00 90.00 90.00

| ATOM | | RESIDUE | | | X | Y | Z | Occ | B |
|---|---|---|---|---|---|---|---|---|---|
| 382 | N | GLU | A | 50 | 14.309 | 16.058 | 4.262 | 1.00 | 20.50 |
| 383 | CA | GLU | A | 50 | 14.783 | 15.246 | 3.130 | 1.00 | 22.14 |
| 384 | CB | GLU | A | 50 | 14.761 | 13.754 | 3.486 | 1.00 | 24.09 |
| 385 | CG | GLU | A | 50 | 15.952 | 13.292 | 4.274 | 1.00 | 29.46 |
| 386 | CD | GLU | A | 50 | 15.883 | 11.830 | 4.657 | 1.00 | 31.31 |
| 387 | OE1 | GLU | A | 50 | 16.876 | 11.335 | 5.234 | 1.00 | 38.72 |
| 388 | OE2 | GLU | A | 50 | 14.838 | 11.187 | 4.405 | 1.00 | 31.03 |
| 389 | C | GLU | A | 50 | 13.787 | 15.497 | 1.994 | 1.00 | 23.91 |
| 390 | O | GLU | A | 50 | 12.589 | 15.669 | 2.233 | 1.00 | 20.50 |
| 391 | N | TYR | A | 51 | 14.281 | 15.482 | 0.747 | 1.00 | 26.16 |
| 392 | CA | TYR | A | 51 | 13.432 | 15.676 | −0.432 | 1.00 | 22.90 |
| 393 | CB | TYR | A | 51 | 14.198 | 16.524 | −1.454 | 1.00 | 24.90 |
| 394 | CG | TYR | A | 51 | 14.616 | 17.903 | −0.958 | 1.00 | 29.44 |
| 395 | CD1 | TYR | A | 51 | 15.629 | 18.620 | −1.617 | 1.00 | 33.16 |
| 396 | CE1 | TYR | A | 51 | 16.051 | 19.883 | −1.158 | 1.00 | 31.21 |
| 397 | CD2 | TYR | A | 51 | 14.020 | 18.489 | 0.172 | 1.00 | 32.63 |
| 398 | CE2 | TYR | A | 51 | 14.432 | 19.746 | 0.648 | 1.00 | 29.86 |
| 399 | CZ | TYR | A | 51 | 15.453 | 20.435 | −0.022 | 1.00 | 37.58 |
| 400 | OH | TYR | A | 51 | 15.918 | 21.647 | 0.458 | 1.00 | 39.41 |
| 401 | C | TYR | A | 51 | 13.136 | 14.263 | −0.982 | 1.00 | 21.94 |
| 402 | O | TYR | A | 51 | 14.049 | 13.483 | −1.173 | 1.00 | 27.59 |
| 403 | N | VAL | A | 52 | 11.861 | 13.956 | −1.220 | 1.00 | 21.78 |
| 404 | CA | VAL | A | 52 | 11.417 | 12.645 | −1.653 | 1.00 | 26.05 |
| 405 | CB | VAL | A | 52 | 10.458 | 12.039 | −0.556 | 1.00 | 25.02 |
| 406 | CG1 | VAL | A | 52 | 9.963 | 10.670 | −0.928 | 1.00 | 28.46 |
| 407 | CG2 | VAL | A | 52 | 11.171 | 11.989 | 0.781 | 1.00 | 29.62 |
| 408 | C | VAL | A | 52 | 10.667 | 12.687 | −2.982 | 1.00 | 22.77 |
| 409 | O | VAL | A | 52 | 9.787 | 13.492 | −3.177 | 1.00 | 21.42 |
| 410 | N | GLU | A | 53 | 11.002 | 11.783 | −3.900 | 1.00 | 25.82 |
| 411 | CA | GLU | A | 53 | 10.315 | 11.722 | −5.182 | 1.00 | 24.93 |
| 412 | CB | GLU | A | 53 | 11.183 | 10.936 | −6.170 | 1.00 | 31.27 |
| 413 | CG | GLU | A | 53 | 12.599 | 11.449 | −6.262 | 1.00 | 35.20 |
| 414 | CD | GLU | A | 53 | 13.443 | 10.666 | −7.242 | 0.50 | 39.45 |
| 415 | OE1 | GLU | A | 53 | 12.862 | 10.086 | −8.184 | 0.50 | 39.39 |
| 416 | OE2 | GLU | A | 53 | 14.684 | 10.644 | −7.077 | 0.50 | 38.84 |
| 417 | C | GLU | A | 53 | 8.943 | 11.061 | −5.081 | 1.00 | 26.25 |
| 418 | O | GLU | A | 53 | 8.701 | 10.201 | −4.212 | 1.00 | 27.80 |
| 419 | N | ASP | A | 54 | 8.029 | 11.480 | −5.945 | 1.00 | 22.37 |
| 420 | CA | ASP | A | 54 | 6.694 | 10.889 | −6.004 | 1.00 | 28.05 |
| 421 | CB | ASP | A | 54 | 5.725 | 11.540 | −4.992 | 1.00 | 26.65 |
| 422 | CG | ASP | A | 54 | 5.247 | 12.911 | −5.400 | 1.00 | 27.40 |
| 423 | OD1 | ASP | A | 54 | 5.824 | 13.516 | −6.325 | 1.00 | 26.17 |
| 424 | OD2 | ASP | A | 54 | 4.283 | 13.394 | −4.767 | 1.00 | 30.42 |
| 425 | C | ASP | A | 54 | 6.229 | 11.023 | −7.467 | 1.00 | 26.89 |
| 426 | O | ASP | A | 54 | 7.054 | 11.330 | −8.329 | 1.00 | 27.63 |
| 427 | N | ASP | A | 55 | 4.948 | 10.786 | −7.750 | 1.00 | 32.96 |
| 428 | CA | ASP | A | 55 | 4.440 | 10.860 | −9.127 | 1.00 | 36.53 |
| 429 | CB | ASP | A | 55 | 3.444 | 9.715 | −9.347 | 1.00 | 39.57 |
| 430 | CG | ASP | A | 55 | 2.172 | 9.876 | −8.515 | 1.00 | 45.50 |
| 431 | OD1 | ASP | A | 55 | 2.252 | 10.429 | −7.401 | 1.00 | 47.07 |
| 432 | OD2 | ASP | A | 55 | 1.093 | 9.450 | −8.972 | 1.00 | 48.67 |
| 433 | C | ASP | A | 55 | 3.786 | 12.216 | −9.453 | 1.00 | 38.03 |
| 434 | O | ASP | A | 55 | 2.973 | 12.349 | −10.395 | 1.00 | 39.71 |
| 435 | N | LYS | A | 56 | 4.152 | 13.226 | −8.671 | 1.00 | 33.03 |
| 436 | CA | LYS | A | 56 | 3.630 | 14.574 | −8.827 | 1.00 | 31.69 |
| 437 | CB | LYS | A | 56 | 2.611 | 14.862 | −7.713 | 1.00 | 33.79 |
| 438 | CG | LYS | A | 56 | 1.376 | 13.938 | −7.780 | 1.00 | 39.31 |
| 439 | CD | LYS | A | 56 | 0.462 | 14.111 | −6.564 | 1.00 | 41.42 |
| 440 | CE | LYS | A | 56 | −0.552 | 12.982 | −6.461 | 0.50 | 44.11 |
| 441 | NZ | LYS | A | 56 | −1.562 | 13.216 | −5.374 | 0.50 | 44.17 |
| 442 | C | LYS | A | 56 | 4.811 | 15.532 | −8.745 | 1.00 | 32.28 |
| 443 | O | LYS | A | 56 | 5.744 | 15.446 | −9.556 | 1.00 | 32.47 |
| 444 | N | GLN | A | 57 | 4.822 | 16.426 | −7.761 | 1.00 | 26.84 |
| 445 | CA | GLN | A | 57 | 5.947 | 17.356 | −7.690 | 1.00 | 25.59 |
| 446 | CB | GLN | A | 57 | 5.455 | 18.807 | −7.854 | 1.00 | 28.56 |
| 447 | CG | GLN | A | 57 | 4.630 | 19.349 | −6.716 | 1.00 | 33.11 |
| 448 | CD | GLN | A | 57 | 4.089 | 20.762 | −7.032 | 1.00 | 41.66 |
| 449 | OE1 | GLN | A | 57 | 3.819 | 21.563 | −6.126 | 1.00 | 40.37 |
| 450 | NE2 | GLN | A | 57 | 3.933 | 21.063 | −8.327 | 1.00 | 39.88 |
| 451 | C | GLN | A | 57 | 6.869 | 17.228 | −6.458 | 1.00 | 22.95 |
| 452 | O | GLN | A | 57 | 7.460 | 18.204 | −6.003 | 1.00 | 24.47 |
| 453 | N | GLY | A | 58 | 7.000 | 16.002 | −5.954 | 1.00 | 22.17 |
| 454 | CA | GLY | A | 58 | 7.871 | 15.743 | −4.843 | 1.00 | 18.50 |
| 455 | C | GLY | A | 58 | 7.246 | 15.913 | −3.473 | 1.00 | 19.05 |

-continued

Atomic coordinates of the native S8 structure
CRYST1 42.100 55.500 61.400 90.00 90.00 90.00

| ATOM | | RESIDUE | | | X | Y | Z | Occ | B |
|---|---|---|---|---|---|---|---|---|---|
| 456 | O | GLY | A | 58 | 6.213 | 16.547 | −3.300 | 1.00 | 18.74 |
| 457 | N | VAL | A | 59 | 7.932 | 15.306 | −2.522 | 1.00 | 19.84 |
| 458 | CA | VAL | A | 59 | 7.518 | 15.281 | −1.122 | 1.00 | 21.94 |
| 459 | CB | VAL | A | 59 | 7.141 | 13.809 | −0.757 | 1.00 | 19.26 |
| 460 | CG1 | VAL | A | 59 | 7.325 | 13.542 | 0.762 | 1.00 | 24.81 |
| 461 | CG2 | VAL | A | 59 | 5.699 | 13.552 | −1.174 | 1.00 | 23.20 |
| 462 | C | VAL | A | 59 | 8.615 | 15.811 | −0.202 | 1.00 | 17.61 |
| 463 | O | VAL | A | 59 | 9.806 | 15.744 | −0.494 | 1.00 | 18.55 |
| 464 | N | LEU | A | 60 | 8.214 | 16.469 | 0.894 | 1.00 | 17.50 |
| 465 | CA | LEU | A | 60 | 9.187 | 16.927 | 1.890 | 1.00 | 16.68 |
| 466 | CB | LEU | A | 60 | 8.917 | 18.375 | 2.301 | 1.00 | 20.18 |
| 467 | CG | LEU | A | 60 | 8.949 | 19.386 | 1.164 | 1.00 | 19.12 |
| 468 | CD1 | LEU | A | 60 | 8.627 | 20.755 | 1.751 | 1.00 | 21.10 |
| 469 | CD2 | LEU | A | 60 | 10.335 | 19.432 | 0.535 | 1.00 | 22.00 |
| 470 | C | LEU | A | 60 | 9.027 | 16.068 | 3.147 | 1.00 | 14.21 |
| 471 | O | LEU | A | 60 | 7.901 | 15.894 | 3.633 | 1.00 | 19.41 |
| 472 | N | ARG | A | 61 | 10.128 | 15.508 | 3.620 | 1.00 | 16.80 |
| 473 | CA | ARG | A | 61 | 10.062 | 14.670 | 4.820 | 1.00 | 14.82 |
| 474 | CB | ARG | A | 61 | 10.752 | 13.321 | 4.554 | 1.00 | 19.03 |
| 475 | CG | ARG | A | 61 | 10.862 | 12.440 | 5.794 | 1.00 | 20.10 |
| 476 | CD | ARG | A | 61 | 11.600 | 11.148 | 5.423 | 1.00 | 21.67 |
| 477 | NE | ARG | A | 61 | 10.792 | 10.381 | 4.498 | 1.00 | 25.73 |
| 478 | CZ | ARG | A | 61 | 11.312 | 9.660 | 3.515 | 1.00 | 24.65 |
| 479 | NH1 | ARG | A | 61 | 12.623 | 9.638 | 3.365 | 1.00 | 26.59 |
| 480 | NH2 | ARG | A | 61 | 10.517 | 8.958 | 2.713 | 1.00 | 23.07 |
| 481 | C | ARG | A | 61 | 10.764 | 15.456 | 5.909 | 1.00 | 15.91 |
| 482 | O | ARG | A | 61 | 11.903 | 15.814 | 5.788 | 1.00 | 19.77 |
| 483 | N | LEU | A | 62 | 9.995 | 15.842 | 6.924 | 1.00 | 15.80 |
| 484 | CA | LEU | A | 62 | 10.540 | 16.626 | 8.032 | 1.00 | 15.07 |
| 485 | CB | LEU | A | 62 | 9.526 | 17.710 | 8.412 | 1.00 | 14.09 |
| 486 | CG A | LEU | A | 62 | 9.612 | 19.002 | 7.538 | 0.50 | 11.86 |
| 487 | CG B | LEU | A | 62 | 9.092 | 18.710 | 7.313 | 0.50 | 19.47 |
| 488 | CD1A | LEU | A | 62 | 9.154 | 18.712 | 6.107 | 0.50 | 14.08 |
| 489 | CD1B | LEU | A | 62 | 8.156 | 19.737 | 7.881 | 0.50 | 15.45 |
| 490 | CD2A | LEU | A | 62 | 8.756 | 20.118 | 8.133 | 0.50 | 10.22 |
| 491 | CD2B | LEU | A | 62 | 10.308 | 19.396 | 6.747 | 0.50 | 22.00 |
| 492 | C | LEU | A | 62 | 10.755 | 15.708 | 9.237 | 1.00 | 13.03 |
| 493 | O | LEU | A | 62 | 9.854 | 14.957 | 9.588 | 1.00 | 19.09 |
| 494 | N | PHE | A | 63 | 11.912 | 15.853 | 9.852 | 1.00 | 15.26 |
| 495 | CA | PHE | A | 63 | 12.268 | 15.085 | 11.061 | 1.00 | 13.36 |
| 496 | CB | PHE | A | 63 | 13.692 | 14.580 | 10.949 | 1.00 | 17.23 |
| 497 | CG | PHE | A | 63 | 13.838 | 13.490 | 9.935 | 1.00 | 26.02 |
| 498 | CD1 | PHE | A | 63 | 13.993 | 13.809 | 8.587 | 1.00 | 24.64 |
| 499 | CD2 | PHE | A | 63 | 13.772 | 12.146 | 10.322 | 1.00 | 25.41 |
| 500 | CE1 | PHE | A | 63 | 14.086 | 12.806 | 7.606 | 1.00 | 34.29 |
| 501 | CE2 | PHE | A | 63 | 13.864 | 11.125 | 9.347 | 1.00 | 30.88 |
| 502 | CZ | PHE | A | 63 | 14.020 | 11.458 | 7.992 | 1.00 | 31.24 |
| 503 | C | PHE | A | 63 | 12.129 | 16.041 | 12.232 | 1.00 | 16.16 |
| 504 | O | PHE | A | 63 | 12.857 | 17.025 | 12.336 | 1.00 | 16.35 |
| 505 | N | LEU | A | 64 | 11.188 | 15.721 | 13.124 | 1.00 | 12.15 |
| 506 | CA | LEU | A | 64 | 10.949 | 16.628 | 14.265 | 1.00 | 13.95 |
| 507 | CB | LEU | A | 64 | 9.560 | 16.375 | 14.800 | 1.00 | 16.05 |
| 508 | CG | LEU | A | 64 | 8.443 | 16.513 | 13.753 | 1.00 | 15.55 |
| 509 | CD1 | LEU | A | 64 | 7.115 | 16.434 | 14.462 | 1.00 | 14.33 |
| 510 | CD2 | LEU | A | 64 | 8.494 | 17.868 | 12.999 | 1.00 | 18.42 |
| 511 | C | LEU | A | 64 | 11.995 | 16.495 | 15.341 | 1.00 | 16.79 |
| 512 | O | LEU | A | 64 | 12.764 | 15.541 | 15.331 | 1.00 | 16.10 |
| 513 | N | LYS | A | 65 | 12.018 | 17.455 | 16.268 | 1.00 | 14.93 |
| 514 | CA | LYS | A | 65 | 13.088 | 17.498 | 17.273 | 1.00 | 16.15 |
| 515 | CB | LYS | A | 65 | 13.953 | 18.742 | 17.031 | 1.00 | 16.36 |
| 516 | CG | LYS | A | 65 | 15.259 | 18.779 | 17.846 | 1.00 | 21.68 |
| 517 | CD | LYS | A | 65 | 16.138 | 19.944 | 17.424 | 1.00 | 24.61 |
| 518 | CE | LYS | A | 65 | 17.404 | 20.003 | 18.254 | 1.00 | 33.12 |
| 519 | NZ | LYS | A | 65 | 18.140 | 21.237 | 17.860 | 1.00 | 43.56 |
| 520 | C | LYS | A | 65 | 12.514 | 17.552 | 18.671 | 1.00 | 13.82 |
| 521 | O | LYS | A | 65 | 11.563 | 18.310 | 18.941 | 1.00 | 13.61 |
| 522 | N | TYR | A | 66 | 13.072 | 16.708 | 19.526 | 1.00 | 14.18 |
| 523 | CA | TYR | A | 66 | 12.679 | 16.640 | 20.929 | 1.00 | 14.37 |
| 524 | CB | TYR | A | 66 | 12.023 | 15.288 | 21.224 | 1.00 | 12.63 |
| 525 | CG | TYR | A | 66 | 10.835 | 15.085 | 20.291 | 1.00 | 13.29 |
| 526 | CD1 | TYR | A | 66 | 9.609 | 15.707 | 20.538 | 1.00 | 13.69 |
| 527 | CE1 | TYR | A | 66 | 8.549 | 15.590 | 19.660 | 1.00 | 10.82 |
| 528 | CD2 | TYR | A | 66 | 10.952 | 14.337 | 19.115 | 1.00 | 12.56 |
| 529 | CE2 | TYR | A | 66 | 9.886 | 14.225 | 18.218 | 1.00 | 14.32 |

-continued

Atomic coordinates of the native S8 structure
CRYST1 42.100 55.500 61.400 90.00 90.00 90.00

| ATOM | | RESIDUE | | | X | Y | Z | Occ | B |
|---|---|---|---|---|---|---|---|---|---|
| 530 | CZ | TYR | A | 66 | 8.683 | 14.849 | 18.492 | 1.00 | 10.23 |
| 531 | OH | TYR | A | 66 | 7.638 | 14.780 | 17.596 | 1.00 | 14.03 |
| 532 | C | TYR | A | 66 | 13.934 | 16.887 | 21.716 | 1.00 | 17.42 |
| 533 | O | TYR | A | 66 | 15.024 | 16.485 | 21.323 | 1.00 | 18.85 |
| 534 | N | GLY | A | 67 | 13.767 | 17.579 | 22.832 | 1.00 | 14.07 |
| 535 | CA | GLY | A | 67 | 14.908 | 17.936 | 23.635 | 1.00 | 16.44 |
| 536 | C | GLY | A | 67 | 15.520 | 16.825 | 24.458 | 1.00 | 12.83 |
| 537 | O | GLY | A | 67 | 15.195 | 15.612 | 24.419 | 1.00 | 14.24 |
| 538 | N | GLN | A | 68 | 16.444 | 17.296 | 25.294 | 1.00 | 19.98 |
| 539 | CA | GLN | A | 68 | 17.198 | 16.425 | 26.143 | 1.00 | 18.84 |
| 540 | CB | GLN | A | 68 | 18.177 | 17.301 | 26.948 | 1.00 | 23.70 |
| 541 | CG | GLN | A | 68 | 19.007 | 18.305 | 26.074 | 1.00 | 24.68 |
| 542 | CD | GLN | A | 68 | 19.915 | 17.585 | 25.083 | 1.00 | 30.35 |
| 543 | OE1 | GLN | A | 68 | 20.240 | 18.098 | 24.001 | 1.00 | 32.02 |
| 544 | NE2 | GLN | A | 68 | 20.316 | 16.394 | 25.446 | 1.00 | 25.11 |
| 545 | C | GLN | A | 68 | 16.310 | 15.597 | 27.098 | 1.00 | 19.88 |
| 546 | O | GLN | A | 68 | 16.651 | 14.507 | 27.503 | 1.00 | 20.76 |
| 547 | N | ASN | A | 69 | 15.154 | 16.139 | 27.467 | 1.00 | 14.22 |
| 548 | CA | ASN | A | 69 | 14.203 | 15.412 | 28.340 | 1.00 | 12.44 |
| 549 | CB | ASN | A | 69 | 13.869 | 16.247 | 29.555 | 1.00 | 10.77 |
| 550 | CG | ASN | A | 69 | 15.064 | 16.407 | 30.431 | 1.00 | 10.57 |
| 551 | OD1 | ASN | A | 69 | 15.457 | 15.425 | 31.071 | 1.00 | 14.00 |
| 552 | ND2 | ASN | A | 69 | 15.697 | 17.569 | 30.412 | 1.00 | 12.98 |
| 553 | C | ASN | A | 69 | 12.912 | 15.129 | 27.570 | 1.00 | 12.79 |
| 554 | O | ASN | A | 69 | 11.825 | 14.974 | 28.173 | 1.00 | 14.19 |
| 555 | N | ASP | A | 70 | 13.100 | 14.917 | 26.276 | 1.00 | 11.79 |
| 556 | CA | ASP | A | 70 | 12.025 | 14.595 | 25.313 | 1.00 | 12.02 |
| 557 | CB | ASP | A | 70 | 11.389 | 13.228 | 25.621 | 1.00 | 17.75 |
| 558 | CG | ASP | A | 70 | 12.406 | 12.087 | 25.591 | 1.00 | 19.88 |
| 559 | OD1 | ASP | A | 70 | 12.497 | 11.343 | 26.604 | 1.00 | 23.44 |
| 560 | OD2 | ASP | A | 70 | 13.099 | 11.949 | 24.563 | 1.00 | 21.00 |
| 561 | C | ASP | A | 70 | 10.937 | 15.657 | 25.224 | 1.00 | 13.39 |
| 562 | O | ASP | A | 70 | 9.861 | 15.382 | 24.666 | 1.00 | 13.36 |
| 563 | N | GLU | A | 71 | 11.201 | 16.863 | 25.704 | 1.00 | 10.62 |
| 564 | CA | GLU | A | 71 | 10.242 | 17.938 | 25.548 | 1.00 | 10.37 |
| 565 | CB | GLU | A | 71 | 10.604 | 19.104 | 26.511 | 1.00 | 14.47 |
| 566 | CG | GLU | A | 71 | 11.821 | 19.909 | 26.133 | 1.00 | 14.73 |
| 567 | CD | GLU | A | 71 | 13.156 | 19.327 | 26.526 | 1.00 | 14.61 |
| 568 | OE1 | GLU | A | 71 | 13.331 | 18.126 | 26.789 | 1.00 | 12.82 |
| 569 | OE2 | GLU | A | 71 | 14.102 | 20.160 | 26.520 | 1.00 | 27.36 |
| 570 | C | GLU | A | 71 | 10.200 | 18.408 | 24.092 | 1.00 | 12.85 |
| 571 | O | GLU | A | 71 | 11.197 | 18.298 | 23.355 | 1.00 | 13.50 |
| 572 | N | ARG | A | 72 | 9.047 | 18.872 | 23.638 | 1.00 | 13.46 |
| 573 | CA | ARG | A | 72 | 8.959 | 19.300 | 22.236 | 1.00 | 12.06 |
| 574 | CB | ARG | A | 72 | 7.489 | 19.429 | 21.832 | 1.00 | 14.51 |
| 575 | CG | ARG | A | 72 | 6.665 | 18.136 | 22.031 | 1.00 | 13.23 |
| 576 | CD | ARG | A | 72 | 5.223 | 18.386 | 21.673 | 1.00 | 13.43 |
| 577 | NE | ARG | A | 72 | 4.374 | 17.226 | 21.926 | 1.00 | 11.18 |
| 578 | CZ | ARG | A | 72 | 3.848 | 16.887 | 23.092 | 1.00 | 11.42 |
| 579 | NH1 | ARG | A | 72 | 4.113 | 17.649 | 24.169 | 1.00 | 13.06 |
| 580 | NH2 | ARG | A | 72 | 3.021 | 15.824 | 23.182 | 1.00 | 13.37 |
| 581 | C | ARG | A | 72 | 9.660 | 20.615 | 22.011 | 1.00 | 11.47 |
| 582 | O | ARG | A | 72 | 9.361 | 21.575 | 22.711 | 1.00 | 13.15 |
| 583 | N | VAL | A | 73 | 10.534 | 20.664 | 21.008 | 1.00 | 13.86 |
| 584 | CA | VAL | A | 73 | 11.256 | 21.876 | 20.721 | 1.00 | 14.77 |
| 585 | CB | VAL | A | 73 | 12.448 | 21.548 | 19.821 | 1.00 | 15.31 |
| 586 | CG1 | VAL | A | 73 | 13.058 | 22.833 | 19.241 | 1.00 | 20.54 |
| 587 | CG2 | VAL | A | 73 | 13.489 | 20.762 | 20.643 | 1.00 | 15.55 |
| 588 | C | VAL | A | 73 | 10.272 | 22.904 | 20.153 | 1.00 | 16.77 |
| 589 | O | VAL | A | 73 | 10.422 | 24.086 | 20.381 | 1.00 | 15.01 |
| 590 | N | ILE | A | 74 | 9.272 | 22.452 | 19.389 | 1.00 | 14.14 |
| 591 | CA | ILE | A | 74 | 8.235 | 23.348 | 18.905 | 1.00 | 12.14 |
| 592 | CB | ILE | A | 74 | 7.677 | 22.887 | 17.529 | 1.00 | 11.54 |
| 593 | CG2 | ILE | A | 74 | 6.406 | 23.691 | 17.186 | 1.00 | 12.82 |
| 594 | CG1 | ILE | A | 74 | 8.753 | 23.086 | 16.462 | 1.00 | 13.81 |
| 595 | CD1 | ILE | A | 74 | 8.334 | 22.451 | 15.075 | 1.00 | 12.99 |
| 596 | C | ILE | A | 74 | 7.066 | 23.344 | 19.903 | 1.00 | 13.54 |
| 597 | O | ILE | A | 74 | 6.579 | 22.289 | 20.291 | 1.00 | 15.74 |
| 598 | N | THR | A | 75 | 6.680 | 24.514 | 20.382 | 1.00 | 12.14 |
| 599 | CA | THR | A | 75 | 5.510 | 24.628 | 21.230 | 1.00 | 13.84 |
| 600 | CB | THR | A | 75 | 5.731 | 25.709 | 22.300 | 1.00 | 12.46 |
| 601 | OG1 | THR | A | 75 | 6.743 | 25.218 | 23.179 | 1.00 | 15.45 |
| 602 | CG2 | THR | A | 75 | 4.478 | 25.976 | 23.111 | 1.00 | 18.14 |
| 603 | C | THR | A | 75 | 4.297 | 24.916 | 20.337 | 1.00 | 14.98 |

-continued

Atomic coordinates of the native S8 structure
CRYST1 42.100 55.500 61.400 90.00 90.00 90.00

| ATOM | | RESIDUE | | | X | Y | Z | Occ | B |
|---|---|---|---|---|---|---|---|---|---|
| 604 | O | THR | A | 75 | 3.187 | 24.353 | 20.522 | 1.00 | 17.04 |
| 605 | N | GLY | A | 76 | 4.463 | 25.826 | 19.375 | 1.00 | 11.66 |
| 606 | CA | GLY | A | 76 | 3.343 | 26.123 | 18.507 | 1.00 | 12.65 |
| 607 | C | GLY | A | 76 | 3.684 | 26.762 | 17.177 | 1.00 | 12.76 |
| 608 | O | GLY | A | 76 | 4.806 | 27.221 | 16.964 | 1.00 | 13.34 |
| 609 | N | LEU | A | 77 | 2.713 | 26.755 | 16.279 | 1.00 | 12.96 |
| 610 | CA | LEU | A | 77 | 2.888 | 27.371 | 14.964 | 1.00 | 12.42 |
| 611 | CB | LEU | A | 77 | 3.072 | 26.322 | 13.842 | 1.00 | 14.28 |
| 612 | CG | LEU | A | 77 | 4.132 | 25.265 | 14.107 | 1.00 | 12.84 |
| 613 | CD1 | LEU | A | 77 | 3.401 | 24.050 | 14.640 | 1.00 | 17.27 |
| 614 | CD2 | LEU | A | 77 | 4.956 | 24.885 | 12.857 | 1.00 | 15.61 |
| 615 | C | LEU | A | 77 | 1.582 | 28.080 | 14.667 | 1.00 | 14.97 |
| 616 | O | LEU | A | 77 | 0.487 | 27.554 | 14.965 | 1.00 | 18.39 |
| 617 | N | LYS | A | 78 | 1.655 | 29.236 | 14.041 | 1.00 | 10.89 |
| 618 | CA | LYS | A | 78 | 0.416 | 29.955 | 13.757 | 1.00 | 10.92 |
| 619 | CB | LYS | A | 78 | 0.172 | 31.055 | 14.804 | 1.00 | 12.46 |
| 620 | CG | LYS | A | 78 | −1.154 | 31.763 | 14.642 | 1.00 | 15.96 |
| 621 | CD | LYS | A | 78 | −1.350 | 32.790 | 15.742 | 1.00 | 22.89 |
| 622 | CE | LYS | A | 78 | −2.622 | 33.607 | 15.540 | 1.00 | 29.30 |
| 623 | NZ | LYS | A | 78 | −2.558 | 34.367 | 14.253 | 1.00 | 38.34 |
| 624 | C | LYS | A | 78 | 0.513 | 30.619 | 12.386 | 1.00 | 12.82 |
| 625 | O | LYS | A | 78 | 1.510 | 31.253 | 12.080 | 1.00 | 12.93 |
| 626 | N | ARG | A | 79 | −0.475 | 30.382 | 11.519 | 1.00 | 11.89 |
| 627 | CA | ARG | A | 79 | −0.494 | 31.037 | 10.220 | 1.00 | 10.36 |
| 628 | CB | ARG | A | 79 | −1.506 | 30.340 | 9.317 | 1.00 | 11.45 |
| 629 | CG | ARG | A | 79 | −1.630 | 30.922 | 7.924 | 1.00 | 10.70 |
| 630 | CD | ARG | A | 79 | −0.428 | 30.458 | 7.065 | 1.00 | 11.44 |
| 631 | NE | ARG | A | 79 | −0.709 | 30.696 | 5.643 | 1.00 | 10.29 |
| 632 | CZ | ARG | A | 79 | −0.041 | 31.473 | 4.800 | 1.00 | 11.86 |
| 633 | NH1 | ARG | A | 79 | 1.003 | 32.198 | 5.180 | 1.00 | 10.82 |
| 634 | NH2 | ARG | A | 79 | −0.424 | 31.510 | 3.506 | 1.00 | 13.18 |
| 635 | C | ARG | A | 79 | −0.898 | 32.485 | 10.467 | 1.00 | 10.70 |
| 636 | O | ARG | A | 79 | −1.844 | 32.761 | 11.213 | 1.00 | 12.98 |
| 637 | N | ILE | A | 80 | −0.207 | 33.439 | 9.816 | 1.00 | 9.68 |
| 638 | CA | ILE | A | 80 | −0.498 | 34.872 | 10.004 | 1.00 | 11.10 |
| 639 | CB | ILE | A | 80 | 0.816 | 35.639 | 10.398 | 1.00 | 10.52 |
| 640 | CG2 | ILE | A | 80 | 0.556 | 37.170 | 10.588 | 1.00 | 10.50 |
| 641 | CG1 | ILE | A | 80 | 1.316 | 35.053 | 11.733 | 1.00 | 11.58 |
| 642 | CD1 | ILE | A | 80 | 0.359 | 35.297 | 12.974 | 1.00 | 15.29 |
| 643 | C | ILE | A | 80 | −1.136 | 35.413 | 8.772 | 1.00 | 12.17 |
| 644 | O | ILE | A | 80 | −2.353 | 35.571 | 8.728 | 1.00 | 11.92 |
| 645 | N | SER | A | 81 | −0.344 | 35.677 | 7.729 | 1.00 | 10.37 |
| 646 | CA | SER | A | 81 | −0.904 | 36.120 | 6.481 | 1.00 | 8.76 |
| 647 | CB | SER | A | 81 | 0.254 | 36.562 | 5.536 | 1.00 | 8.86 |
| 648 | OG | SER | A | 81 | −0.277 | 37.045 | 4.338 | 1.00 | 12.21 |
| 649 | C | SER | A | 81 | −1.681 | 34.906 | 5.922 | 1.00 | 10.94 |
| 650 | O | SER | A | 81 | −1.324 | 33.758 | 6.143 | 1.00 | 11.56 |
| 651 | N | LYS | A | 82 | −2.727 | 35.198 | 5.145 | 1.00 | 11.16 |
| 652 | CA | LYS | A | 82 | −3.548 | 34.134 | 4.538 | 1.00 | 12.55 |
| 653 | CB | LYS | A | 82 | −4.784 | 33.856 | 5.398 | 1.00 | 14.71 |
| 654 | CG | LYS | A | 82 | −4.396 | 33.348 | 6.774 | 1.00 | 12.80 |
| 655 | CD | LYS | A | 82 | −5.621 | 33.057 | 7.701 | 1.00 | 18.06 |
| 656 | CE | LYS | A | 82 | −5.073 | 32.703 | 9.096 | 1.00 | 21.61 |
| 657 | NZ | LYS | A | 82 | −6.120 | 32.420 | 10.082 | 1.00 | 32.93 |
| 658 | C | LYS | A | 82 | −3.989 | 34.584 | 3.184 | 1.00 | 12.61 |
| 659 | O | LYS | A | 82 | −3.998 | 35.755 | 2.894 | 1.00 | 13.82 |
| 660 | N | PRO | A | 83 | −4.357 | 33.629 | 2.302 | 1.00 | 14.58 |
| 661 | CD | PRO | A | 83 | −4.305 | 32.155 | 2.405 | 1.00 | 17.91 |
| 662 | CA | PRO | A | 83 | −4.794 | 34.083 | 0.974 | 1.00 | 14.56 |
| 663 | CB | PRO | A | 83 | −5.088 | 32.760 | 0.231 | 1.00 | 15.53 |
| 664 | CG | PRO | A | 83 | −4.146 | 31.756 | 0.948 | 1.00 | 16.19 |
| 665 | C | PRO | A | 83 | −6.014 | 34.979 | 1.077 | 1.00 | 14.00 |
| 666 | O | PRO | A | 83 | −6.964 | 34.658 | 1.776 | 1.00 | 16.77 |
| 667 | N | GLY | A | 84 | −5.918 | 36.115 | 0.383 | 1.00 | 15.18 |
| 668 | CA | GLY | A | 84 | −6.980 | 37.103 | 0.402 | 1.00 | 15.76 |
| 669 | C | GLY | A | 84 | −7.022 | 37.943 | 1.657 | 1.00 | 15.78 |
| 670 | O | GLY | A | 84 | −7.873 | 38.827 | 1.783 | 1.00 | 16.65 |
| 671 | N | LEU | A | 85 | −6.110 | 37.681 | 2.602 | 1.00 | 14.27 |
| 672 | CA | LEU | A | 85 | −6.075 | 38.416 | 3.879 | 1.00 | 12.30 |
| 673 | CB | LEU | A | 85 | −6.739 | 37.573 | 4.960 | 1.00 | 13.25 |
| 674 | CG | LEU | A | 85 | −8.234 | 37.251 | 4.729 | 1.00 | 13.75 |
| 675 | CD1 | LEU | A | 85 | −8.639 | 36.120 | 5.626 | 1.00 | 15.04 |
| 676 | CD2 | LEU | A | 85 | −9.052 | 38.489 | 5.038 | 1.00 | 18.34 |
| 677 | C | LEU | A | 85 | −4.570 | 38.552 | 4.204 | 1.00 | 11.17 |

-continued

Atomic coordinates of the native S8 structure
CRYST1 42.100 55.500 61.400 90.00 90.00 90.00

| ATOM | | RESIDUE | | | X | Y | Z | Occ | B |
|---|---|---|---|---|---|---|---|---|---|
| 678 | O | LEU | A | 85 | −4.102 | 38.096 | 5.231 | 1.00 | 12.96 |
| 679 | N | ARG | A | 86 | −3.890 | 39.225 | 3.306 | 1.00 | 13.55 |
| 680 | CA | ARG | A | 86 | −2.425 | 39.357 | 3.426 | 1.00 | 11.95 |
| 681 | CB | ARG | A | 86 | −1.859 | 39.999 | 2.156 | 1.00 | 14.49 |
| 682 | CG | ARG | A | 86 | −0.344 | 40.227 | 2.136 | 1.00 | 17.98 |
| 683 | CD | ARG | A | 86 | 0.236 | 40.268 | 0.644 | 1.00 | 17.43 |
| 684 | NE | ARG | A | 86 | 1.670 | 40.580 | 0.600 | 1.00 | 18.04 |
| 685 | CZ | ARG | A | 86 | 2.156 | 41.811 | 0.538 | 1.00 | 21.23 |
| 686 | NH1 | ARG | A | 86 | 1.322 | 42.858 | 0.504 | 1.00 | 22.22 |
| 687 | NH2 | ARG | A | 86 | 3.468 | 42.009 | 0.510 | 1.00 | 18.96 |
| 688 | C | ARG | A | 86 | −2.042 | 40.197 | 4.606 | 1.00 | 13.56 |
| 689 | O | ARG | A | 86 | −2.766 | 41.169 | 4.971 | 1.00 | 14.01 |
| 690 | N | VAL | A | 87 | −0.926 | 39.783 | 5.238 | 1.00 | 9.25 |
| 691 | CA | VAL | A | 87 | −0.338 | 40.559 | 6.339 | 1.00 | 9.09 |
| 692 | CB | VAL | A | 87 | −0.229 | 39.735 | 7.584 | 1.00 | 8.47 |
| 693 | CG1 | VAL | A | 87 | 0.553 | 40.487 | 8.676 | 1.00 | 12.12 |
| 694 | CG2 | VAL | A | 87 | −1.661 | 39.516 | 8.105 | 1.00 | 11.24 |
| 695 | C | VAL | A | 87 | 1.077 | 40.956 | 5.919 | 1.00 | 10.79 |
| 696 | O | VAL | A | 87 | 1.913 | 40.081 | 5.739 | 1.00 | 10.09 |
| 697 | N | TYR | A | 88 | 1.297 | 42.255 | 5.750 | 1.00 | 15.79 |
| 698 | CA | TYR | A | 88 | 2.605 | 42.825 | 5.405 | 1.00 | 15.47 |
| 699 | CB | TYR | A | 88 | 2.498 | 43.608 | 4.112 | 1.00 | 12.62 |
| 700 | CG | TYR | A | 88 | 3.703 | 44.530 | 3.834 | 1.00 | 17.48 |
| 701 | CD1 | TYR | A | 88 | 4.906 | 44.009 | 3.309 | 1.00 | 14.80 |
| 702 | CE1 | TYR | A | 88 | 6.012 | 44.852 | 3.105 | 1.00 | 18.42 |
| 703 | CD2 | TYR | A | 88 | 3.642 | 45.892 | 4.144 | 1.00 | 20.80 |
| 704 | CE2 | TYR | A | 88 | 4.735 | 46.720 | 3.944 | 1.00 | 20.23 |
| 705 | CZ | TYR | A | 88 | 5.907 | 46.198 | 3.427 | 1.00 | 20.55 |
| 706 | OH | TYR | A | 88 | 6.987 | 47.068 | 3.190 | 1.00 | 24.23 |
| 707 | C | TYR | A | 88 | 3.057 | 43.742 | 6.518 | 1.00 | 16.01 |
| 708 | O | TYR | A | 88 | 2.284 | 44.560 | 7.020 | 1.00 | 15.46 |
| 709 | N | ALA | A | 89 | 4.293 | 43.540 | 6.975 | 1.00 | 11.50 |
| 710 | CA | ALA | A | 89 | 4.864 | 44.395 | 8.011 | 1.00 | 10.38 |
| 711 | CB | ALA | A | 89 | 5.488 | 43.586 | 9.101 | 1.00 | 14.07 |
| 712 | C | ALA | A | 89 | 5.936 | 45.230 | 7.349 | 1.00 | 16.04 |
| 713 | O | ALA | A | 89 | 6.851 | 44.668 | 6.748 | 1.00 | 16.15 |
| 714 | N | LYS | A | 90 | 5.822 | 46.562 | 7.419 | 1.00 | 16.05 |
| 715 | CA | LYS | A | 90 | 6.889 | 47.351 | 6.860 | 1.00 | 18.86 |
| 716 | CB | LYS | A | 90 | 6.501 | 48.834 | 6.782 | 1.00 | 17.60 |
| 717 | CG | LYS | A | 90 | 6.214 | 49.437 | 8.122 | 1.00 | 21.58 |
| 718 | CD | LYS | A | 90 | 6.033 | 50.969 | 7.971 | 1.00 | 33.81 |
| 719 | CE | LYS | A | 90 | 4.588 | 51.376 | 8.089 | 1.00 | 40.08 |
| 720 | NZ | LYS | A | 90 | 4.469 | 52.869 | 8.168 | 1.00 | 44.32 |
| 721 | C | LYS | A | 90 | 8.098 | 47.144 | 7.787 | 1.00 | 17.54 |
| 722 | O | LYS | A | 90 | 7.966 | 46.636 | 8.904 | 1.00 | 16.76 |
| 723 | N | ALA | A | 91 | 9.278 | 47.576 | 7.337 | 1.00 | 16.64 |
| 724 | CA | ALA | A | 91 | 10.479 | 47.366 | 8.128 | 1.00 | 18.67 |
| 725 | CB | ALA | A | 91 | 11.655 | 48.041 | 7.427 | 1.00 | 18.91 |
| 726 | C | ALA | A | 91 | 10.442 | 47.765 | 9.606 | 1.00 | 18.05 |
| 727 | O | ALA | A | 91 | 10.855 | 47.001 | 10.488 | 1.00 | 17.91 |
| 728 | N | SER | A | 92 | 9.917 | 48.942 | 9.896 | 1.00 | 23.72 |
| 729 | CA | SER | A | 92 | 9.857 | 49.403 | 11.285 | 1.00 | 23.89 |
| 730 | CB | SER | A | 92 | 9.585 | 50.926 | 11.318 | 1.00 | 26.05 |
| 731 | OG | SER | A | 92 | 8.330 | 51.249 | 10.729 | 1.00 | 26.98 |
| 732 | C | SER | A | 92 | 8.804 | 48.705 | 12.137 | 1.00 | 25.38 |
| 733 | O | SER | A | 92 | 8.788 | 48.889 | 13.352 | 1.00 | 27.23 |
| 734 | N | GLU | A | 93 | 7.916 | 47.913 | 11.516 | 1.00 | 20.29 |
| 735 | CA | GLU | A | 93 | 6.842 | 47.260 | 12.254 | 1.00 | 21.56 |
| 736 | CB | GLU | A | 93 | 5.502 | 47.560 | 11.571 | 1.00 | 19.70 |
| 737 | CG | GLU | A | 93 | 5.106 | 49.036 | 11.582 | 1.00 | 28.45 |
| 738 | CD | GLU | A | 93 | 5.101 | 49.629 | 12.970 | 1.00 | 29.50 |
| 739 | OE1 | GLU | A | 93 | 4.379 | 49.096 | 13.837 | 1.00 | 26.15 |
| 740 | OE2 | GLU | A | 93 | 5.827 | 50.621 | 13.210 | 1.00 | 39.50 |
| 741 | C | GLU | A | 93 | 7.049 | 45.751 | 12.307 | 1.00 | 17.97 |
| 742 | O | GLU | A | 93 | 6.153 | 45.012 | 12.704 | 1.00 | 18.18 |
| 743 | N | MET | A | 94 | 8.238 | 45.313 | 11.919 | 1.00 | 18.42 |
| 744 | CA | MET | A | 94 | 8.559 | 43.884 | 11.902 | 1.00 | 15.60 |
| 745 | CB | MET | A | 94 | 10.022 | 43.738 | 11.450 | 1.00 | 17.32 |
| 746 | CG | MET | A | 94 | 10.506 | 42.298 | 11.261 | 1.00 | 14.83 |
| 747 | SD | MET | A | 94 | 9.488 | 41.315 | 10.140 | 1.00 | 15.25 |
| 748 | CE | MET | A | 94 | 9.452 | 42.297 | 8.736 | 1.00 | 13.31 |
| 749 | C | MET | A | 94 | 8.303 | 43.333 | 13.298 | 1.00 | 18.99 |
| 750 | O | MET | A | 94 | 9.006 | 43.707 | 14.242 | 1.00 | 21.10 |
| 751 | N | PRO | A | 95 | 7.276 | 42.467 | 13.462 | 1.00 | 16.98 |

-continued

Atomic coordinates of the native S8 structure
CRYST1 42.100 55.500 61.400 90.00 90.00 90.00

| ATOM | | RESIDUE | | | X | Y | Z | Occ | B |
|---|---|---|---|---|---|---|---|---|---|
| 752 | CD | PRO | A | 95 | 6.432 | 41.893 | 12.376 | 1.00 | 15.20 |
| 753 | CA | PRO | A | 95 | 6.904 | 41.888 | 14.764 | 1.00 | 16.05 |
| 754 | CB | PRO | A | 95 | 5.548 | 41.244 | 14.471 | 1.00 | 18.87 |
| 755 | CG | PRO | A | 95 | 5.759 | 40.680 | 13.042 | 1.00 | 18.12 |
| 756 | C | PRO | A | 95 | 7.883 | 40.914 | 15.385 | 1.00 | 19.74 |
| 757 | O | PRO | A | 95 | 8.725 | 40.319 | 14.679 | 1.00 | 18.41 |
| 758 | N | LYS | A | 96 | 7.829 | 40.810 | 16.719 | 1.00 | 20.86 |
| 759 | CA | LYS | A | 96 | 8.642 | 39.817 | 17.439 | 1.00 | 15.85 |
| 760 | CB | LYS | A | 96 | 9.493 | 40.412 | 18.582 | 1.00 | 20.02 |
| 761 | CG | LYS | A | 96 | 10.828 | 41.009 | 18.113 | 1.00 | 23.65 |
| 762 | CD | LYS | A | 96 | 11.659 | 41.458 | 19.306 | 1.00 | 26.92 |
| 763 | CE | LYS | A | 96 | 13.005 | 41.929 | 18.852 | 1.00 | 31.82 |
| 764 | NZ | LYS | A | 96 | 13.814 | 42.480 | 19.977 | 1.00 | 38.15 |
| 765 | C | LYS | A | 96 | 7.640 | 38.861 | 18.013 | 1.00 | 17.68 |
| 766 | O | LYS | A | 96 | 6.505 | 39.237 | 18.327 | 1.00 | 20.06 |
| 767 | N | VAL | A | 97 | 8.048 | 37.599 | 18.089 | 1.00 | 15.40 |
| 768 | CA | VAL | A | 97 | 7.198 | 36.538 | 18.615 | 1.00 | 13.12 |
| 769 | CB | VAL | A | 97 | 7.302 | 35.297 | 17.676 | 1.00 | 14.86 |
| 770 | CG1 | VAL | A | 97 | 6.486 | 34.125 | 18.179 | 1.00 | 18.80 |
| 771 | CG2 | VAL | A | 97 | 6.754 | 35.714 | 16.258 | 1.00 | 17.83 |
| 772 | C | VAL | A | 97 | 7.750 | 36.254 | 20.009 | 1.00 | 16.78 |
| 773 | O | VAL | A | 97 | 8.926 | 35.882 | 20.157 | 1.00 | 16.90 |
| 774 | N | LEU | A | 98 | 6.873 | 36.385 | 21.019 | 1.00 | 18.18 |
| 775 | CA | LEU | A | 98 | 7.280 | 36.214 | 22.436 | 1.00 | 19.32 |
| 776 | CB | LEU | A | 98 | 7.452 | 34.717 | 22.818 | 1.00 | 24.20 |
| 777 | CG | LEU | A | 98 | 6.204 | 33.827 | 22.670 | 1.00 | 25.60 |
| 778 | CD1 | LEU | A | 98 | 6.543 | 32.388 | 23.109 | 1.00 | 22.47 |
| 779 | CD2 | LEU | A | 98 | 5.032 | 34.418 | 23.497 | 1.00 | 22.24 |
| 780 | C | LEU | A | 98 | 8.534 | 37.002 | 22.768 | 1.00 | 22.57 |
| 781 | O | LEU | A | 98 | 9.491 | 36.489 | 23.376 | 1.00 | 21.80 |
| 782 | N | ASN | A | 99 | 8.528 | 38.265 | 22.346 | 1.00 | 20.95 |
| 783 | CA | ASN | A | 99 | 9.639 | 39.167 | 22.588 | 1.00 | 21.68 |
| 784 | CB | ASN | A | 99 | 9.751 | 39.444 | 24.102 | 1.00 | 20.16 |
| 785 | CG | ASN | A | 99 | 8.731 | 40.461 | 24.605 | 1.00 | 28.35 |
| 786 | OD1 | ASN | A | 99 | 8.645 | 40.709 | 25.808 | 1.00 | 29.89 |
| 787 | ND2 | ASN | A | 99 | 7.955 | 41.054 | 23.699 | 1.00 | 22.63 |
| 788 | C | ASN | A | 99 | 10.985 | 38.682 | 22.028 | 1.00 | 21.34 |
| 789 | O | ASN | A | 99 | 12.037 | 39.161 | 22.432 | 1.00 | 22.61 |
| 790 | N | GLY | A | 100 | 10.971 | 37.747 | 21.066 | 1.00 | 16.11 |
| 791 | CA | GLY | A | 100 | 12.221 | 37.306 | 20.487 | 1.00 | 18.10 |
| 792 | C | GLY | A | 100 | 12.486 | 35.832 | 20.738 | 1.00 | 16.81 |
| 793 | O | GLY | A | 100 | 13.424 | 35.276 | 20.175 | 1.00 | 18.53 |
| 794 | N | LEU | A | 101 | 11.650 | 35.186 | 21.553 | 1.00 | 18.12 |
| 795 | CA | LEU | A | 101 | 11.877 | 33.774 | 21.866 | 1.00 | 17.08 |
| 796 | CB | LEU | A | 101 | 11.258 | 33.369 | 23.223 | 1.00 | 16.32 |
| 797 | CG | LEU | A | 101 | 11.960 | 33.969 | 24.458 | 1.00 | 19.19 |
| 798 | CD1 | LEU | A | 101 | 11.193 | 33.475 | 25.709 | 1.00 | 21.03 |
| 799 | CD2 | LEU | A | 101 | 13.398 | 33.542 | 24.543 | 1.00 | 23.46 |
| 800 | C | LEU | A | 101 | 11.378 | 32.857 | 20.773 | 1.00 | 16.32 |
| 801 | O | LEU | A | 101 | 11.834 | 31.726 | 20.668 | 1.00 | 16.93 |
| 802 | N | GLY | A | 102 | 10.406 | 33.340 | 19.991 | 1.00 | 15.32 |
| 803 | CA | GLY | A | 102 | 9.966 | 32.567 | 18.850 | 1.00 | 11.91 |
| 804 | C | GLY | A | 102 | 10.426 | 33.317 | 17.598 | 1.00 | 14.50 |
| 805 | O | GLY | A | 102 | 11.206 | 34.227 | 17.686 | 1.00 | 14.08 |
| 806 | N | ILE | A | 103 | 9.992 | 32.878 | 16.428 | 1.00 | 11.41 |
| 807 | CA | ILE | A | 103 | 10.360 | 33.553 | 15.196 | 1.00 | 10.51 |
| 808 | CB | ILE | A | 103 | 11.344 | 32.716 | 14.297 | 1.00 | 12.15 |
| 809 | CG2 | ILE | A | 103 | 12.684 | 32.538 | 15.031 | 1.00 | 15.59 |
| 810 | CG1 | ILE | A | 103 | 10.759 | 31.343 | 13.931 | 1.00 | 13.72 |
| 811 | CD1 | ILE | A | 103 | 11.704 | 30.512 | 13.005 | 1.00 | 15.76 |
| 812 | C | ILE | A | 103 | 9.142 | 33.780 | 14.332 | 1.00 | 11.21 |
| 813 | O | ILE | A | 103 | 8.162 | 33.046 | 14.406 | 1.00 | 13.44 |
| 814 | N | ALA | A | 104 | 9.206 | 34.835 | 13.529 | 1.00 | 9.11 |
| 815 | CA | ALA | A | 104 | 8.196 | 35.037 | 12.480 | 1.00 | 11.44 |
| 816 | CB | ALA | A | 104 | 7.731 | 36.490 | 12.379 | 1.00 | 12.52 |
| 817 | C | ALA | A | 104 | 8.937 | 34.660 | 11.192 | 1.00 | 14.21 |
| 818 | O | ALA | A | 104 | 10.139 | 34.916 | 11.030 | 1.00 | 12.74 |
| 819 | N | LEU | A | 105 | 8.229 | 34.008 | 10.271 | 1.00 | 10.13 |
| 820 | CA | LEU | A | 105 | 8.820 | 33.679 | 8.953 | 1.00 | 9.95 |
| 821 | CB | LEU | A | 105 | 8.331 | 32.332 | 8.470 | 1.00 | 9.52 |
| 822 | CG | LEU | A | 105 | 8.710 | 31.200 | 9.432 | 1.00 | 17.45 |
| 823 | CD1 | LEU | A | 105 | 8.104 | 29.878 | 8.932 | 1.00 | 19.68 |
| 824 | CD2 | LEU | A | 105 | 10.206 | 31.078 | 9.536 | 1.00 | 23.41 |
| 825 | C | LEU | A | 105 | 8.283 | 34.800 | 8.034 | 1.00 | 9.90 |

-continued

Atomic coordinates of the native S8 structure
CRYST1 42.100 55.500 61.400 90.00 90.00 90.00

| ATOM | | RESIDUE | | | X | Y | Z | Occ | B |
|---|---|---|---|---|---|---|---|---|---|
| 826 | O | LEU | A | 105 | 7.099 | 35.097 | 7.995 | 1.00 | 10.55 |
| 827 | N | VAL | A | 106 | 9.221 | 35.455 | 7.327 | 1.00 | 9.62 |
| 828 | CA | VAL | A | 106 | 8.912 | 36.651 | 6.531 | 1.00 | 10.35 |
| 829 | CB | VAL | A | 106 | 9.725 | 37.845 | 7.062 | 1.00 | 12.20 |
| 830 | CG1 | VAL | A | 106 | 9.395 | 39.124 | 6.314 | 1.00 | 9.56 |
| 831 | CG2 | VAL | A | 106 | 9.476 | 37.991 | 8.604 | 1.00 | 12.36 |
| 832 | C | VAL | A | 106 | 9.251 | 36.425 | 5.066 | 1.00 | 12.29 |
| 833 | O | VAL | A | 106 | 10.368 | 36.045 | 4.741 | 1.00 | 11.23 |
| 834 | N | SER | A | 107 | 8.272 | 36.627 | 4.169 | 1.00 | 10.90 |
| 835 | CA | SER | A | 107 | 8.526 | 36.443 | 2.729 | 1.00 | 12.19 |
| 836 | CB | SER | A | 107 | 7.240 | 36.034 | 1.994 | 1.00 | 14.23 |
| 837 | OG | SER | A | 107 | 7.570 | 35.730 | 0.639 | 1.00 | 16.39 |
| 838 | C | SER | A | 107 | 8.985 | 37.782 | 2.187 | 1.00 | 10.58 |
| 839 | O | SER | A | 107 | 8.270 | 38.789 | 2.292 | 1.00 | 11.06 |
| 840 | N | THR | A | 108 | 10.204 | 37.818 | 1.621 | 1.00 | 10.16 |
| 841 | CA | THR | A | 108 | 10.782 | 39.049 | 1.128 | 1.00 | 10.99 |
| 842 | CB | THR | A | 108 | 12.017 | 39.513 | 1.947 | 1.00 | 10.30 |
| 843 | OG1 | THR | A | 108 | 13.142 | 38.642 | 1.616 | 1.00 | 11.31 |
| 844 | CG2 | THR | A | 108 | 11.749 | 39.445 | 3.451 | 1.00 | 11.47 |
| 845 | C | THR | A | 108 | 11.257 | 38.891 | −0.286 | 1.00 | 9.32 |
| 846 | O | THR | A | 108 | 11.201 | 37.803 | −0.875 | 1.00 | 11.44 |
| 847 | N | SER | A | 109 | 11.750 | 40.012 | −0.856 | 1.00 | 10.95 |
| 848 | CA | SER | A | 109 | 12.223 | 39.937 | −2.247 | 1.00 | 12.01 |
| 849 | CB | SER | A | 109 | 12.499 | 41.334 | −2.759 | 1.00 | 13.38 |
| 850 | OG | SER | A | 109 | 13.522 | 41.854 | −1.944 | 1.00 | 19.19 |
| 851 | C | SER | A | 109 | 13.462 | 39.058 | −2.426 | 1.00 | 11.60 |
| 852 | O | SER | A | 109 | 13.771 | 38.660 | −3.551 | 1.00 | 12.69 |
| 853 | N | GLU | A | 110 | 14.123 | 38.683 | −1.328 | 1.00 | 11.99 |
| 854 | CA | GLU | A | 110 | 15.301 | 37.802 | −1.372 | 1.00 | 14.00 |
| 855 | CB A | GLU | A | 110 | 16.487 | 38.458 | −0.640 | 0.50 | 15.92 |
| 856 | CB B | GLU | A | 110 | 16.447 | 38.405 | −0.513 | 0.50 | 13.21 |
| 857 | CG A | GLU | A | 110 | 17.317 | 39.438 | −1.538 | 0.50 | 20.73 |
| 858 | CG B | GLU | A | 110 | 16.924 | 39.808 | −0.907 | 0.50 | 12.55 |
| 859 | CD A | GLU | A | 110 | 18.087 | 38.755 | −2.692 | 0.50 | 20.98 |
| 860 | CD B | GLU | A | 110 | 18.264 | 40.237 | −0.267 | 0.50 | 16.47 |
| 861 | OE1A | GLU | A | 110 | 17.423 | 38.218 | −3.630 | 0.50 | 14.75 |
| 862 | OE1B | GLU | A | 110 | 19.328 | 39.694 | −0.639 | 0.50 | 20.77 |
| 863 | OE2A | GLU | A | 110 | 19.368 | 38.735 | −2.674 | 0.50 | 20.13 |
| 864 | OE2B | GLU | A | 110 | 18.247 | 41.142 | 0.605 | 0.50 | 21.01 |
| 865 | C | GLU | A | 110 | 14.998 | 36.391 | −0.844 | 1.00 | 15.80 |
| 866 | O | GLU | A | 110 | 15.924 | 35.574 | −0.683 | 1.00 | 17.76 |
| 867 | N | GLY | A | 111 | 13.708 | 36.067 | −0.653 | 1.00 | 11.83 |
| 868 | CA | GLY | A | 111 | 13.328 | 34.772 | −0.100 | 1.00 | 13.35 |
| 869 | C | GLY | A | 111 | 12.771 | 34.903 | 1.322 | 1.00 | 10.68 |
| 870 | O | GLY | A | 111 | 12.666 | 36.014 | 1.881 | 1.00 | 11.13 |
| 871 | N | VAL | A | 112 | 12.470 | 33.747 | 1.924 | 1.00 | 10.43 |
| 872 | CA | VAL | A | 112 | 11.939 | 33.694 | 3.282 | 1.00 | 11.99 |
| 873 | CB | VAL | A | 112 | 11.179 | 32.365 | 3.517 | 1.00 | 11.37 |
| 874 | CG1 | VAL | A | 112 | 10.583 | 32.363 | 4.913 | 1.00 | 14.43 |
| 875 | CG2 | VAL | A | 112 | 10.018 | 32.256 | 2.519 | 1.00 | 11.74 |
| 876 | C | VAL | A | 112 | 13.097 | 33.793 | 4.283 | 1.00 | 10.65 |
| 877 | O | VAL | A | 112 | 14.121 | 33.141 | 4.102 | 1.00 | 14.31 |
| 878 | N | ILE | A | 113 | 12.919 | 34.676 | 5.252 | 1.00 | 11.14 |
| 879 | CA | ILE | A | 113 | 13.885 | 34.942 | 6.300 | 1.00 | 12.82 |
| 880 | CB | ILE | A | 113 | 14.714 | 36.232 | 6.040 | 1.00 | 12.46 |
| 881 | CG2 | ILE | A | 113 | 15.514 | 36.051 | 4.737 | 1.00 | 14.34 |
| 882 | CG1 | ILE | A | 113 | 13.839 | 37.499 | 6.046 | 1.00 | 13.84 |
| 883 | CD1 | ILE | A | 113 | 14.689 | 38.841 | 5.855 | 1.00 | 12.60 |
| 884 | C | ILE | A | 113 | 13.172 | 35.080 | 7.629 | 1.00 | 12.25 |
| 885 | O | ILE | A | 113 | 11.940 | 35.138 | 7.670 | 1.00 | 12.19 |
| 886 | N | THR | A | 114 | 13.920 | 35.103 | 8.727 | 1.00 | 11.55 |
| 887 | CA | THR | A | 114 | 13.271 | 35.294 | 10.024 | 1.00 | 12.41 |
| 888 | CB | THR | A | 114 | 14.165 | 34.776 | 11.162 | 1.00 | 11.80 |
| 889 | OG1 | THR | A | 114 | 15.400 | 35.530 | 11.176 | 1.00 | 15.64 |
| 890 | CG2 | THR | A | 114 | 14.494 | 33.307 | 10.927 | 1.00 | 14.91 |
| 891 | C | THR | A | 114 | 13.080 | 36.791 | 10.297 | 1.00 | 11.81 |
| 892 | O | THR | A | 114 | 13.647 | 37.683 | 9.603 | 1.00 | 11.26 |
| 893 | N | ASP | A | 115 | 12.274 | 37.124 | 11.291 | 1.00 | 11.36 |
| 894 | CA | ASP | A | 115 | 12.113 | 38.521 | 11.660 | 1.00 | 10.96 |
| 895 | CB | ASP | A | 115 | 11.017 | 38.718 | 12.737 | 1.00 | 12.92 |
| 896 | CG | ASP | A | 115 | 11.284 | 37.910 | 13.990 | 1.00 | 14.65 |
| 897 | OD1 | ASP | A | 115 | 11.391 | 36.689 | 13.875 | 1.00 | 15.57 |
| 898 | OD2 | ASP | A | 115 | 11.430 | 38.516 | 15.085 | 1.00 | 14.56 |
| 899 | C | ASP | A | 115 | 13.435 | 39.122 | 12.145 | 1.00 | 12.23 |

-continued

Atomic coordinates of the native S8 structure
CRYST1 42.100 55.500 61.400 90.00 90.00 90.00

| ATOM | | RESIDUE | | | X | Y | Z | Occ | B |
|---|---|---|---|---|---|---|---|---|---|
| 900 | O | ASP | A | 115 | 13.668 | 40.271 | 11.888 | 1.00 | 13.08 |
| 901 | N | LYS | A | 116 | 14.268 | 38.332 | 12.815 | 1.00 | 12.96 |
| 902 | CA | LYS | A | 116 | 15.574 | 38.838 | 13.282 | 1.00 | 14.53 |
| 903 | CB | LYS | A | 116 | 16.274 | 37.743 | 14.104 | 1.00 | 16.96 |
| 904 | CG | LYS | A | 116 | 17.641 | 38.212 | 14.659 | 1.00 | 24.00 |
| 905 | CD | LYS | A | 116 | 18.226 | 37.192 | 15.611 | 1.00 | 25.03 |
| 906 | CE | LYS | A | 116 | 18.633 | 35.953 | 14.896 | 1.00 | 38.30 |
| 907 | NZ | LYS | A | 116 | 19.573 | 36.227 | 13.785 | 1.00 | 42.73 |
| 908 | C | LYS | A | 116 | 16.418 | 39.234 | 12.065 | 1.00 | 14.20 |
| 909 | O | LYS | A | 116 | 17.060 | 40.305 | 12.037 | 1.00 | 15.23 |
| 910 | N | GLU | A | 117 | 16.416 | 38.400 | 11.035 | 1.00 | 14.02 |
| 911 | CA | GLU | A | 117 | 17.200 | 38.697 | 9.836 | 1.00 | 11.91 |
| 912 | CB | GLU | A | 117 | 17.287 | 37.465 | 8.956 | 1.00 | 12.83 |
| 913 | CG | GLU | A | 117 | 18.125 | 37.658 | 7.727 | 1.00 | 15.14 |
| 914 | CD | GLU | A | 117 | 19.629 | 37.853 | 8.066 | 1.00 | 20.85 |
| 915 | OE1 | GLU | A | 117 | 20.090 | 37.378 | 9.121 | 1.00 | 23.10 |
| 916 | OE2 | GLU | A | 117 | 20.312 | 38.479 | 7.263 | 1.00 | 21.25 |
| 917 | C | GLU | A | 117 | 16.576 | 39.865 | 9.084 | 1.00 | 15.14 |
| 918 | O | GLU | A | 117 | 17.291 | 40.687 | 8.509 | 1.00 | 14.51 |
| 919 | N | ALA | A | 118 | 15.236 | 39.972 | 9.067 | 1.00 | 12.70 |
| 920 | CA | ALA | A | 118 | 14.617 | 41.104 | 8.406 | 1.00 | 11.31 |
| 921 | CB | ALA | A | 118 | 13.038 | 40.949 | 8.428 | 1.00 | 12.66 |
| 922 | C | ALA | A | 118 | 15.021 | 42.426 | 9.092 | 1.00 | 12.16 |
| 923 | O | ALA | A | 118 | 15.262 | 43.422 | 8.399 | 1.00 | 12.80 |
| 924 | N | ARG | A | 119 | 15.059 | 42.443 | 10.411 | 1.00 | 13.29 |
| 925 | CA | ARG | A | 119 | 15.495 | 43.646 | 11.129 | 1.00 | 15.43 |
| 926 | CB | ARG | A | 119 | 15.282 | 43.522 | 12.639 | 1.00 | 16.04 |
| 927 | CG | ARG | A | 119 | 13.807 | 43.603 | 13.028 | 1.00 | 19.01 |
| 928 | CD A | ARG | A | 119 | 13.591 | 43.740 | 14.511 | 0.50 | 19.48 |
| 929 | CD B | ARG | A | 119 | 13.719 | 43.584 | 14.582 | 0.50 | 20.49 |
| 930 | NE A | ARG | A | 119 | 13.824 | 42.462 | 15.138 | 0.50 | 18.80 |
| 931 | NE B | ARG | A | 119 | 12.375 | 43.210 | 14.988 | 0.50 | 21.60 |
| 932 | CZ A | ARG | A | 119 | 12.932 | 41.468 | 15.209 | 0.50 | 14.46 |
| 933 | CZ B | ARG | A | 119 | 11.972 | 41.953 | 15.129 | 0.50 | 23.90 |
| 934 | NH1A | ARG | A | 119 | 11.689 | 41.594 | 14.704 | 0.50 | 13.01 |
| 935 | NH1B | ARG | A | 119 | 12.826 | 40.949 | 14.943 | 0.50 | 23.65 |
| 936 | NH2A | ARG | A | 119 | 13.317 | 40.329 | 15.745 | 0.50 | 15.29 |
| 937 | NH2B | ARG | A | 119 | 10.697 | 41.697 | 15.336 | 0.50 | 23.44 |
| 938 | C | ARG | A | 119 | 16.954 | 43.948 | 10.843 | 1.00 | 16.59 |
| 939 | O | ARG | A | 119 | 17.307 | 45.131 | 10.722 | 1.00 | 18.33 |
| 940 | N | LYS | A | 120 | 17.783 | 42.913 | 10.695 | 1.00 | 16.72 |
| 941 | CA | LYS | A | 120 | 19.206 | 43.113 | 10.407 | 1.00 | 17.81 |
| 942 | CB | LYS | A | 120 | 19.945 | 41.777 | 10.444 | 1.00 | 19.86 |
| 943 | CG | LYS | A | 120 | 21.441 | 41.907 | 10.270 | 1.00 | 22.47 |
| 944 | CD | LYS | A | 120 | 22.127 | 40.605 | 10.508 | 1.00 | 25.51 |
| 945 | CE | LYS | A | 120 | 23.622 | 40.805 | 10.517 | 1.00 | 29.10 |
| 946 | NZ | LYS | A | 120 | 24.238 | 39.467 | 10.455 | 1.00 | 27.57 |
| 947 | C | LYS | A | 120 | 19.353 | 43.759 | 9.049 | 1.00 | 19.84 |
| 948 | O | LYS | A | 120 | 20.127 | 44.721 | 8.886 | 1.00 | 20.84 |
| 949 | N | ARG | A | 121 | 18.587 | 43.256 | 8.086 | 1.00 | 16.16 |
| 950 | CA | ARG | A | 121 | 18.597 | 43.788 | 6.708 | 1.00 | 16.00 |
| 951 | CB | ARG | A | 121 | 18.041 | 42.747 | 5.732 | 1.00 | 14.54 |
| 952 | CG | ARG | A | 121 | 18.815 | 41.472 | 5.727 | 1.00 | 14.40 |
| 953 | CD | ARG | A | 121 | 18.223 | 40.465 | 4.767 | 1.00 | 15.26 |
| 954 | NE | ARG | A | 121 | 18.925 | 39.209 | 4.868 | 1.00 | 16.91 |
| 955 | CZ | ARG | A | 121 | 18.747 | 38.187 | 4.039 | 1.00 | 17.71 |
| 956 | NH1 | ARG | A | 121 | 17.865 | 38.307 | 3.035 | 1.00 | 17.28 |
| 957 | NH2 | ARG | A | 121 | 19.415 | 37.056 | 4.216 | 1.00 | 21.13 |
| 958 | C | ARG | A | 121 | 17.788 | 45.066 | 6.557 | 1.00 | 15.53 |
| 959 | O | ARG | A | 121 | 17.820 | 45.672 | 5.477 | 1.00 | 18.69 |
| 960 | N | ASN | A | 122 | 17.048 | 45.486 | 7.589 | 1.00 | 14.07 |
| 961 | CA | ASN | A | 122 | 16.243 | 46.708 | 7.514 | 1.00 | 17.04 |
| 962 | CB | ASN | A | 122 | 17.137 | 47.955 | 7.244 | 1.00 | 22.48 |
| 963 | CG | ASN | A | 122 | 18.320 | 48.072 | 8.239 | 1.00 | 29.06 |
| 964 | OD1 | ASN | A | 122 | 18.130 | 48.029 | 9.454 | 1.00 | 28.68 |
| 965 | ND2 | ASN | A | 122 | 19.547 | 48.221 | 7.703 | 1.00 | 27.29 |
| 966 | C | ASN | A | 122 | 15.150 | 46.621 | 6.464 | 1.00 | 18.23 |
| 967 | O | ASN | A | 122 | 14.860 | 47.594 | 5.774 | 1.00 | 18.73 |
| 968 | N | VAL | A | 123 | 14.536 | 45.447 | 6.341 | 1.00 | 16.71 |
| 969 | CA | VAL | A | 123 | 13.461 | 45.251 | 5.376 | 1.00 | 15.28 |
| 970 | CB | VAL | A | 123 | 13.843 | 44.253 | 4.282 | 1.00 | 13.67 |
| 971 | CG1 | VAL | A | 123 | 15.122 | 44.801 | 3.503 | 1.00 | 17.85 |
| 972 | CG2 | VAL | A | 123 | 14.122 | 42.824 | 4.878 | 1.00 | 13.19 |
| 973 | C | VAL | A | 123 | 12.160 | 44.770 | 6.038 | 1.00 | 12.69 |

-continued

Atomic coordinates of the native S8 structure
CRYST1 42.100 55.500 61.400 90.00 90.00 90.00

| ATOM | | RESIDUE | | | X | Y | Z | Occ | B |
|---|---|---|---|---|---|---|---|---|---|
| 974 | O | VAL | A | 123 | 12.162 | 44.216 | 7.132 | 1.00 | 17.06 |
| 975 | N | GLY | A | 124 | 11.069 | 44.998 | 5.329 | 1.00 | 17.32 |
| 976 | CA | GLY | A | 124 | 9.793 | 44.462 | 5.785 | 1.00 | 15.85 |
| 977 | C | GLY | A | 124 | 9.432 | 43.252 | 4.931 | 1.00 | 16.00 |
| 978 | O | GLY | A | 124 | 10.264 | 42.696 | 4.186 | 1.00 | 16.36 |
| 979 | N | GLY | A | 125 | 8.182 | 42.775 | 5.037 | 1.00 | 10.61 |
| 980 | CA | GLY | A | 125 | 7.835 | 41.654 | 4.192 | 1.00 | 9.89 |
| 981 | C | GLY | A | 125 | 6.506 | 41.030 | 4.638 | 1.00 | 9.46 |
| 982 | O | GLY | A | 125 | 5.906 | 41.495 | 5.600 | 1.00 | 10.75 |
| 983 | N | GLU | A | 126 | 6.039 | 40.049 | 3.903 | 1.00 | 9.36 |
| 984 | CA | GLU | A | 126 | 4.803 | 39.356 | 4.277 | 1.00 | 9.61 |
| 985 | CB | GLU | A | 126 | 4.271 | 38.551 | 3.071 | 1.00 | 11.09 |
| 986 | CG | GLU | A | 126 | 2.972 | 37.777 | 3.385 | 1.00 | 10.61 |
| 987 | CD A | GLU | A | 126 | 2.484 | 36.896 | 2.225 | 0.50 | 12.54 |
| 988 | CD B | GLU | A | 126 | 2.185 | 37.457 | 2.115 | 0.50 | 10.50 |
| 989 | OE1A | GLU | A | 126 | 1.489 | 36.172 | 2.438 | 0.50 | 12.17 |
| 990 | OE1B | GLU | A | 126 | 1.219 | 36.688 | 2.239 | 0.50 | 11.10 |
| 991 | OE2A | GLU | A | 126 | 3.085 | 36.928 | 1.122 | 0.50 | 16.76 |
| 992 | OE2B | GLU | A | 126 | 2.520 | 37.960 | 0.999 | 0.50 | 8.65 |
| 993 | C | GLU | A | 126 | 5.065 | 38.409 | 5.444 | 1.00 | 10.32 |
| 994 | O | GLU | A | 126 | 5.984 | 37.577 | 5.426 | 1.00 | 10.19 |
| 995 | N | ILE | A | 127 | 4.243 | 38.516 | 6.496 | 1.00 | 8.30 |
| 996 | CA | ILE | A | 127 | 4.435 | 37.661 | 7.668 | 1.00 | 8.50 |
| 997 | CB | ILE | A | 127 | 3.927 | 38.380 | 8.967 | 1.00 | 11.00 |
| 998 | CG2 | ILE | A | 127 | 4.258 | 37.485 | 10.202 | 1.00 | 10.20 |
| 999 | CG1 | ILE | A | 127 | 4.566 | 39.791 | 9.075 | 1.00 | 9.94 |
| 1000 | CD1 | ILE | A | 127 | 6.081 | 39.758 | 9.113 | 1.00 | 11.70 |
| 1001 | C | ILE | A | 127 | 3.659 | 36.378 | 7.442 | 1.00 | 12.94 |
| 1002 | O | ILE | A | 127 | 2.459 | 36.309 | 7.583 | 1.00 | 12.22 |
| 1003 | N | ILE | A | 128 | 4.385 | 35.338 | 7.127 | 1.00 | 8.16 |
| 1004 | CA | ILE | A | 128 | 3.788 | 34.069 | 6.756 | 1.00 | 8.43 |
| 1005 | CB | ILE | A | 128 | 4.893 | 33.088 | 6.162 | 1.00 | 11.68 |
| 1006 | CG2 | ILE | A | 128 | 4.278 | 31.664 | 5.893 | 1.00 | 15.27 |
| 1007 | CG1 | ILE | A | 128 | 5.483 | 33.723 | 4.912 | 1.00 | 14.92 |
| 1008 | CD1 | ILE | A | 128 | 6.709 | 32.916 | 4.404 | 1.00 | 15.70 |
| 1009 | C | ILE | A | 128 | 3.225 | 33.362 | 7.969 | 1.00 | 11.10 |
| 1010 | O | ILE | A | 128 | 2.098 | 32.815 | 7.928 | 1.00 | 11.36 |
| 1011 | N | ALA | A | 129 | 4.001 | 33.360 | 9.056 | 1.00 | 8.42 |
| 1012 | CA | ALA | A | 129 | 3.651 | 32.517 | 10.190 | 1.00 | 11.31 |
| 1013 | CB | ALA | A | 129 | 3.886 | 31.030 | 9.831 | 1.00 | 12.62 |
| 1014 | C | ALA | A | 129 | 4.538 | 32.857 | 11.358 | 1.00 | 11.70 |
| 1015 | O | ALA | A | 129 | 5.573 | 33.471 | 11.188 | 1.00 | 10.52 |
| 1016 | N | TYR | A | 130 | 4.128 | 32.376 | 12.524 | 1.00 | 12.71 |
| 1017 | CA | TYR | A | 130 | 4.912 | 32.503 | 13.772 | 1.00 | 11.06 |
| 1018 | CB | TYR | A | 130 | 4.096 | 33.153 | 14.884 | 1.00 | 9.73 |
| 1019 | CG | TYR | A | 130 | 3.810 | 34.647 | 14.798 | 1.00 | 13.43 |
| 1020 | CD1 | TYR | A | 130 | 2.929 | 35.276 | 15.743 | 1.00 | 13.93 |
| 1021 | CE1 | TYR | A | 130 | 2.711 | 36.649 | 15.720 | 1.00 | 12.86 |
| 1022 | CD2 | TYR | A | 130 | 4.440 | 35.453 | 13.850 | 1.00 | 13.69 |
| 1023 | CE2 | TYR | A | 130 | 4.206 | 36.814 | 13.815 | 1.00 | 12.21 |
| 1024 | CZ | TYR | A | 130 | 3.361 | 37.403 | 14.744 | 1.00 | 14.07 |
| 1025 | OH | TYR | A | 130 | 3.164 | 38.783 | 14.702 | 1.00 | 19.26 |
| 1026 | C | TYR | A | 130 | 5.197 | 31.077 | 14.232 | 1.00 | 12.06 |
| 1027 | O | TYR | A | 130 | 4.330 | 30.179 | 14.093 | 1.00 | 13.06 |
| 1028 | N | VAL | A | 131 | 6.384 | 30.847 | 14.761 | 1.00 | 12.37 |
| 1029 | CA | VAL | A | 131 | 6.746 | 29.545 | 15.321 | 1.00 | 10.90 |
| 1030 | CB | VAL | A | 131 | 7.705 | 28.725 | 14.383 | 1.00 | 12.13 |
| 1031 | CG1 | VAL | A | 131 | 8.111 | 27.380 | 15.002 | 1.00 | 13.61 |
| 1032 | CG2 | VAL | A | 131 | 6.977 | 28.472 | 13.036 | 1.00 | 13.82 |
| 1033 | C | VAL | A | 131 | 7.443 | 29.836 | 16.639 | 1.00 | 12.68 |
| 1034 | O | VAL | A | 131 | 8.233 | 30.741 | 16.707 | 1.00 | 12.17 |
| 1035 | N | TRP | A | 132 | 7.148 | 29.060 | 17.688 | 1.00 | 11.81 |
| 1036 | CA | TRP | A | 132 | 7.791 | 29.277 | 18.979 | 1.00 | 10.13 |
| 1037 | CB | TRP | A | 132 | 6.984 | 30.310 | 19.794 | 1.00 | 12.88 |
| 1038 | CG | TRP | A | 132 | 5.533 | 29.885 | 20.176 | 1.00 | 14.49 |
| 1039 | CD2 | TRP | A | 132 | 4.353 | 29.986 | 19.348 | 1.00 | 13.75 |
| 1040 | CE2 | TRP | A | 132 | 3.279 | 29.441 | 20.090 | 1.00 | 18.93 |
| 1041 | CE3 | TRP | A | 132 | 4.108 | 30.484 | 18.058 | 1.00 | 15.41 |
| 1042 | CD1 | TRP | A | 132 | 5.129 | 29.306 | 21.355 | 1.00 | 15.76 |
| 1043 | NE1 | TRP | A | 132 | 3.787 | 29.049 | 21.303 | 1.00 | 18.78 |
| 1044 | CZ2 | TRP | A | 132 | 1.975 | 29.369 | 19.589 | 1.00 | 19.22 |
| 1045 | CZ3 | TRP | A | 132 | 2.803 | 30.412 | 17.548 | 1.00 | 18.59 |
| 1046 | CH2 | TRP | A | 132 | 1.748 | 29.854 | 18.316 | 1.00 | 18.85 |
| 1047 | C | TRP | A | 132 | 7.888 | 27.986 | 19.747 | 1.00 | 13.45 |

-continued

Atomic coordinates of the native S8 structure
CRYST1 42.100 55.500 61.400 90.00 90.00 90.00

| ATOM | RESIDUE | | | X | Y | Z | Occ | B |
|---|---|---|---|---|---|---|---|---|
| 1048 O | TRP | A | 132 | 8.580 | 28.009 | 20.780 | 1.00 | 14.24 |
| 1049 OXT | TRP | A | 132 | 7.328 | 26.956 | 19.320 | 1.00 | 12.97 |
| 1050 OH2 | WAT | w | 3 | 0.261 | 32.289 | 0.727 | 1.00 | 26.37 |
| 1051 OH2 | WAT | W | 4 | 18.155 | 41.673 | 14.092 | 1.00 | 22.07 |
| 1052 OH2 | WAT | W | 5 | 3.066 | 13.691 | 1.139 | 1.00 | 31.38 |
| 1053 OH2 | WAT | W | 6 | −2.001 | 26.219 | 10.471 | 1.00 | 17.18 |
| 1054 OH2 | WAT | W | 7 | −3.962 | 21.533 | 14.199 | 1.00 | 24.79 |
| 1055 OH2 | WAT | W | 9 | −4.219 | 27.772 | 10.372 | 1.00 | 22.54 |
| 1056 OH2 | WAT | W | 10 | 16.168 | 22.783 | −3.704 | 1.00 | 40.38 |
| 1057 OH2 | WAT | W | 11 | 9.463 | 12.123 | 32.594 | 1.00 | 26.12 |
| 1058 OH2 | WAT | W | 15 | 7.517 | 46.701 | 0.692 | 1.00 | 28.15 |
| 1059 OH2 | WAT | W | 16 | 15.058 | 28.701 | 3.574 | 1.00 | 19.86 |
| 1060 OH2 | WAT | W | 17 | 7.778 | 8.089 | 14.852 | 1.00 | 34.39 |
| 1061 OH2 | WAT | W | 18 | 11.071 | 29.126 | 20.872 | 1.00 | 14.13 |
| 1062 OH2 | WAT | W | 21 | 5.925 | 27.933 | −3.858 | 1.00 | 23.69 |
| 1063 OH2 | WAT | W | 22 | 17.743 | 35.692 | 1.568 | 1.00 | 23.60 |
| 1064 OH2 | WAT | W | 23 | 7.425 | 8.969 | 12.487 | 1.00 | 35.37 |
| 1065 OH2 | WAT | W | 24 | −9.657 | 32.414 | 7.871 | 1.00 | 49.96 |
| 1066 OH2 | WAT | W | 27 | −4.630 | 36.813 | 7.612 | 1.00 | 15.21 |
| 1067 OH2 | WAT | W | 28 | 14.275 | 36.488 | −5.206 | 1.00 | 17.71 |
| 1068 OH2 | WAT | W | 30 | −10.848 | 38.870 | 1.955 | 1.00 | 25.53 |
| 1069 OH2 | WAT | W | 31 | 0.258 | 18.619 | 24.130 | 1.00 | 30.00 |
| 1070 OH2 | WAT | W | 33 | 20.547 | 24.643 | 16.358 | 1.00 | 38.93 |
| 1071 OH2 | WAT | W | 34 | 2.932 | 31.091 | −1.203 | 1.00 | 32.87 |
| 1072 OH2 | WAT | W | 35 | 13.726 | 13.258 | 31.530 | 1.00 | 16.96 |
| 1073 OH2 | WAT | W | 36 | 9.272 | 47.892 | 4.417 | 1.00 | 27.08 |
| 1074 OH2 | WAT | W | 38 | 18.453 | 24.784 | 6.373 | 1.00 | 33.48 |
| 1075 OH2 | WAT | W | 39 | 16.016 | 33.339 | −2.654 | 1.00 | 21.68 |
| 1076 OH2 | WAT | W | 40 | 9.305 | 10.547 | 18.786 | 1.00 | 29.41 |
| 1077 OH2 | WAT | W | 41 | 16.215 | 43.320 | −0.448 | 1.00 | 21.67 |
| 1078 OH2 | WAT | W | 43 | −6.859 | 22.079 | 2.725 | 1.00 | 45.81 |
| 1079 OH2 | WAT | W | 44 | 1.105 | 13.913 | 2.759 | 1.00 | 37.15 |
| 1080 OH2 | WAT | W | 45 | 2.068 | 33.869 | 3.100 | 1.00 | 17.17 |
| 1081 OH2 | WAT | W | 46 | 9.123 | 25.869 | 22.179 | 1.00 | 15.32 |
| 1082 OH2 | WAT | W | 47 | 14.820 | 31.217 | 2.423 | 1.00 | 19.05 |
| 1083 OH2 | WAT | W | 48 | 15.352 | 13.453 | 23.126 | 1.00 | 36.77 |
| 1084 OH2 | WAT | W | 49 | 15.393 | 21.125 | 30.136 | 1.00 | 28.18 |
| 1085 OH2 | WAT | W | 50 | 10.067 | 35.302 | −0.416 | 1.00 | 16.41 |
| 1086 OH2 | WAT | W | 52 | 6.479 | 39.660 | 20.953 | 1.00 | 29.28 |
| 1087 OH2 | WAT | W | 53 | 3.557 | 11.517 | 7.070 | 1.00 | 27.25 |
| 1088 OH2 | WAT | W | 54 | 21.164 | 16.162 | 27.968 | 1.00 | 32.52 |
| 1089 OH2 | WAT | W | 55 | 16.536 | 20.422 | 25.510 | 1.00 | 31.71 |
| 1090 OH2 | WAT | W | 56 | 10.272 | 19.641 | 15.854 | 1.00 | 14.72 |
| 1091 OH2 | WAT | W | 58 | 8.893 | 12.169 | 21.730 | 1.00 | 31.16 |
| 1092 OH2 | WAT | W | 59 | 17.216 | 35.031 | −4.063 | 1.00 | 23.65 |
| 1093 OH2 | WAT | W | 61 | 13.867 | 22.615 | 28.037 | 1.00 | 27.42 |
| 1094 OH2 | WAT | W | 62 | 6.823 | 52.637 | 12.444 | 1.00 | 38.27 |
| 1095 OH2 | WAT | W | 63 | 12.660 | 25.624 | 20.931 | 1.00 | 29.04 |
| 1096 OH2 | WAT | W | 65 | 9.179 | 19.611 | 18.377 | 1.00 | 12.64 |
| 1097 OH2 | WAT | W | 66 | 12.788 | 26.455 | −2.296 | 1.00 | 21.40 |
| 1098 OH2 | WAT | W | 68 | 1.620 | 13.251 | 10.080 | 1.00 | 33.25 |
| 1099 OH2 | WAT | W | 71 | 16.232 | 41.515 | 16.169 | 1.00 | 26.22 |
| 1100 OH2 | WAT | W | 74 | 4.087 | 10.020 | −1.602 | 1.00 | 35.87 |
| 1101 OH2 | WAT | W | 76 | 1.542 | 24.687 | −3.416 | 1.00 | 30.17 |
| 1102 OH2 | WAT | W | 83 | 3.523 | 8.602 | 19.487 | 1.00 | 16.30 |
| 1103 OH2 | WAT | W | 86 | 11.210 | 46.885 | 3.041 | 1.00 | 26.46 |
| 1104 OH2 | WAT | W | 87 | 19.040 | 30.033 | 2.757 | 1.00 | 42.90 |
| 1105 OH2 | WAT | W | 89 | 1.184 | 23.315 | 19.085 | 1.00 | 19.00 |
| 1106 OH2 | WAT | W | 92 | 12.801 | 45.216 | 9.729 | 1.00 | 21.02 |
| 1107 OH2 | WAT | W | 93 | 18.293 | 19.615 | 22.198 | 1.00 | 41.60 |
| 1108 OH2 | WAT | W | 94 | 17.487 | 34.488 | 12.316 | 1.00 | 22.73 |
| 1109 OH2 | WAT | W | 95 | −7.069 | 36.729 | 8.954 | 1.00 | 22.21 |
| 1110 OH2 | WAT | W | 97 | −6.520 | 27.123 | 5.883 | 1.00 | 27.24 |
| 1111 OH2 | WAT | W | 98 | 10.994 | 10.078 | −9.567 | 1.00 | 37.87 |
| 1112 OH2 | WAT | W | 99 | 19.626 | 34.512 | 8.612 | 1.00 | 40.75 |
| 1113 OH2 | WAT | W | 101 | 1.015 | 16.289 | 25.198 | 1.00 | 15.37 |
| 1114 OH2 | WAT | W | 102 | 0.276 | 25.494 | 17.431 | 1.00 | 15.36 |
| 1115 OH2 | WAT | W | 103 | 2.139 | 20.825 | 18.331 | 1.00 | 15.98 |
| 1116 OH2 | WAT | W | 104 | 16.691 | 34.142 | 8.038 | 1.00 | 17.77 |
| 1117 OH2 | WAT | W | 105 | −2.802 | 28.998 | 12.507 | 1.00 | 19.40 |
| 1118 OH2 | WAT | W | 106 | 6.285 | 25.347 | −6.096 | 1.00 | 20.12 |
| 1119 OH2 | WAT | W | 107 | 10.723 | 37.111 | 17.353 | 1.00 | 16.57 |
| 1120 OH2 | WAT | W | 108 | 1.745 | 19.796 | 20.994 | 1.00 | 20.57 |
| 1121 OH2 | WAT | W | 109 | 2.983 | 26.279 | −1.443 | 1.00 | 22.32 |

-continued

Atomic coordinates of the native S8 structure
CRYST1 42.100 55.500 61.400 90.00 90.00 90.00

| ATOM | RESIDUE | | | X | Y | Z | Occ | B |
|---|---|---|---|---|---|---|---|---|
| 1122 OH2 | WAT | W | 110 | 7.048 | 22.458 | 24.019 | 1.00 | 19.45 |
| 1123 OH2 | WAT | W | 111 | −1.785 | 36.791 | 1.344 | 1.00 | 27.44 |
| 1124 OH2 | WAT | W | 112 | 3.107 | 21.974 | 22.207 | 1.00 | 23.19 |
| 1125 OH2 | WAT | W | 113 | −5.384 | 29.592 | 5.922 | 1.00 | 20.68 |
| 1126 OH2 | WAT | W | 114 | 0.554 | 15.364 | 10.840 | 1.00 | 20.38 |
| 1127 OH2 | WAT | W | 115 | 16.165 | 27.477 | 1.361 | 1.00 | 28.18 |
| 1128 OH2 | WAT | W | 116 | 14.556 | 47.250 | 10.297 | 1.00 | 22.90 |
| 1129 OH2 | WAT | W | 117 | 18.154 | 21.823 | 13.453 | 1.00 | 28.48 |
| 1130 OH2 | WAT | W | 118 | 15.610 | 40.135 | 2.416 | 1.00 | 21.57 |
| 1131 OH2 | WAT | W | 120 | 9.946 | 38.683 | 27.554 | 1.00 | 22.08 |
| 1132 OH2 | WAT | W | 121 | 13.699 | 35.927 | 14.523 | 1.00 | 21.15 |
| 1133 OH2 | WAT | W | 122 | 1.632 | 28.671 | −1.043 | 1.00 | 25.21 |
| 1134 OH2 | WAT | W | 123 | 14.933 | 14.669 | 18.467 | 1.00 | 22.96 |
| 1135 OH2 | WAT | W | 124 | 16.737 | 47.364 | 11.299 | 1.00 | 29.14 |
| 1136 OH2 | WAT | W | 125 | −3.093 | 19.738 | 7.218 | 1.00 | 23.07 |
| 1137 OH2 | WAT | W | 126 | 10.379 | 33.025 | −1.744 | 1.00 | 25.17 |
| 1138 OH2 | WAT | W | 127 | 9.954 | 25.754 | 24.878 | 1.00 | 22.93 |
| 1139 OH2 | WAT | W | 128 | 13.853 | 33.965 | −4.009 | 1.00 | 25.23 |
| 1140 OH2 | WAT | W | 129 | −0.809 | 29.646 | 0.277 | 1.00 | 24.06 |
| 1141 OH2 | WAT | W | 130 | 9.502 | 51.180 | 7.807 | 1.00 | 25.54 |
| 1142 OH2 | WAT | W | 131 | 13.068 | 48.612 | 2.146 | 1.00 | 27.48 |
| 1143 OH2 | WAT | W | 132 | 14.127 | 42.274 | 0.839 | 1.00 | 23.95 |
| 1144 OH2 | WAT | W | 133 | 13.134 | 13.190 | 14.286 | 1.00 | 23.18 |
| 1145 OH2 | WAT | W | 134 | 15.159 | 12.904 | 20.597 | 1.00 | 26.16 |
| 1146 OH2 | WAT | W | 135 | 10.440 | 23.032 | 24.629 | 1.00 | 23.66 |
| 1147 OH2 | WAT | W | 136 | −3.713 | 37.445 | −0.713 | 1.00 | 28.18 |
| 1148 OH2 | WAT | W | 137 | 0.604 | 21.676 | 2.201 | 1.00 | 25.71 |
| 1149 OH2 | WAT | W | 138 | 1.066 | 37.345 | −1.106 | 1.00 | 34.42 |
| 1150 OH2 | WAT | W | 139 | 16.905 | 23.452 | 19.180 | 1.00 | 34.87 |
| 1151 OH2 | WAT | W | 140 | 4.185 | 36.771 | 20.480 | 1.00 | 40.00 |
| 1152 OH2 | WAT | W | 142 | 10.914 | 13.273 | 30.854 | 1.00 | 24.89 |
| 1153 OH2 | WAT | W | 143 | 3.873 | 16.101 | −4.915 | 1.00 | 28.61 |
| 1154 OH2 | WAT | W | 144 | 11.111 | 36.927 | 25.805 | 1.00 | 25.96 |
| 1155 OH2 | WAT | W | 145 | 13.608 | 12.384 | 16.901 | 1.00 | 23.49 |
| 1156 OH2 | WAT | W | 146 | −0.954 | 11.414 | −9.353 | 1.00 | 36.01 |
| 1157 OH2 | WAT | W | 147 | 16.603 | 32.573 | 5.264 | 1.00 | 23.66 |
| 1158 OH2 | WAT | W | 148 | 12.092 | 41.853 | 23.010 | 1.00 | 25.81 |
| 1159 OH2 | WAT | W | 149 | 11.751 | 10.811 | 17.753 | 1.00 | 27.61 |
| 1160 OH2 | WAT | W | 150 | 17.393 | 29.734 | 4.814 | 1.00 | 33.79 |
| 1161 OH2 | WAT | W | 151 | 16.056 | 33.961 | 14.670 | 1.00 | 30.25 |
| 1162 OH2 | WAT | W | 152 | −1.210 | 27.071 | 19.148 | 1.00 | 28.86 |
| 1163 OH2 | WAT | W | 153 | −6.321 | 36.116 | 11.372 | 1.00 | 33.09 |
| 1164 OH2 | WAT | W | 154 | 2.148 | 47.680 | 13.303 | 1.00 | 25.86 |
| 1165 OH2 | WAT | W | 155 | 14.992 | 11.270 | 27.745 | 1.00 | 31.33 |
| 1166 OH2 | WAT | W | 156 | −1.274 | 22.960 | 20.245 | 1.00 | 29.25 |
| 1167 OH2 | WAT | W | 157 | 1.590 | 28.270 | 23.231 | 1.00 | 33.45 |
| 1168 OH2 | WAT | W | 158 | 12.847 | 26.022 | −7.530 | 1.00 | 29.22 |
| 1169 OH2 | WAT | W | 159 | 4.214 | 11.114 | 1.150 | 1.00 | 24.17 |
| 1170 OH2 | WAT | W | 160 | −1.655 | 11.811 | 13.568 | 1.00 | 29.91 |
| 1171 OH2 | WAT | W | 161 | 2.666 | 20.185 | −4.292 | 1.00 | 38.55 |
| 1172 OH2 | WAT | W | 162 | 14.926 | 31.740 | −1.411 | 1.00 | 28.82 |
| 1173 OH2 | WAT | W | 163 | 15.004 | 47.207 | 13.602 | 1.00 | 42.80 |
| 1174 OH2 | WAT | W | 164 | 14.059 | 33.176 | 18.340 | 1.00 | 27.02 |
| 1175 OH2 | WAT | W | 165 | 10.371 | 7.912 | −3.670 | 1.00 | 43.64 |
| 1176 OH2 | WAT | W | 166 | −5.215 | 23.809 | 8.874 | 1.00 | 30.82 |
| 1177 OH2 | WAT | W | 167 | −1.687 | 21.400 | 0.893 | 1.00 | 32.38 |
| 1178 OH2 | WAT | W | 168 | 5.863 | 41.998 | 26.689 | 1.00 | 36.28 |
| 1179 OH2 | WAT | W | 169 | 18.586 | 43.498 | 2.324 | 1.00 | 41.21 |
| 1180 OH2 | WAT | W | 170 | 9.137 | 22.594 | 27.102 | 1.00 | 27.05 |
| 1181 OH2 | WAT | W | 171 | 19.822 | 37.167 | 11.677 | 1.00 | 33.36 |
| 1182 OH2 | WAT | W | 172 | 12.631 | 24.517 | −4.342 | 1.00 | 31.01 |
| 1183 OH2 | WAT | W | 173 | 20.730 | 24.100 | 8.177 | 1.00 | 37.46 |
| 1184 OH2 | WAT | W | 174 | 22.422 | 39.621 | 6.823 | 1.00 | 34.02 |
| 1185 OH2 | WAT | W | 175 | 3.034 | 33.133 | 0.552 | 1.00 | 35.38 |
| 1186 OH2 | WAT | W | 176 | 20.107 | 21.863 | 5.289 | 1.00 | 39.46 |
| 1187 OH2 | WAT | W | 177 | 17.163 | 31.964 | 1.388 | 1.00 | 42.30 |
| 1188 OH2 | WAT | W | 178 | 12.187 | 29.146 | −3.563 | 1.00 | 31.78 |
| 1189 OH2 | WAT | W | 179 | −6.222 | 25.258 | 3.777 | 1.00 | 28.97 |
| 1190 OH2 | WAT | W | 180 | 12.001 | 47.032 | 13.002 | 1.00 | 29.82 |
| 1191 OH2 | WAT | W | 181 | 22.795 | 37.299 | 9.451 | 1.00 | 42.30 |
| 1192 OH2 | WAT | W | 182 | −7.525 | 30.698 | 4.806 | 1.00 | 36.37 |
| 1193 OH2 | WAT | W | 183 | −5.215 | 29.584 | 8.649 | 1.00 | 30.25 |
| 1194 OH2 | WAT | W | 184 | 19.872 | 33.405 | −4.183 | 1.00 | 36.05 |
| 1195 OH2 | WAT | W | 185 | 4.744 | 20.991 | 24.051 | 1.00 | 25.27 |

-continued

Atomic coordinates of the native S8 structure
CRYST1 42.100 55.500 61.400 90.00 90.00 90.00

| ATOM | RESIDUE | | | X | Y | Z | Occ | B |
|---|---|---|---|---|---|---|---|---|
| 1196 OH2 | WAT | W | 186 | 11.400 | 11.709 | 22.297 | 1.00 | 28.93 |
| 1197 OH2 | WAT | W | 187 | −9.057 | 34.780 | 8.847 | 1.00 | 33.56 |
| 1198 OH2 | WAT | W | 188 | −2.249 | 15.984 | 10.194 | 1.00 | 32.98 |
| 1199 OH2 | WAT | W | 189 | −2.884 | 24.955 | 19.234 | 1.00 | 36.03 |
| 1200 OH2 | WAT | W | 190 | 9.696 | 50.530 | 4.968 | 1.00 | 35.77 |
| 1201 OH2 | WAT | W | 191 | 21.019 | 30.872 | 11.346 | 1.00 | 38.17 |
| 1202 OH2 | WAT | W | 192 | 14.204 | 30.960 | 21.968 | 1.00 | 25.74 |
| 1203 OH2 | WAT | W | 193 | −7.976 | 32.734 | 3.191 | 1.00 | 36.90 |
| 1204 OH2 | WAT | W | 194 | 14.461 | 50.113 | 6.091 | 1.00 | 29.97 |
| 1205 OH2 | WAT | W | 195 | 17.801 | 16.321 | 21.589 | 1.00 | 36.20 |
| 1206 OH2 | WAT | W | 197 | 18.581 | 44.348 | 14.054 | 1.00 | 30.95 |
| 1207 OH2 | WAT | W | 198 | 2.731 | 12.003 | −3.103 | 1.00 | 33.47 |
| 1208 OH2 | WAT | W | 199 | 14.447 | 21.324 | 23.946 | 1.00 | 37.36 |
| 1209 OH2 | WAT | W | 200 | −4.238 | 31.779 | 12.341 | 1.00 | 29.12 |
| 1210 OH2 | WAT | W | 201 | 4.514 | 2.957 | 12.647 | 1.00 | 44.36 |
| 1211 OH2 | WAT | W | 203 | 0.642 | 19.740 | 3.863 | 1.00 | 38.63 |
| 1212 OH2 | WAT | W | 205 | 6.790 | 9.078 | −2.562 | 1.00 | 40.08 |
| 1213 OH2 | WAT | W | 206 | 4.797 | 31.295 | −3.250 | 1.00 | 33.26 |
| 1214 OH2 | WAT | W | 207 | 20.687 | 40.871 | 14.582 | 1.00 | 43.83 |
| 1215 OH2 | WAT | W | 211 | 19.926 | 29.795 | 15.512 | 1.00 | 44.11 |
| 1216 OH2 | WAT | W | 212 | −2.671 | 29.660 | −1.627 | 1.00 | 31.81 |
| 1217 OH2 | WAT | W | 213 | 15.587 | 48.423 | 3.075 | 1.00 | 30.76 |
| 1218 OH2 | WAT | W | 214 | 17.679 | 19.494 | 4.704 | 1.00 | 40.20 |
| 1219 OH2 | WAT | W | 215 | 14.957 | 25.819 | 0.027 | 1.00 | 33.37 |
| 1220 OH2 | WAT | W | 216 | 15.118 | 34.866 | 16.687 | 1.00 | 36.89 |
| 1221 OH2 | WAT | W | 217 | −6.271 | 21.840 | 12.594 | 1.00 | 43.41 |
| 1222 OH2 | WAT | W | 218 | 7.913 | 37.111 | 26.296 | 1.00 | 42.81 |
| 1223 OH2 | WAT | W | 219 | 19.415 | 14.734 | 23.625 | 1.00 | 33.68 |
| 1224 OH2 | WAT | W | 220 | 17.263 | 9.938 | −8.670 | 1.00 | 43.05 |
| 1225 OH2 | WAT | W | 221 | 7.507 | 8.481 | 0.718 | 1.00 | 42.02 |
| 1226 OH2 | WAT | W | 222 | 12.412 | 51.527 | 8.293 | 1.00 | 39.48 |
| 1227 OH2 | WAT | W | 223 | −4.213 | 17.630 | 16.081 | 1.00 | 28.56 |
| 1228 OH2 | WAT | W | 225 | 13.627 | 8.137 | 6.246 | 1.00 | 45.87 |
| 1229 OH2 | WAT | W | 226 | 13.553 | 49.899 | 10.508 | 1.00 | 42.09 |
| 1230 OH2 | WAT | W | 227 | 1.479 | 51.259 | 7.651 | 1.00 | 36.49 |
| 1231 OH2 | WAT | W | 229 | −6.368 | 26.008 | 8.421 | 1.00 | 35.35 |
| 1232 OH2 | WAT | W | 230 | 20.435 | 12.355 | 2.203 | 1.00 | 40.09 |
| 1233 OH2 | WAT | W | 231 | 18.153 | 28.461 | 6.720 | 1.00 | 44.41 |
| 1234 OH2 | WAT | W | 232 | 20.764 | 46.715 | 10.993 | 1.00 | 47.11 |
| 1235 OH2 | WAT | W | 233 | 4.419 | 8.228 | −5.884 | 1.00 | 37.01 |
| 1236 OH2 | WAT | W | 234 | −5.554 | 18.749 | 11.830 | 1.00 | 41.82 |
| 1237 OH2 | WAT | W | 235 | 8.115 | 47.714 | 15.867 | 1.00 | 40.18 |
| 1238 OH2 | WAT | W | 236 | 6.870 | 26.198 | 25.697 | 1.00 | 34.10 |
| 1239 OH2 | WAT | W | 237 | 10.662 | 45.778 | 14.817 | 1.00 | 35.68 |
| 1240 OH2 | WAT | W | 238 | 14.400 | 26.566 | 18.363 | 1.00 | 32.18 |
| 1241 OH2 | WAT | W | 240 | 3.335 | 45.023 | 0.285 | 1.00 | 38.84 |
| 1242 OH2 | WAT | W | 241 | 2.751 | 7.228 | 6.330 | 1.00 | 50.85 |
| 1243 OH2 | WAT | W | 242 | 5.710 | 37.994 | 25.220 | 1.00 | 37.91 |
| 1244 OH2 | WAT | W | 243 | 20.700 | 19.007 | 3.691 | 1.00 | 39.90 |
| 1245 OH2 | WAT | W | 244 | 19.908 | 16.572 | 17.568 | 1.00 | 56.94 |
| 1246 OH2 | WAT | W | 246 | 4.431 | 38.416 | 22.728 | 1.00 | 42.21 |
| 1247 OH2 | WAT | W | 247 | 8.317 | 9.182 | 6.964 | 1.00 | 54.58 |
| 1248 OH2 | WAT | W | 248 | 15.498 | 10.503 | 24.116 | 1.00 | 46.07 |
| 1249 OH2 | WAT | W | 249 | 14.443 | 8.663 | −9.508 | 1.00 | 38.83 |
| 1250 OH2 | WAT | W | 250 | 0.806 | 46.599 | 2.414 | 1.00 | 38.84 |
| 1251 OH2 | WAT | W | 251 | 15.869 | 30.188 | 16.379 | 1.00 | 38.11 |
| 1252 OH2 | WAT | W | 252 | 7.352 | 28.899 | −6.950 | 1.00 | 66.38 |
| 1253 OH2 | WAT | W | 254 | −4.943 | 12.924 | 7.071 | 1.00 | 46.90 |
| 1254 OH2 | WAT | W | 255 | −0.389 | 20.369 | 25.846 | 1.00 | 34.19 |
| 1255 OH2 | WAT | W | 256 | 19.975 | 48.181 | 4.575 | 1.00 | 41.62 |
| 1256 OH2 | WAT | W | 257 | −3.747 | 29.175 | −5.942 | 1.00 | 46.12 |
| 1257 OH2 | WAT | W | 258 | 17.067 | 29.492 | 0.012 | 1.00 | 45.57 |
| 1258 OH2 | WAT | W | 259 | −5.841 | 26.305 | 11.606 | 1.00 | 44.57 |
| 1259 OH2 | WAT | W | 261 | 3.022 | 47.371 | 8.159 | 1.00 | 27.51 |
| 1260 OH2 | WAT | W | 262 | 6.150 | 29.001 | 24.769 | 1.00 | 27.00 |
| 1261 OH2 | WAT | W | 264 | 2.492 | 49.167 | 6.241 | 1.00 | 31.67 |
| 1262 OH2 | WAT | W | 265 | 18.777 | 45.611 | 3.013 | 1.00 | 32.27 |
| 1263 OH2 | WAT | W | 266 | −11.514 | 36.131 | 7.903 | 1.00 | 33.94 |
| 1264 OH2 | WAT | W | 267 | 21.566 | 38.893 | 13.622 | 1.00 | 36.54 |
| 1265 OH2 | WAT | W | 269 | 15.298 | 19.519 | 28.683 | 1.00 | 51.15 |
| 1266 OH2 | WAT | W | 270 | 19.792 | 27.338 | 15.438 | 1.00 | 41.61 |
| 1267 OH2 | WAT | W | 271 | 15.581 | 11.901 | 13.471 | 1.00 | 33.75 |
| 1268 OH2 | WAT | W | 272 | 17.242 | 12.516 | 9.236 | 1.00 | 40.12 |
| 1269 OH2 | WAT | W | 273 | −6.961 | 15.515 | 12.385 | 1.00 | 34.15 |

-continued

| Atomic coordinates of the native S8 structure CRYST1 42.100 55.500 61.400 90.00 90.00 90.00 |||||||||
|---|---|---|---|---|---|---|---|---|
| ATOM | | RESIDUE | | | X | Y | Z | Occ | B |
| 1270 | OH2 | WAT | W | 274 | 19.422 | 14.241 | 27.137 | 1.00 | 46.30 |
| 1271 | OH2 | WAT | W | 283 | 11.632 | 7.314 | 0.873 | 1.00 | 37.15 |
| 1272 | OH2 | WAT | W | 285 | 3.527 | 24.309 | -6.074 | 1.00 | 37.02 |
| 1273 | OH2 | WAT | W | 286 | 2.752 | 33.234 | 20.239 | 1.00 | 40.00 |
| 1274 | OH2 | WAT | W | 287 | 1.873 | 2.010 | 11.965 | 1.00 | 38.57 |
| 1275 | OH2 | WAT | W | 288 | 18.284 | 30.464 | 10.373 | 1.00 | 44.52 |
| 1276 | OH2 | WAT | W | 289 | -0.575 | 17.304 | 3.770 | 1.00 | 36.81 |
| 1277 | OH2 | WAT | W | 290 | -4.610 | 26.297 | 15.067 | 1.00 | 43.10 |
| 1278 | OH2 | WAT | W | 291 | -10.059 | 35.001 | 1.831 | 1.00 | 38.83 |
| 1279 | OH2 | WAT | W | 292 | 17.153 | 31.957 | -4.434 | 1.00 | 38.60 |
| 1280 | OH2 | WAT | W | 302 | 6.023 | 49.650 | 2.731 | 1.00 | 37.67 |
| 1281 | OH2 | WAT | W | 303 | 21.385 | 13.626 | 28.217 | 1.00 | 35.56 |
| 1282 | OH2 | WAT | W | 304 | 9.966 | 48.081 | 18.517 | 1.00 | 41.63 |
| 1283 | OH2 | WAT | W | 305 | -1.894 | 34.203 | -0.825 | 1.00 | 41.23 |
| 1284 | OH2 | WAT | W | 306 | 17.745 | 15.877 | 18.835 | 1.00 | 43.82 |
| 1285 | OH2 | WAT | W | 307 | 18.401 | 15.878 | 2.446 | 1.00 | 52.53 |
| 1286 | OH2 | WAT | W | 311 | 14.094 | 37.698 | 17.136 | 1.00 | 42.65 |
| 1287 | OH2 | WAT | W | 312 | 3.354 | 11.493 | 10.405 | 1.00 | 45.24 |
| 1288 | OH2 | WAT | W | 313 | 12.941 | 11.084 | 20.255 | 1.00 | 34.51 |
| 1289 | OH2 | WAT | W | 314 | -3.497 | 28.364 | 14.837 | 1.00 | 36.86 |
| 1290 | OH2 | WAT | W | 315 | 3.319 | 36.874 | 26.026 | 1.00 | 41.44 |
| 1291 | OH2 | WAT | W | 316 | 13.467 | 27.722 | 20.512 | 1.00 | 43.33 |
| 1292 | OH2 | WAT | W | 317 | 17.053 | 25.876 | 19.181 | 1.00 | 45.68 |
| 1293 | OH2 | WAT | W | 318 | 13.795 | 30.880 | 18.217 | 1.00 | 39.19 |
| 1294 | OH2 | WAT | W | 319 | -9.397 | 37.499 | 9.389 | 1.00 | 53.51 |
| 1295 | OH2 | WAT | W | 321 | 1.652 | 0.597 | 14.057 | 1.00 | 36.90 |
| 1296 | OH2 | WAT | W | 322 | -6.598 | 30.034 | -1.987 | 1.00 | 49.18 |
| 1297 | OH2 | WAT | W | 323 | 12.454 | 23.087 | 24.086 | 1.00 | 41.19 |
| 1298 | OH2 | WAT | W | 326 | 16.710 | 42.206 | 1.767 | 1.00 | 64.24 |
| 1299 | OH2 | WAT | W | 327 | 10.083 | 29.660 | -2.635 | 1.00 | 51.02 |
| 1300 | OH2 | WAT | W | 328 | -7.804 | 30.392 | 9.431 | 1.00 | 39.03 |
| 1301 | OH2 | WAT | W | 330 | 22.466 | 48.916 | 2.705 | 1.00 | 48.85 |
| 1302 | OH2 | WAT | W | 335 | 1.496 | 21.993 | -2.407 | 1.00 | 38.10 |
| 1303 | OH2 | WAT | W | 336 | 18.283 | 33.498 | 10.149 | 1.00 | 42.45 |
| 1304 | OH2 | WAT | W | 337 | 4.233 | 30.289 | 25.277 | 1.00 | 42.76 |
| 1305 | OH2 | WAT | W | 342 | 24.038 | 47.844 | 0.868 | 1.00 | 39.88 |
| 1306 | OH2 | WAT | W | 344 | 16.813 | 14.879 | 0.411 | 1.00 | 41.75 |
| 1307 | OH2 | WAT | W | 345 | 5.438 | 7.866 | 15.715 | 1.00 | 52.84 |
| 1308 | OH2 | WAT | W | 346 | 16.291 | 23.734 | -1.125 | 1.00 | 39.55 |
| 1309 | OH2 | WAT | W | 347 | 13.025 | 9.450 | -3.178 | 1.00 | 44.56 |
| 1310 | OH2 | WAT | W | 349 | 14.233 | 22.340 | 2.733 | 1.00 | 50.22 |
| 1311 | OH2 | WAT | W | 350 | 12.227 | 23.367 | 26.694 | 1.00 | 47.09 |
| 1312 | OH2 | WAT | W | 351 | 18.563 | 36.730 | -4.783 | 1.00 | 64.01 |
| 1313 | OH2 | WAT | W | 352 | 4.655 | 14.983 | 26.660 | 1.00 | 25.91 |
| 1314 | OH2 | WAT | W | 353 | 13.122 | 7.856 | 19.736 | 1.00 | 41.94 |
| 1315 | OH2 | WAT | W | 354 | -8.723 | 27.271 | 10.140 | 1.00 | 45.47 |
| 1316 | OH2 | WAT | W | 355 | 21.589 | 17.424 | 5.171 | 1.00 | 48.12 |
| 1317 | OH2 | WAT | W | 356 | 14.998 | 11.204 | 30.356 | 1.00 | 36.89 |
| 1318 | OH2 | WAT | W | 357 | -0.410 | 34.681 | 0.810 | 1.00 | 41.71 |
| 1319 | OH2 | WAT | W | 358 | 1.781 | 24.032 | 17.043 | 1.00 | 50.64 |
| 1320 | OH2 | WAT | W | 359 | 0.847 | 18.603 | 22.240 | 1.00 | 45.03 |
| 1321 | OH2 | WAT | W | 360 | 13.105 | 36.160 | -3.586 | 1.00 | 50.05 |
| 1322 | OH2 | WAT | W | 361 | -0.679 | 20.082 | 20.448 | 1.00 | 46.12 |
| 1323 | OH2 | WAT | W | 362 | 11.784 | 45.772 | 1.769 | 1.00 | 41.27 |
| 1324 | OH2 | WAT | W | 363 | -1.314 | 36.478 | -0.558 | 1.00 | 45.13 |
| 1325 | OH2 | WAT | W | 364 | 17.040 | 12.298 | 27.168 | 1.00 | 46.18 |
| 1326 | OH2 | WAT | W | 365 | 6.404 | 26.395 | 17.529 | 1.00 | 48.11 |
| 1327 | OH2 | WAT | W | 366 | 13.011 | 50.732 | 13.200 | 1.00 | 39.87 |
| 1328 | OH2 | WAT | W | 367 | 22.712 | 37.399 | 16.781 | 1.00 | 42.06 |
| 1329 | OH2 | WAT | W | 368 | 18.576 | 33.861 | 3.979 | 1.00 | 40.44 |
| 1330 | OH2 | WAT | W | 369 | 1.340 | 17.351 | -4.937 | 1.00 | 40.33 |

What is claimed is:

1. A composition comprising a *Staphylococcus aureus* S8 rRNA-binding protein (SEQ ID NO:1) in orthorhombic crystalline form, wherein the crystalline form has lattice constants of a=42.1 Å, b=55.9 Å, c=61.3 Å, α=90.0°, β=90.0°, γ=90.0°.

2. The composition according to claim 1 wherein the crystalline form contains a *Staphylococcus aureus* S8 rRNA-binding protein (SEQ ID NO:1) molecule in the asymmetric unit.

3. The composition according to claim 1 wherein said *Staphylococcus aureus* S8 rRNA-binding protein (SEQ ID NO:1) has an active site cavity formed by the amino acids S107, T108, S109, and E126.

4. A method for the production of a *Staphylococcus aureus* S8 rRNA-binding protein in orthorhombic crystalline form having a space group of $P2_1 2_1 2_1$, said method comprising:
  a) forming sitting drops by mixing *Staphylococcus aureus* S8 rRNA-binding protein with a reservoir solution at about pH 8.5, said reservoir solution further comprises 30% PEG4000, 0.2M $Li_2SO_4$, and 0.1M Tris-HCl; and
  b) equilibrating said sitting drops at room temperature.

* * * * *

SEQUENCE LISTING

<160> NUMBER OF SEQ ID NOS: 1

<210> SEQ ID NO 1
<211> LENGTH: 132

```
-continued

<212> TYPE: PRT
<213> ORGANISM: staphylococcus aureus

<400> SEQUENCE: 1

Met Thr Met Thr Asp Pro Ile Ala Asp Met Leu Thr Arg Val Arg Asn
 1               5                  10                  15

Ala Asn Met Val Arg His Glu Lys Leu Glu Leu Pro Ala Ser Asn Ile
                20                  25                  30

Lys Lys Glu Ile Ala Glu Ile Leu Lys Ser Glu Gly Phe Ile Lys Asn
             35                  40                  45

Val Glu Tyr Val Glu Asp Lys Gln Gly Val Leu Arg Leu Phe Leu
         50                  55                  60

Lys Tyr Gly Gln Asn Asp Glu Arg Val Ile Thr Gly Leu Lys Arg Ile
 65                  70                  75                  80

Ser Lys Pro Gly Leu Arg Val Tyr Ala Lys Ala Ser Glu Met Pro Lys
                 85                  90                  95

Val Leu Asn Gly Leu Gly Ile Ala Leu Val Ser Thr Ser Glu Gly Val
                100                 105                 110

Ile Thr Asp Lys Glu Ala Arg Lys Arg Asn Val Gly Gly Glu Ile Ile
            115                 120                 125

Ala Tyr Val Trp
        130
```